United States Patent [19]

Macielag et al.

[11] Patent Number: 5,422,341
[45] Date of Patent: Jun. 6, 1995

[54] MOTILIN-LIKE POLYPEPTIDES WITH GASTROINTESTINAL MOTOR STIMULATING ACTIVITY

[75] Inventors: Mark J. Macielag, Branchburg; Ramalinga Dharanipragada, Chatham; James R. Florance, Denville; Mary S. Marvin, Morristown; Alphonse Galdes, New Providence, all of N.J.

[73] Assignee: Ohmeda Pharmaceutical Products Division Inc., Liberty Corner, N.J.

[21] Appl. No.: 103,490

[22] Filed: Aug. 6, 1993

[51] Int. Cl.$^6$ .............. A61K 38/00; C07K 5/00; C07K 7/00; C07K 17/00
[52] U.S. Cl. .............................. 514/13; 514/14; 530/326; 530/327
[58] Field of Search ............. 514/13, 14; 530/326, 530/327

[56] References Cited

FOREIGN PATENT DOCUMENTS

0378078A1  7/1990  European Pat. Off. .
2-311495  12/1990  Japan .

OTHER PUBLICATIONS

Khan et al., Biochemistry 29, 5743–5751 (1990).
Peeters et al., Gastroenterology 100, A480 (1991).
Meyer et al., Med. Klin. 86, 515–517 (1991) translation provided.
Christofides et al., Gastroenterology 76, 903–907 (1979).
Macielag et al., Peptides 13, 565–569 (1992).
Peeters et al., Peptides 13, 1103–1107 (1992).
Poitras et al., Biochem. Biophys. Res. Commun. 183, 36–40 (1992).
Fujino et al., *Peptide chemistry*, 171–176 (1977).
Yajima et al., *Gastroenterology* 72, 793–796 (1977).
Segawa et al., *J. Pharm. Pharmac.*, 28, 650–651 (1976).
Ueda et al., *Chem. Pharm. Bull.* 25(8), 2123–2126 (1977).
Peeters et al., *Biomed Res.* 9 361–366 (1988)

Kuno et al., *Chem. Pharm. Bull.* 34(11), 4811–4816 (1986).
Fauchére et al., *Advances in Drug Research*, 23 127–159 (1992).

Primary Examiner—Jill Warden
Assistant Examiner—Sheela J. Huff
Attorney, Agent, or Firm—R. Hain Swope; Larry R. Cassett

[57] ABSTRACT

This invention pertains to polypeptides, other than motilin, having gastrointestinal motor stimulating activity and represented by the formula:

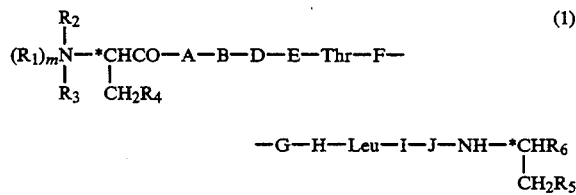

wherein A and D are lipophilic aliphatic or alicyclic amino acids; B is L-proline or L-alanine; E is an aromatic, lipophilic aliphatic, or alicyclic amino acid; F is an aromatic or heteroaromatic amino acid; G is glycine or D-alanine; H is L-glutamic acid or L-glutamine; I is L-glutamine, L-glutamic acid, or L-alanine; J is a direct bond or is selected from, inter alia Z, Z-Leu, Z-Leu-Gln, Z-Leu-Gln-Glu (SEQ ID NO:2) or Z-Leu-Gln-Glu-Lys (SEQ ID NO:3), wherein Z is, inter alia, arginine, D-arginine, D-homoarginine, or D-lysine, and further wherein the amino acids represented by A, D, E and F are L-stereoisomers; $R_1$ is lower-alkyl or allyl; $R_2$ is hydrogen, lower-alkyl, propargyl, or allyl; $R_3$ is hydrogen, lower-alkyl, and allyl; $R_4$ is lower-alkyl, cycloalkyl, heteroaryl, unsubstituted aryl, and aryl substituted by halogen, hydroxy, or lower-alkoxy; $R_5$ is —$CH_2CONH_2$, aminoalkyl, or guanidinoalkyl; $R_6$ is —COOH or —$CONH_2$; and m is 0 or 1, and the asymmetric carbon represented by * may be D or L configuration, with certain specified provisos.

31 Claims, No Drawings

MOTILIN-LIKE POLYPEPTIDES WITH GASTROINTESTINAL MOTOR STIMULATING ACTIVITY

FIELD OF THE INVENTION

This invention relates to novel polypeptides having potent gastrointestinal motor stimulating activity and enhanced metabolic stability useful in the treatment of conditions characterized by a decreased basal level of gastrointestinal motor activity such as diabetic gastroparesis, paralytic ileus, and postoperative ileus.

BACKGROUND OF THE INVENTION

Motilin is a gastrointestinal linear polypeptide hormone which stimulates the gastric antrum, duodenum, and colon. Although its effects are not completely known, motilin plays a role in increasing gastric motility and stimulating pepsin output and may also be important in regulating the interdigestive myoelectric complex. Human motilin has not yet been purified, but its immunologic properties strongly suggest that it is very similar to porcine motilin. Porcine motilin contains amino acid residues and may be represented by the formula: H-Phe-Val-Pro-Ile-Phe-Thr-Tyr-Gly-Glu-Leu-Gln-Arg-Met-Gln-Glu-Lys-Glu-Arg-Asn-Lys-Gly-Gln-OH (SEQ ID NO:1)

Porcine motilin has a hydrophobic region from positions 1 to 5, a hydrophilic region from positions 11 to 22, and a connecting region from positions 6 to 10. Porcine motilin also has an α-helical secondary structure from residues 9 to 20 of the primary sequence [Khan et al., *Biochemistry* 29, 5743–5751 (1990)].

Administration of motilin to healthy human subjects accelerates intestinal transit time and enhances gastric emptying. In vitro, motilin stimulates contractions of human and rabbit duodenal smooth muscle strips and isolated gastrointestinal smooth muscle cells. In addition, motilin and some of its derivatives compete with radiolabelled motilin for binding sites on human and rabbit antral tissue suggesting that stimulation of specific receptors in the gastrointestinal tract is responsible for the physiological effects of the hormone. Infusion of motilin has been reported to stimulate the emptying of solids and liquids in patients with diabetic gastroparesis [Peelers et al., *Gastroenterology* 100, A480 (1991)]. In addition, motilin has been used to treat patients with paralytic ileus caused by carcinoma of the gastrointestinal tract [Meyer et at., *Med. Klin.* 86, 515–517 (1991)].

A major problem with motilin is its relatively short half-life ($t_{\frac{1}{2}}$) of 4.5 minutes in humans [Christofides et al., *Gastroenterology* 76, 903–907 (1979)]. This short half-life makes it necessary to administer the hormone by continuous infusion to induce a therapeutic effect.

The N-terminal amino acid sequence and certain residues of the midportion of motilin are essential for contractile activity, [Macielag et at., *Peptides* 13, 565–569 (1992); Peeters et at., *Peptides* 13, 1103–1107 (1992); Poitras et at., *Biochem. Biophys. Res. Commun.* 183, 36–40 (1992)]. Motilin-like polypeptides which have a shorter C-terminus, contain from 3 to 5 basic amino acids bonded from position 12, and have various amino acid substitutions at positions 1 through 11 have been reported to have activity less than, or equal to, that of motilin. None of the motilin-like polypeptides were reported to have increased metabolic stability [Japanese patent no. 2-311,495].

Accordingly, a motilin-like polypeptide having potent gastrointestinal motor stimulating activity and enhanced metabolic stability would be useful for the treatment of decreased basal levels of gastrointestinal motor activity.

SUMMARY OF THE INVENTION

This invention pertains to polypeptides having gastrointestinal motor stimulating activity represented by the formula:

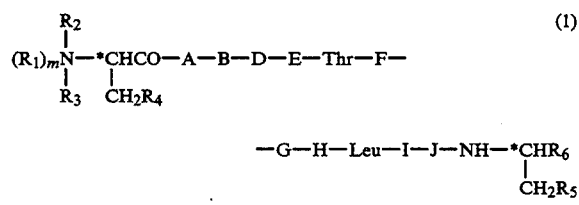

including optically active isomeric forms and the pharmaceutically acceptable acid addition salts thereof wherein:

A is the L-stereoisomer of a lipophilic aliphatic or alicyclic amino acid;

B is L-proline or L-alanine;

D is the L-stereoisomer of a lipophilic aliphatic or alicyclic amino acid;

E is the L-stereoisomer of an aromatic, lipophilic aliphatic, or alicyclic amino acid;

F is the L-stereoisomer of an aromatic or heteroaromatic amino acid;

G is glycine or D-alanine;

H is L-glutamic acid or L-glutamine;

I is L-glutamine, L-glutamic acid, or L-alanine;

J is a direct bond between I and group —NH— or is selected from the group consisting of Z, Z-Leu, Z-Leu-Gln, Z-Leu-Gln-Glu (SEQ ID NO:2), Z-Leu-Gln-Glu-Lys (SEQ ID NO:3), Z-Leu-Gln-Glu-Lys-Glu (SEQ ID NO:4), Z-Leu-Gln-Glu-Lys-Glu-Arg (SEQ ID NO:5), Z-Leu-Gln-Glu-Lys-Glu-Arg-Asn (SEQ ID NO:6), Z-Leu-Gln-Glu-Lys-Glu-Arg-Asn-Lys (SEQ ID NO: 7), and Z-Leu-Gln-Glu-Lys-Glu-Arg-Asn-Lys-Gly (SEQ ID NO:8), wherein Z is selected from the group consisting of arginine, D-arginine, D-homoarginine, D-lysine, D-ornithine, D-2,4-diaminobutyric acid, D-glutamine, D-asparagine, and D-alanine;

$R_1$ is lower-alkyl or allyl;

$R_2$ is selected from the group consisting of hydrogen, lower-alkyl, propargyl, and allyl;

$R_3$ is selected from the group consisting of hydrogen, lower-alkyl, and allyl;

$R_4$ is selected from the group consisting of lower-alkyl, cycloalkyl, substituted and unsubstituted aryl, and heteroaryl, wherein the aryl group may be substituted with one or more substituents selected from the group consisting of halogen, hydroxy, and lower-alkoxy;

$R_5$ is selected from the group consisting of —CH$_2$CONH$_2$, aminoalkyl groups containing from 1 to 3 carbon atoms, and guanidinoalkyl groups containing 2 or 3 carbon atoms;

$R_6$ is —COOH or —CONH$_2$; and m is 0 or 1, the symbol * represents an asymmetric carbon atom which may be in the D or L configuration, and each lower-alkyl group contains from 1 to 4 carbon atoms, with the proviso that:

(a) when m is 0, $R_2$ and $R_3$ are hydrogen, and J is a direct bond, the —NH—*CH(CH$_2$R$_5$)R$_6$ group has the D-configuration;

(b) $R_5$ is —CH$_2$CONH$_2$ only when J is Z-Leu or Z-Leu-Gln-Glu-Lys-Glu-Arg-Asn-Lys-Gly (SEQ ID NO:8);

(c) when m=0, $R_2$ and $R_3$ are hydrogen, and J is Z, Z-Leu, Z-Leu-Gln, Z-Leu-Gln-Glu (SEQ ID NO:2), Z-Leu-Gln-Glu-Lys (SEQ ID NO:3), Z-Leu-Gln-Glu-Lys-Glu (SEQ ID NO:4), Z-Leu-Gln-Glu-Lys-Glu-Arg (SEQ ID NO:5), Z-Leu-Gln-Glu-Lys-Glu-Arg-Asn (SEQ ID NO:6), Z-Leu-Gln-Glu-Lys-Glu-Arg-Asn-Lys (SEQ ID NO:7), and Z-Leu-Gln-Glu-Lys-Glu-Arg-Asn-Lys-Gly (SEQ ID NO:8), Z has the D configuration; and (d) the polypeptide is other than motilin.

DETAILED DESCRIPTION OF THE INVENTION

The novel polypeptides of the present invention bind with high affinity to the motilin receptor and mimic the peristaltic effects of motilin on gastrointestinal tissue. The novel polypeptides also are more effective prokinetic agents in vivo because they demonstrate increased stability to biodegradation in relevant organ tissue homogenates. The motilin-like polypeptides contain a leucine residue in place of methionine at position 13 for greater chemical stability, a D-arginine residue in place of L-arginine at position 12 for greater potency and stability, and an alkylated phenylalanine residue at position 1 for increased stability to biodegradation. The polypeptides of the present invention are therefore useful in the treatment of conditions characterized by a decreased basal level of gastrointestinal motor activity such as, diabetic gastroparesis, paralytic ileus, and post-operative ileus.

This invention pertains to novel polypeptides having potent gastrointestinal motor stimulating activity as well as to methods for treating a condition of decreased basal level of gastrointestinal motor activity in a mammal, preferably a human. The methods comprise administering to the mammal an amount, therapeutically effective to relieve the condition, of a polypeptide represented by formula (1):

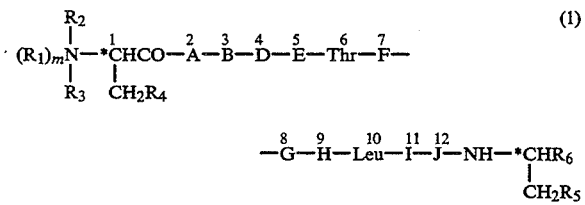

including optically active isomeric forms and the pharmaceutically acceptable acid addition salts thereof. In formula (1), m is an integer from 0 to 1, the symbol * represents an asymmetric carbon atom which may be in the D or L configuration, and each lower-alkyl group contains from 1 to 4 carbon atoms, providing that (a) when m is 0, $R_2$ and $R_3$ are hydrogen, and J is a direct bond, the —NH—*CH(CH$_2$R$_5$)R$_6$ group has the D-configuration;

(b) $R_5$ is —CH$_2$CONH$_2$ only when J is Z-Leu or Z-Leu-Gln-Glu-Lys-Glu-Arg-Asn-Lys-Gly (SEQ ID NO:8); (c) when m=0, $R_2$ and $R_3$ are hydrogen, and J is Z, Z-Leu, Z-Leu-Gln, Z-Leu-Gln-Glu (SEQ ID NO:2), Z-Leu-Gln-Glu-Lys (SEQ ID NO:3), Z-Leu-Gln-Glu-Lys-Glu (SEQ ID NO:4), Z-Leu-Gln-Glu-Lys-Glu-Arg (SEQ ID NO:5), Z-Leu-Gln-Glu-Lys-Glu-Arg-Asn (SEQ ID NO:6), Z-Leu-Gln-Glu-Lys-Glu-Arg-Asn-Lys (SEQ ID NO:7), and Z-Leu-Gln-Glu-Lys-Glu-Arg-Asn-Lys-Gly (SEQ ID NO:8), Z has the D configuration; and (d) the polypeptide is other than motilin. Groups A through J and $R_1$ through $R_6$ are defined as set forth below.

The novel compounds of the present invention defined by Formula (1) are polypeptides which may be from 12 to 22 amino acids in length, and preferably are 12, 14, 16, 18, 20, or 22 amino acids in length. The stereochemistry of the constituent amino acids of the novel polypeptides is an essential feature of this invention. The absolute stereochemistry of the individual amino acids is L, unless otherwise noted, except for position 1 (the amino-terminal amino acid, $(R_1)_m(R_2)(R_3)N$—*CH(CH$_2$R$_4$)CO—) which may be L or D, position 8 (Group G) which may be glycine or D-alanine, position 12 which may be L or D, and the C-terminal amino acid position, —NH—*CH(CH$_2$R$_5$)R$_6$, which may be L or D.

The following abbreviations employed throughout this specification are defined as set forth below:

Phe—phenylalanine
Tyr—tyrosine
Nle—norleucine
Leu—leucine
Cha—α-cyclohexylalanine
Val—valine
Ile—isoleucine
Gly—glycine
Ala—alanine
Glu—glutamic acid
Gln—glutamine
Arg—arginine
h-Arg—homoarginine
Orn—ornithine
Dab—2,4-diaminobutyric acid
Lys—lysine
Asn—asparagine
Me—methyl
Boc—t-butyloxycarbonyl
Cbz—benzyloxycarbonyl
Dhbt—3,4-dihydro-4-oxobenzotriazin-3-yl
Fmoc—fluorenylmethyloxycarbonyl
Mbh—4,4'-dimethoxybenzhydryl
Mtr—4-methoxy-2,3,6-trimethylbenzenesulfonyl
Pfp—pentafluorophenyl
Trt—trityl
BOP—benzotriazolyloxy-trisdimethylaminophosphonium hexafluorophosphate
DCC—N,N'dicyclohexylcarbodiimide
DCM—dichloromethane
DIC—diisopropylcarbodiimide
DIEA—diisopropylethylamine
EDCC—N-diethylaminopropyl-N'-cyclohex ylcarbodiimide
HBTU—2-(1H-benzotriazol-1-yl)-1,1,3,3-tetramethyluronium hexafluorophosphate
HEPES—(N-[2-hydroxyethyl]piperazine-N'-[2-ethanesulfonic acid])
HMPA—hydroxymethylphenoxyacetoxy
HOBt—1-hydroxybenzotriazole
MBHA—4-methylbenzhydrylamino
PAM—hydroxymethylphenylacetamidomethyl PyBrOP—bromo-tris-pyrrolidino-phosphonium hexafluorophosphate
DMF—N,N-dimethylformamide
NMM—N-methylmorpholine
NMP—N-methylpyrrolidinone
TCA—trichloroacetic acid
TEA—triethylamine
TFA—trifluoroacetic acid
TFMSA—trifluoromethanesulfonic acid Position 1, the amino-terminal amino acid, $(R_1)_m(R_2)(R_3)N-*CH(CH_2R_4)CO-$ The amino acid in the amino-terminal potion of the polypeptide, $(R_1)_m(R_2)(R_3)N-*CH(CH_2R_4)CO-$, in position 1 may have the L or D configuration. $R_1$ is lower-alkyl or allyl; $R_2$ may be selected from the group consisting of hydrogen, lower-alkyl, propargyl, and allyl; and $R_3$ may be selected from the group consisting of hydrogen, lower-alkyl, and allyl. The term "lower-alkyl", as used herein, refers to straight- and branched-chain hydrocarbon radicals containing from 1 to 4 carbon atoms. Examples of suitable lower-alkyl groups for $R_1$, $R_2$, and $R_3$ are methyl, ethyl, propyl, isopropyl, butyl, isobutyl, and sec-butyl, preferably methyl.

The integer m is 0 or 1 and preferably is 0. When m is 0, the amino residue may be a primary amine wherein $R_2$ and $R_3$ are hydrogen. The amino residue may also be a secondary amine, tertiary amine, or quaternary ammonium salt (m is 1) substituted by one, two, or three, respectively, lower-alkyl groups having from one to four carbon atoms, and preferably methyl or ethyl. The amino residue may also be substituted by one propargyl group to provide, e.g., N-propargyl, N-methyl-N-propargyl, N,N-dimethyl-N-propargyl substituted amino residues, or up to three allyl groups. Preferably, the amino-terminal amino acid is N-substituted, and the preferred substituents are one to three methyl groups.

$R_4$ is selected from the group consisting of lower-alkyl, cycloalkyl, substituted and unsubstituted aryl, and heteroaryl, wherein the aryl group may contain one or more substituents selected from the group consisting of halogen, hydroxy, and lower-alkoxy. Preferred substituted and unsubstituted aryl groups are phenyl, p-fluorophenyl, p-chlorophenyl, p-bromophenyl, p-iodophenyl, p-hydroxyphenyl, p-methoxyphenyl, 1-naphthyl, and 2-naphthyl. Preferred heteroaryl groups are 3-indolyl, 2-thienyl, and 3-pyridyl. Preferred cycloalkyl groups are cyclopentyl, cyclohexyl, and cycloheptyl. Preferably, $R_4$ is selected from the group consisting of methyl, ethyl, n-propyl, iso-propyl, n-butyl, cyclohexyl, phenyl, p-fluorophenyl, p-chlorophenyl, p-bromophenyl, p-iodophenyl, p-hydroxyphenyl, p-methoxyphenyl, 1-naphthyl, 2-naphthyl, 3-indolyl, 2-thienyl, and 3-pyridyl. More preferably, $R_4$ is selected from the group consisting of phenyl and cyclohexyl. Examples of the amino acid residues from which $(R_1)_m(R_2)(R_3)N-*CH(CH_2R_4)CO-$ may be derived are phenylalanine, p-fluorophenylalanine, p-chlorophenylalanine, p-bromophenylalanine, p-iodophenylalanine, tyrosine, p-methoxyphenylalanine, 1-naphthylalanine, 2-naphthylalanine, tryptophan, β-2-thienylalanine, β-3-pyridylalanine, α-aminobutyric acid, norvaline, norleucine, leucine, and cyclohexylalanine. For compounds having high levels of gastrointestinal peristaltic activity, the preferred amino-terminal amino acids are L-phenylalanine, D-phenylalanine, L-cyclohexylalanine, and D-cyclohexylalanine.

Position 2, Group A

Group A in position 2 of the polypeptide is an amino acid which is the L-stereoisomer of a lipophilic aliphatic or alicyclic amino acid. Examples of L-lipophilic aliphatic and alicyclic amino acids are L-valine, L-isoleucine, L-leucine, L-norvaline, L-norleucine, and L-cyclohexylalanine. The preferred Group A amino acids are L-valine, L-leucine, and L-isoleucine.

Position 3, Group B

Group B in position 3 of the polypeptide is an amino acid which is L-proline or L-alanine. For compounds having high levels of motilin receptor agonist activity, the preferred Group B amino acid is L-proline.

Position 4, Group D

Group D in position 4 of the polypeptide is an amino acid which is the L-stereoisomer of a lipophilic aliphatic or alicyclic amino acid. Examples of L-lipophilic aliphatic and alicyclic amino acids are L-isoleucine, L-valine, L-leucine, L-norvaline, L-norleucine, and L-cyclohexylalanine. The preferred Group D amino acids are L-isoleucine, L-leucine, and L-cyclohexylalanine.

Position 5, Group E

Group E in position 5 of the polypeptide is an amino acid which is the L-stereoisomer of an aromatic, lipophilic aliphatic, or alicyclic amino acid. Examples of L-aromatic, lipophilic aliphatic, and alicyclic amino acids are residues derived from phenylalanine, p-fluorophenylalanine, p-chlorophenylalanine, p-bromophenylalanine, p-iodophenylalanine, tyrosine, p-methoxyphenylalanine, 1-naphthylalanine, 2-naphthylalanine, leucine, and cyclohexylalanine. The preferred Group E amino acids are L-phenylalanine and L-cyclohexylalanine.

Position 6, L-threonine

The amino acid in position 6 of the polypeptide is L-threonine.

Position 7, Group F

Group F in position 7 of the polypeptide is an amino acid which is the L-stereoisomer of an aromatic or heteroaromatic amino acid. Examples of aromatic and heteroaromatic amino acids are tyrosine, phenylalanine, p-methoxyphenylalanine, histidine, tryptophan, β-2-thienylalanine, and β-3pyridylalanine. The preferred Group F amino acids are L-tyrosine, L-histidine, and L-phenylalanine.

Position 8, Group G

Group G in position 8 of the polypeptide is an amino acid which is glycine or D-alanine, and preferably is glycine.

Position 9, Group H

Group H in position 9 of the polypeptide is an amino acid which is L-glutamic acid or L-glutamine, and preferably is L-glutamic acid.

Position 10, L-leucine

The amino acid in position 10 of the polypeptide is L-leucine.

Position 11, Group I

Group I in position 11 of the polypeptide is an amino acid which is L-glutamine, L-glutamic acid, or L-alanine. The preferred Group I amino acids are L-glutamine and L-alanine.

Group J

Group J in the polypeptide may be a direct bond between Group I and the —NH— group or may be selected from the group consisting of Z, Z-Leu, Z-Leu-Gln, Z-Leu-Gln-Glu (SEQ ID NO:2), Z-Leu-Gln-Glu-Lys (SEQ ID NO:3), Z-Leu-Gln-Glu-Lys-Glu (SEQ ID NO:4), Z-Leu-Gln-Glu-Lys-Glu-Arg (SEQ ID NO:5), Z-Leu-Gln-Glu-Lys-Glu-Arg-Asn (SEQ ID NO:6), Z-Leu-Gln-Glu-Lys-Glu-Arg-Asn-Lys (SEQ ID NO:7), and Z-Leu-Gln-Glu-Lys-Glu-Arg-Asn-Lys-Gly (SEQ ID NO:8), and preferably from the group consisting of Z-Leu, Z-Leu-Gln-Glu (SEQ ID NO:2), Z-Leu-Gln-Glu-Lys-Glu (SEQ ID NO:4), Z-Leu-Gln-Glu-Lys-Glu-Arg-Asn (SEQ ID NO:6), and Z-Leu-Gln-Glu-Lys-Glu-Arg-Asn-Lys-Gly (SEQ ID NO:8). Group Z is an amino acid selected from the group consisting of arginine, D-arginine, D-homoarginine, D-lysine, D-ornithine, D-2,4-diaminobutyric acid, D-glutamine, D-asparagine, and D-alanine, preferably selected from the group consisting of arginine, D-arginine, D-glutamine, and D-alanine.

Position 12

When Group J in the polypeptide is a direct bond between Group I and the —NH— group, the polypeptide is a dodecapeptide and the amino acid in position 12 is the C-terminal portion, —NH—*CH(CH$_2$R$_5$)—R$_6$, of the polypeptide. When Group J is a direct bond and groups R$_2$ and R$_3$ in position 1 of the polypeptide are hydrogen, the amino acid in position 12 has the D configuration. Group R$_5$ is an aminoalkyl group containing from 1 to 3 carbon atoms, or a guanidinoalkyl group containing 2 or 3 carbon atoms, and preferably is selected from the group consisting of guanidinoalkyl groups containing 2 or 3 carbon atoms. Preferred aminoalkyl groups are aminomethyl, 2-aminoethyl, and 3-amino-n-propyl. Preferred guanidinoalkyl groups are N-2-guanidinoethyl and N-3-guanidino-n-propyl. Group R$_6$ is —COOH or —CONH$_2$, preferably —CONH$_2$. Preferably, the amino acid in the C-terminal portion, —NH*CH(CH$_2$R$_5$)—R$_6$, of the polypeptide in this embodiment is selected from the group consisting of arginine, D-arginine, lysine, D-lysine, D-ornithine, D-2,4-diaminobutyric acid, and D-homoarginine, and more preferably is selected from the group consisting of arginine, D-arginine, and lysine.

When Group J in the polypeptide is not a direct bond between Group I and the —NH— group, the amino acid in position 12 is Group Z. As set out above, 35 Group Z is an amino acid selected from the group consisting of arginine, D-arginine, D-homoarginine, D-lysine, D-ornithine, D-2,4-diaminobutyric acid, D-glutamine, D-asparagine, and D-alanine. Preferably, Group Z is selected from the group consisting of arginine, D-arginine, D-glutamine, and D-alanine, more preferably Group Z is D-arginine. When Groups R$_2$ and R$_3$ in position 1 of the polypeptide are hydrogen, the amino acid of Group Z has the D configuration.

Position 13

When the polypeptide in the present invention is a tridecapeptide, the amino acid in position 13 is the C-terminal portion, —NH—*CH(CH$_2$R$_5$)—R$_6$, of the polypeptide, may have the L or D configuration, and may be selected from the group consisting of lysine, ornithine, 2,4-diaminobutyric acid, arginine, and lo homoarginine, preferably L-lysine or D-lysine.

When the polypeptide of the present invention is larger than a tridecapeptide, the amino acid in position 13 is L-leucine.

Position 14

When the polypeptide in the present invention is a tetradecapeptide, the amino acid in position 14 is the C-terminal portion, —NH—*CH(CH$_2$R$_5$)—R$_6$, of the polypeptide, may have the L or D configuration, and may be selected from the group consisting of glutamine, lysine, ornithine, 2,4-diaminobutyric acid, arginine, and homoarginine, and preferably is selected from the group consisting of L-lysine, D-lysine, L-glutamine, and D-glutamine.

When the polypeptide of the present invention is larger than tetradecapeptide, the amino acid in position 14 of the polypeptide is L-glutamine.

Position 15

When the polypeptide in the present invention is a pentadecapeptide, the amino acid in position 15 is the C-terminal portion, —NH—*CH(CH$_2$R$_5$)—R$_6$, of the polypeptide, may have the L or D configuration, and may be selected from the group consisting of lysine, ornithine, 2,4-diaminobutyric acid, arginine, and homoarginine, preferably L-lysine or D-lysine.

When the polypeptide of the present invention is larger than a pentadecapeptide, the amino acid in position 15 is L-glutamic acid.

Position 16

When the polypeptide in the present invention is a hexadecapeptide, the amino acid in position 16 is the C-terminal portion, —NH—*CH(CH$_2$R$_5$)—R$_6$, of the polypeptide, may have the L or D configuration, and may be selected from the group consisting of lysine, ornithine, 2,4-diaminobutyric acid, arginine, and homoarginine, preferably L-lysine or D-lysine.

When the polypeptide of the present invention is larger than hexadecapeptide, the amino acid in position 16 of the polypeptide is L-lysine.

Position 17

When the polypeptide in the present invention is a heptadecapeptide, the amino acid in position 17 is the C-terminal portion, —NH—* CH(CH$_2$R$_5$)—R$_6$, of the polypeptide, may have the L or D configuration, and may be selected from the group consisting of lysine, ornithine, 2,4-diaminobutyric acid, arginine, and homoarginine, preferably L-lysine or D-lysine.

When the polypeptide of the present invention is larger than a heptadecapeptide, the amino acid in position 17 is L-glutamic acid.

Position 18

When the polypeptide in the present invention is an octadecapeptide, the amino acid in position 18 is the C-terminal portion, —NH—* CH(CH$_2$R$_5$)—R$_6$, of the polypeptide, may have the L or D configuration, and may be selected from the group consisting of lysine, ornithine, 2,4-diaminobutyric acid, arginine, and homoarginine, and preferably is selected from the group consisting of L-lysine, D-lysine, L-arginine, and D-arginine.

When the polypeptide of the present invention is larger than octadecapeptide, the amino acid in position 18 of the polypeptide is L-arginine.

Position 19

When the polypeptide in the present invention is a nonadecapeptide, the amino acid in position 19 is the C-terminal portion, —NH—*CH(CH$_2$R$_5$)—R$_6$, of the polypeptide, may have the L or D configuration, and may be selected from the group consisting of lysine, ornithine, 2,4-diaminobutyric acid, arginine, and homoarginine, preferably L-lysine or D-lysine.

When the polypeptide of the present invention is larger than a nonadecapeptide, the amino acid in position 19 is L-asparagine.

Position 20

When the polypeptide in the present invention consists of 20 amino acids, the amino acid in position 20 is the C-terminal portion, —NH—* CH(CH$_2$R$_5$)—R$_6$, of the polypeptide, may have the L or D configuration, and may be selected from the group consisting of lysine, ornithine, 2,4-diaminobutyfic acid, arginine, and homoarginine, preferably L-lysine or D-lysine.

When the polypeptide of the present invention is larger than 20 amino acids, the amino acid in position 20 of the polypeptide is L-lysine.

Position 21

When the polypeptide in the present invention consists of 21 amino acids, the amino acid in position 21 is the C-terminal portion, —NH—*CH(CH$_2$R$_5$)—R$_6$, of the polypeptide, may have the L or D configuration, and may be selected from the group consisting of lysine, ornithine, 2,4-diaminobutyric acid, arginine, and homoarginine, preferably L-lysine or D-lysine.

When the polypeptide of the present invention is larger than 21 amino acids, the amino acid in position 21 is glycine.

Position 22

The amino acid in position 22 of certain of the polypeptides of this invention is the C-terminal portion, —NH—*CH(CH$_2$R$_5$)—R$_6$, of the polypeptide, may have the L or D configuration, and may be selected from the group consisting of glutamine, lysine, ornithine, 2,4-diaminobutyric acid, arginine, and homoarginine, and preferably is selected from the group consisting of L-lysine, D-lysine, L-glutamine, and D-glutamine.

The C-terminal amino acid, —NH—*CH(CH$_2$R$_5$)R$_6$

The residue present in the C-terminal position, —NH—*CH(CH$_2$R$_5$)—R$_6$, of the polypeptides of this invention is an amino acid with a C-terminal carboxylic acid derivative R$_6$, wherein R$_6$ is —COOH or —CONH$_2$, preferably —CONH$_2$. R$_5$ is as defined above.

The term "cycloalkyl", as used herein, means cyclic hydrocarbon radicals containing from 5 to 7 carbon atoms. Examples of suitable cyclic-hydrocarbon radicals are cyclopentyl, cyclohexyl, and cycloheptyl. The term "halogen", as used herein, includes all four halogens with chlorine being preferred.

In a preferred embodiment, the compounds of the present invention are selected from the group consisting of:

H-Phe-Val-Pro-Ile-Phe-Thr-Tyr-Gly-Glu-Leu-Gln-D-Arg-Leu-Gln-Lys-Glu-Arg-Asn-Lys-Gly-Gln-OH (SEQ ID NO:9);

H-Phe-Val-Pro-Ile-Phe-Thr-Tyr-Gly-Glu-Leu-Gln-D-Arg-Leu-Gln-Lys-Glu-Arg-Asn-Lys-Gly-Gln-NH$_2$ (SEQ ID NO:10);

H-Phe-Val-Ala-Ile-Phe-Thr-Tyr-Gly-Glu-Leu-Gln-D-Arg-Leu-Gln-Lys-Glu-Arg-Asn-Lys-Gly-Gln-OH (SEQ ID NO:11);

H-Phe-Val-Ala-Ile-Phe-Thr-Tyr-Gly-Glu-Leu-Gln-D-Arg-Leu-Gln-Lys-Glu-Arg-Asn-Lys-Gly-Gln-NH$_2$ (SEQ ID NO:12);

H-Phe-Val-Pro-Ile-Phe-Thr-Tyr-Gly-Glu-Leu-Gln-D-Arg-NH$_2$ (SEQ ID NO:13);

H-Phe-Val-Pro-Ile-Phe-Thr-Tyr-Gly-Glu-Leu-Gln-D-Arg-Leu-Gln-OH (SEQ ID NO:14);

(N-Me)-Phe-Val-Pro-Ile-Phe-Thr-Tyr-Gly-Glu-Leu-Gln-D-Arg-Leu-Gln-OH (SEQ ID NO:15);

H-Phe-Val-Pro-Ile-Phe-Thr-Tyr-Gly-Glu-Leu-Gln-D-h-Arg-Leu-Gln-OH (SEQ ID NO:16);

H-Phe-Val-Pro-Ile-Phe-Thr-Tyr-Gly-Glu-Leu-Gln-D-Lys-Leu-Gln-OH (SEQ ID NO:17);

H-Phe-Val-Pro-Ile-Phe-Thr-Tyr-Gly-Glu-Leu-Gln-D-Orn-Leu-Gln-OH (SEQ ID NO:18);

H-Phe-Val-Pro-Ile-Phe-Thr-Tyr-Gly-Glu-Leu-Gln-D-Dab-Leu-Gln-OH (SEQ ID NO:19);

H-Phe-Val-Pro-Ile-Phe-Thr-Tyr-Gly-Glu-Leu-Gln-D-Gln-Leu-Gln-OH (SEQ ID NO:20);

H-Phe-Val-Pro-Ile-Phe-Thr-Tyr-Gly-Glu-Leu-Gln-D-Ala-Leu-Gln-OH (SEQ ID NO:21);

H-Phe-Val-Ala-Ile-Phe-Thr-Tyr-Gly-Glu-Leu-Gln-D-Arg-Leu-Gln-OH (SEQ ID NO:22);

H-Phe-Val-Pro-Leu-Phe-Thr-Tyr-Gly-Glu-Leu-Gln-D-Arg-Leu-Gln-OH (SEQ ID NO:23);

H-Phe-Val-Pro-Ile-Cha-Thr-Tyr-Gly-Glu-Leu-Gln-D-Arg-Leu-Gln-OH (SEQ ID NO:24);

H-Phe-Val-Pro-Ile-Phe-Thr-Phe-Gly-Glu-Leu-Gln-D-Arg-Leu-Gln-OH (SEQ ID NO:25);

H-Phe-Val-Pro-Ile-Phe-Thr-Tyr-D-Ala-Glu-Leu-Gln-D-Arg-Leu-Gln-OH (SEQ ID NO:26);

H-Phe-Val-Pro-Ile-Phe-Thr-Tyr-Gly-Glu-Leu-Ala-D-Arg-Leu-Gln-OH (SEQ ID NO:27);

H-Phe-Leu-Pro-Ile-Phe-Thr-Tyr-Gly-Glu-Leu-Gln-D-Arg-Leu-Gln-OH (SEQ ID NO:28);

H-Phe-Val-Pro-Ile-Phe-Thr-Tyr-Gly-Glu-Leu-Gln-D-Arg-Leu-Gln-NH$_2$ (SEQ ID NO:29);

(N-He)-Phe-Val-Pro-Ile-Phe-Thr-Tyr-Gly-Glu-Leu-Gln-D-Arg-Leu-Gln-NH$_2$ (SEQ ID NO:30);

(Me$_2$N)-Phe-Val-Pro-Ile-Phe-Thr-Tyr-Gly-Glu-Leu-Gln-D-Arg-Leu-Gln-NH$_2$ (SEQ ID NO:31);

(Me$_3$N$^+$)-Phe-Val-Pro-Ile-Phe-Thr-Tyr-Gly-Glu-Leu-Gln-D-Arg-Leu-Gln-NH$_2$ (SEQ ID NO:32);

H-Phe-Val-Pro-Ile-Phe-Thr-Tyr-Gly-Glu-Leu-Gln-D-h-Arg-Leu-Gln-NH$_2$ (SEQ ID NO:33);

H-Phe-Val-Pro-Ile-Phe-Thr-Tyr-Gly-Glu-Leu-Gln-D-Lys-Leu-Gln-NH$_2$ (SEQ ID NO:34);

H-Phe-Val-Pro-Ile-Phe-Thr-Tyr-Gly-Glu-Leu-Gln-D-Orn-Leu-Gln-NH$_2$ (SEQ ID NO:35);

H-Phe-Val-Pro-Ile-Phe-Thr-Tyr-Gly-Glu-Leu-Gln-D-Dab-Leu-Gln-NH$_2$ (SEQ ID NO:36);

H-Phe-Val-Pro-Ile-Phe-Thr-Tyr-Gly-Glu-Leu-Gln-D-Gln-Leu-Gln-NH$_2$ (SEQ ID NO:37);

H-Phe-Val-Pro-Ile-Phe-Thr-Tyr-Gly-Glu-Leu-Gln-D-Ala-Leu-Gln-NH₂ (SEQ ID NO:38);

H-Phe-Val-Ala-Phe-Thr-Tyr-Gly-Glu-Leu-Gln-D-Arg-Leu-Gln-NH₂ (SEQ ID NO:39);

H-Phe-Val-Pro-Leu-Phe-Thr-Tyr-Gly-Glu-Leu-Gln-D-Arg-Leu-Gln-NH₂ (SEQ ID NO:40);

H-Phe-Val-Pro-Ile-Cha-Thr-Tyr-Gly-Glu-Leu-Gln-D-Arg-Leu-Gln-NH₂ (SEQ ID NO:41);

H-Phe-Val-Pro-Ile-Phe-Thr-Phe-Gly-Glu-Leu-Gln-D-Arg-Leu-Gln-NH₂ (SEQ ID NO:42);

H-Phe-Val-Pro-Ile-Phe-Thr-Tyr-D-Ala-Glu-Leu-Gln-D-Arg-Leu-Gln-NH₂ (SEQ ID NO:43);

H-Phe-Val-Pro-Ile-Phe-Thr-Tyr-Gly-Glu-Leu-Ala-D-Arg-Leu-Gln-NH₂ (SEQ ID NO:44);

H-Phe-Leu-Pro-Ile-Phe-Thr-Tyr-Gly-Glu-Leu-Gln-D-Arg-Leu-Gln-NH₂ (SEQ ID NO:45);

H-Phe-Val-Pro-Ile-Phe-Thr-Tyr-Gly-Glu-Leu-Gln-D-Arg-Leu-Lys-NH₂ (SEQ ID NO:46);

H-D-Phe-Val-Pro-Ile-Phe-Thr-Tyr-Gly-Glu-Leu-Gln-D-Arg-Leu-Gln-OH (SEQ ID NO:47);

H-Cha-Val-Pro-Ile-Phe-Thr-Tyr-Gly-Glu-Leu-Gln-D-Arg-Leu-Gln-OH (SEQ ID NO:48);

H-Phe-Val-Pro-Ile-Phe-Thr-Tyr-Gly-Glu-Leu-Gln-D-Asn-Leu-Gln-OH (SEQ ID NO:49);

H-D-Phe-Val-Pro-Ile-Phe-Thr-Tyr-Gly-Glu-Leu-Gln-D-Arg-Leu-Gln-NH₂ (SEQ ID NO:50);

H-Cha-Val-Pro-Ile-Phe-Thr-Tyr-Gly-Glu-Leu-Gln-D-Arg-Leu-Gln-NH₂ (SEQ ID NO:51);

H-Phe-Val-Pro-Ile-Phe-Thr-Tyr-Gly-Glu-Leu-Gln-D-Asn-Leu-Gln-NH₂ (SEQ ID NO:52);

H-Phe-Val-Pro-Ile-Phe-Thr-Tyr-Gly-Glu-Leu-Gln-D-Arg-Leu-D-Gln-NH₂ (SEQ ID NO:53);

H-Phe-Val-Ala-Ile-Phe-Thr-Tyr-Gly-Glu-Leu-Gln-D-Arg-NH₂ (SEQ ID NO:54);

H-Phe-Val-Ala-Ile-Phe-Thr-Tyr-Gly-Glu-Leu-Gln-D-Arg-Leu-Gln-OH (SEQ ID NO:55);

(N-Me)-Phe-Val-Ala-Ile-Phe-Thr-Tyr-Gly-Glu-Leu-Gln-D-Arg-Leu-Gln-OH (SEQ ID NO:56);

(Me₂N)-Phe-Val-Ala-Ile-Phe-Thr-Tyr-Gly-Glu-Leu-Gln-D-Arg-Leu-Gln-OH (SEQ ID NO:57);

(Me₃N⁺)-Phe-Val-Ala-Ile-Phe-Thr-Tyr-Gly-Glu-Leu-Gln-D-Arg-Leu-Gln-OH (SEQ ID NO:58);

H-Phe-Val-Ala-Leu-Phe-Thr-Tyr-Gly-Glu-Leu-Gln-D-Arg-Leu-Gln-OH (SEQ ID NO:59);

H-Phe-Val-Ala-Ile-Cha-Thr-Tyr-Gly-Glu-Leu-Gln-D-Arg-Leu-Gln-OH (SEQ ID NO:60);

H-Phe-Val-Ala-Ile-Phe-Thr-Phe-Gly-Glu-Leu-Gln-D-Arg-Leu-Gln-OH (SEQ ID NO:61);

H-Phe-Val-Ala-Ile-Phe-Thr-Tyr-D-Ala-Glu-Leu-Gln-D-Arg-Leu-Gln-OH (SEQ ID NO:62);

H-Phe-Val-Ala-Ile-Phe-Thr-Tyr-Gly-Glu-Leu-Ala-D-Arg-Leu-Gln-OH (SEQ ID NO:63);

H-Phe-Leu-Ala-Ile-Phe-Thr-Tyr-Gly-Glu-Leu-Gln-D-Arg-Leu-Gln-OH (SEQ ID NO:64);

H-Phe-Val-Ala-Ile-Phe-Thr-Tyr-Gly-Glu-Leu-Gln-D-Arg-Leu-Gln-NH₂ (SEQ ID NO:65);

(N-Me)-Phe-Val-Ala-Ile-Phe-Thr-Tyr-Gly-Glu-Leu-Gln-D-Arg-Leu-Gln-NH₂ (SEQ ID NO:66);

(Me₂N)-Phe-Val-Ala-Ile-Phe-Thr-Tyr-Gly-Glu-Leu-Gln-D-Arg-Leu-Gln-NH₂ (SEQ ID NO:67);

(Me₃N⁺)-Phe-Val-Ala-Ile-Phe-Thr-Tyr-Gly-Glu-Leu-Gln-D-Arg-Leu-Gln-NH₂ (SEQ ID NO:68);

H-Phe-Val-Ala-Leu-Phe-Thr-Tyr-Gly-Glu-Leu-Gln-D-Arg-Leu-Gln-NH₂ (SEQ ID NO:69);

H-Phe-Val-Ala-Ile-Cha-Thr-Tyr-Gly-Glu-Leu-Gln-D-Arg-Leu-Gln-NH₂ (SEQ ID NO:70);

H-Phe-Val-Ala-Ile-Phe-Thr-Phe-Gly-Glu-Leu-Gln-D-Arg-Leu-Gln-NH₂ (SEQ ID NO:71);

H-Phe-Val-Ala-Ile-Phe-Thr-Tyr-D-Ala-Glu-Leu-Gln-D-Arg-Leu-Gln-NH₂ (SEQ ID NO:72);

H-Phe-Val-Ala-Ile-Phe-Thr-Tyr-Gly-Glu-Leu-Ala-D-Arg-Leu-Gln-NH₂ (SEQ ID NO:73);

H-Phe-Leu-Ala-Ile-Phe-Thr-Tyr-Gly-Glu-Leu-Gln-D-Arg-Leu-Gln-NH₂ (SEQ ID NO:74);

H-Phe-Val-Ala-Ile-Phe-Thr-Tyr-Gly-Glu-Leu-Gln-D-Arg-Leu-Lys-NH₂ (SEQ ID NO:75);

H-D-Phe-Val-Ala-Ile-Phe-Thr-Tyr-Gly-Glu-Leu-Gln-D-Arg-Leu-Gln-OH (SEQ ID NO:76);

H-Cha-Val-Ala-Ile-Phe-Thr-Tyr-Gly-Glu-Leu-Gln-D-Arg-Leu-Gln-OH (SEQ ID NO:77);

H-Phe-Val-Pal-Ile-Phe-Thr-Tyr-Gly-Glu-Leu-Gln-Arg-Leu-Gln-OH (SEQ ID NO:78);

H-D-Phe-Val-Ala-Ile-Phe-Thr-Tyr-Gly-Glu-Leu-Gln-D-Arg-Leu-Gln-NH₂ (SEQ ID NO:79);

H-Cha-Val-Ala-Ile-Phe-Thr-Tyr-Gly-Glu-Leu-Gln-D-Arg-Leu-Gln-NH₂ (SEQ ID NO:80);

H-Phe-Val-Pal-Ile-Phe-Thr-Tyr-Gly-Glu-Leu-Gln-Arg-Leu-Gln-NH₂ (SEQ ID NO:81);

H-Phe-Val-Ala-Ile-Phe-Thr-Tyr-Gly-Glu-Leu-Gln-D-Arg-Leu-D-Gln-NH₂ (SEQ ID NO:82);

(N-Me)-Phe-Val-Ala-Ile-Phe-Thr-Tyr-Gly-Glu-Leu-Gln-D-Arg-Leu-D-Gln-NH₂ (SEQ ID NO:83);

(Me₂N)-Phe-Val-Ala-Ile-Phe-Thr-Tyr-Gly-Glu-Leu-Gln-D-Arg-Leu-D-Gln-NH₂ (SEQ ID NO:84);

(Me₃N⁺)-Phe-Val-Ala-Ile-Phe-Thr-Tyr-Gly-Glu-Leu-Gln-D-Arg-Leu-D-Gln-NH₂ (SEQ ID NO:85);

(N-Me)-Phe-Val-Pro-Ile-Phe-Thr-Tyr-Gly-Glu-Leu-Gln-D-Arg-Leu-D-Gln-NH₂ (SEQ ID NO:86);

(Me₂N)-Phe-Val-Pro-Ile-Phe-Thr-Tyr-Gly-Glu-Leu-Gln-D-Arg-Leu-D-Gln-NH₂ (SEQ ID NO:87);

(Me₃N⁺)-Phe-Val-Pro-Ile-Phe-Thr-Tyr-Gly-Glu-Leu-Gln-D-Arg-Leu-D-Gln-NH₂ (SEQ ID NO:88);

(N-Me)-Phe-Val-Ala-Ile-Phe-Thr-Tyr-Gly-Glu-Leu-Gln-D-Arg-Leu-Lys-NH₂ (SEQ ID NO:147);

(Me₂N)-Phe-Val-Ala-Ile-Phe-Thr-Tyr-Gly-Glu-Leu-Gln-D-Arg-Leu-Lys-NH₂ (SEQ ID NO:89);

(Me₃N⁺)-Phe-Val-Ala-Ile-Phe-Thr-Tyr-Gly-Glu-Leu-Gln-D-Arg-Leu-Lys-NH₂ (SEQ ID NO:90);

(N-Me)-Phe-Val-Pro-Ile-Phe-Thr-Tyr-Gly-Glu-Leu-Gln-D-Arg-Leu-Lys-NH₂ (SEQ ID NO:91);

(Me₂N)-Phe-Val-Pro-Ile-Phe-Thr-Tyr-Gly-Glu-Leu-Gln-D-Arg-Leu-Lys-NH₂ (SEQ ID NO:92);

(Me₃N⁺)-Phe-Val-Pro-Ile-Phe-Thr-Tyr-Gly-Glu-Leu-Gln-D-Arg-Leu-Lys-NH₂ (SEQ ID NO:93);

(N-Me)-Phe-Val-Ala-Ile-Phe-Thr-Tyr-Gly-Glu-Leu-Gln-D-Arg-Leu-D-Lys-NH₂ (SEQ ID NO:94);

(Me₂N)-Phe-Val-Ala-Ile-Phe-Thr-Tyr-Gly-Glu-Leu-Gln-D-Arg-Leu-D-Lys-NH₂ (SEQ ID NO:95);

(Me₃N⁺)-Phe-Val-Ala-Ile-Phe-Thr-Tyr-Gly-Glu-Leu-Gln-D-Arg-Leu-D-Lys-NH₂ (SEQ ID NO:96);

(N-Me)-Phe-Val-Pro-Ile-Phe-Thr-Tyr-Gly-Glu-Leu-Gln-D-Arg-Leu-D-Lys-NH₂ (SEQ ID NO:97);

(Me₂N)-Phe-Val-Pro-Ile-Phe-Thr-Tyr-Gly-Glu-Leu-Gln-D-Arg-Leu-D-Lys-NH₂ (SEQ ID NO:98);

(Me₃N⁺)-Phe-Val-Pro-Ile-Phe-Thr-Tyr-Gly-Glu-Leu-Gln-D-Arg-Leu-D-Lys-NH₂ (SEQ ID NO:99);

(N-Me)-Phe-Val-Ala-Ile-Phe-Thr-Tyr-Gly-Glu-Leu-Ala-D-Arg-Leu-Gln-NH₂ (SEQ ID NO:100);

(Me₂N)-Phe-Val-Ala-Ile-Phe-Thr-Tyr-Gly-Glu-Leu-Ala-D-Arg-Leu-Gln-NH₂ (SEQ ID NO:101);

(Me₃N⁺)-Phe-Val-Ala-Ile-Phe-Thr-Tyr-Gly-Glu-Leu-Ala-D-Arg-Leu-Gln-NH₂ (SEQ ID NO:102);

(N-Me)-Phe-Val-Pro-Ile-Phe-Thr-Tyr-Gly-Glu-Leu-Ala-D-Arg-Leu-Gln-NH₂ (SEQ ID NO:103);

(Me₂N)-Phe-Val-Pro-Ile-Phe-Thr-Tyr-Gly-Glu-Leu-Ala-D-Arg-Leu-Gln-NH₂ (SEQ ID NO:104);

(Me₃N+)-Phe-Val-Pro-Ile-Phe-Thr-Tyr-Gly-Glu-Leu-Ala-D-Arg-Leu-Gln-NH₂ (SEQ ID NO:105);

(N-Me)-Phe-Val-Ala-Ile-Phe-Thr-Tyr-Gly-Glu-Leu-Ala-D-Arg-Leu-D-Gln-NH₂ (SEQ ID NO:106);

(Me₂N)-Phe-Val-Ala-Ile-Phe-Thr-Tyr-Gly-Glu-Leu-Ala-D-Arg-Leu-D-Gln-NH₂ (SEQ ID NO:107);

(Me₃N+)-Phe-Val-Ala-Ile-Phe-Thr-Tyr-Gly-Glu-Leu-Ala-D-Arg-Leu-D-Gln-NH₂ (SEQ ID NO:108);

(N-Me)-Phe-Val-Pro-Ile-Phe-Thr-Tyr-Gly-Glu-Leu-Ala-D-Arg-Leu-D-Gln-NH₂ (SEQ ID NO:109);

(Me₂N)-Phe-Val-Pro-Ile-Phe-Thr-Tyr-Gly-Glu-Leu-Ala-D-Arg-Leu-D-Gln-NH₂ (SEQ ID NO:110);

(Me₃N+)-Phe-Val-Pro-Ile-Phe-Thr-Tyr-Gly-Glu-Leu-Ala-D-Arg-Leu-D-Gln-NH₂ (SEQ ID NO:111);

(N-Me)-Phe-Val-Ala-Ile-Phe-Thr-Tyr-Gly-Glu-Leu-Ala-D-Arg-Leu-Lys-NH₂ (SEQ ID NO:112);

(Me₂N)-Phe-Val-Ala-Ile-Phe-Thr-Tyr-Gly-Glu-Leu-Ala-D-Arg-Leu-Lys-NH₂ (SEQ ID NO:113);

(Me₃N+)-Phe-Val-Ala-Ile-Phe-Thr-Tyr-Gly-Glu-Leu-Ala-D-Arg-Leu-Lys-NH₂ (SEQ ID NO:114);

(N-Me)-Phe-Val-Pro-Ile-Phe-Thr-Tyr-Gly-Glu-Leu-Ala-D-Arg-Leu-Lys-NH₂ (SEQ ID NO:115);

(Me₂N)-Phe-Val-Pro-Ile-Phe-Thr-Tyr-Gly-Glu-Leu-Ala-D-Arg-Leu-Lys-NH₂ (SEQ ID NO:116);

(Me₃N+)-Phe-Val-Pro-Ile-Phe-Thr-Tyr-Gly-Glu-Leu-Ala-D-Arg-Leu-Lys-NH₂ (SEQ ID NO:117);

(N-Me)-Phe-Val-Ala-Ile-Phe-Thr-Tyr-Gly-Glu-Leu-Ala-D-Arg-Leu-D-Lys-NH₂ (SEQ ID NO:118);

(Me₂N)-Phe-Val-Ala-Ile-Phe-Thr-Tyr-Gly-Glu-Leu-Ala-D-Arg-Leu-D-Lys-NH₂ (SEQ ID NO:119);

(Me₃N+)-Phe-Val-Ala-Ile-Phe-Thr-Tyr-Gly-Glu-Leu-Ala-D-Arg-Leu-D-Lys-NH₂ (SEQ ID NO:120);

(N-Me)-Phe-Val-Pro-Ile-Phe-Thr-Tyr-Gly-Glu-Leu-Ala-D-Arg-Leu-D-Lys-NH₂ (SEQ ID NO:121);

(Me₂N)-Phe-Val-Pro-Ile-Phe-Thr-Tyr-Gly-Glu-Leu-Ala-D-Arg-Leu-D-Lys-NH₂ (SEQ ID NO:122);

(Me3N+)-Phe-Val-Pro-Ile-Phe-Thr-Tyr-Gly-Glu-Leu-Ala-D-Arg-Leu-D-Lys-NH₂ (SEQ ID NO:123);

(N-Me)-Phe-Val-Ala-Ile-Phe-Thr-Tyr-Gly-Glu-Leu-Gln-D-Arg-NH₂ (SEQ ID NO:124);

(Me₂N)-Phe-Val-Ala-Ile-Phe-Thr-Tyr-Gly-Glu-Leu-Gln-D-Arg-NH₂ (SEQ ID NO:125);

(Me₃N+)-Phe-Val-Ala-Ile-Phe-Thr-Tyr-Gly-Glu-Leu-Gln-D-Arg-NH₂ (SEQ ID NO:126);

(N-Me)-Phe-Val-Pro-Ile-Phe-Thr-Tyr-Gly-Glu-Leu-Gln-D-Arg-NH₂ (SEQ ID NO:127);

(Me₂N)-Phe-Val-Pro-Ile-Phe-Thr-Tyr-Gly-Glu-Leu-Gln-D-Arg-NH₂ (SEQ ID NO:128);

(Me₃N+)-Phe-Val-Pro-Ile-Phe-Thr-Tyr-Gly-Glu-Leu-Gln-D-Arg-NH₂ (SEQ ID NO:129);

(N-Me)-Phe-Val-Pro-Ile-Phe-Thr-Tyr-Gly-Glu-Leu-Ala-D-Arg-NH₂ (SEQ ID NO:130);

(Me₂N)-Phe-Val-Pro-Ile-Phe-Thr-Tyr-Gly-Glu-Leu-Ala-D-Arg-NH₂ (SEQ ID NO:131);

(Me₃N+)-Phe-Val-Pro-Ile-Phe-Thr-Tyr-Gly-Glu-Leu-Ala-D-Arg-NH₂ (SEQ ID NO:132);

D-Cha-Val-Ala-Ile-Phe-Thr-Tyr-Gly-Glu-Leu-Ala-D-Arg-Leu-D-Lys-NH₂ (SEQ ID NO:133);

(N-Me)-Phe-Val-Pro-Ile-Phe-Thr-Tyr-Gly-Glu-Leu-Gln-Arg-NH₂ (SEQ ID NO:134);

(Me₂N)-Phe-Val-Pro-Ile-Phe-Thr-Tyr-Gly-Glu-Leu-Gln-Arg-NH₂ (SEQ ID NO:135);

(Me₃N+)-Phe-Val-Pro-Ile-Phe-Thr-Tyr-Gly-Glu-Leu-Gln-Arg-NH₂ (SEQ ID NO:136);

(N-Me)-Phe-Val-Pro-Ile-Phe-Thr-Tyr-Gly-Glu-Leu-Gln-D-Arg-NH₂ (SEQ ID NO:137);

(Me₂N)-Phe-Val-Pro-Ile-Phe-Thr-Tyr-Gly-Glu-Leu-Gln-D-Arg-NH₂ (SEQ ID NO:138);

(Me₃N+)-Phe-Val-Pro-Ile-Phe-Thr-Tyr-Gly-Glu-Leu-Gln-D-Arg-NH₂ (SEQ ID NO:139);

(N-Me)-Phe-Val-Ala-Ile-Phe-Thr-Tyr-Gly-Glu-Leu-Gln-Arg-NH₂ (SEQ ID NO:140);

(Me₂N)-Phe-Val-Ala-Ile-Phe-Thr-Tyr-Gly-Glu-Leu-Gln-Arg-NH₂ (SEQ ID NO:141);

(Me₃N+)-Phe-Val-Ala-Ile-Phe-Thr-Tyr-Gly-Glu-Leu-Gln-Arg-NH₂ (SEQ ID NO:142);

(N-Me)-Phe-Val-Ala-Ile-Phe-Thr-Tyr-Gly-Glu-Leu-Gln-D-Arg-NH₂ (SEQ ID NO:143);

(Me₂N)-Phe-Val-Ala-Ile-Phe-Thr-Tyr-Gly-Glu-Leu-Gln-D-Arg-NH₂ (SEQ ID NO:144);

(Me₃N+)-Phe-Val-Ala-Ile-Phe-Thr-Tyr-Gly-Glu-Leu-Gln-D-Arg-NH₂ (SEQ ID NO:145);

(N-Me)-Phe-Val-Ala-Ile-Phe-Thr-Tyr-Gly-Glu-Leu-Ala-Arg-NH₂ (SEQ ID NO:146);

(Me₂N)-Phe-Val-Ala-Ile-Phe-Thr-Tyr-Gly-Glu-Leu-Ala-Arg-NH₂ (SEQ ID NO:148);

(Me₃N+)-Phe-Val-Ala-Ile-Phe-Thr-Tyr-Gly-Glu-Leu-Ala-Arg-NH₂ (SEQ ID NO:149);

(N-Me)-Phe-Val-Pro-Ile-Phe-Thr-Tyr-Gly-Glu-Leu-Gln-Arg-Leu-Lys-NH₂ (SEQ ID NO:150);

(Me₂N)-Phe-Val-Pro-Ile-Phe-Thr-Tyr-Gly-Glu-Leu-Gln-Arg-Leu-Lys-NH₂ (SEQ ID NO:151);

(Me₃N+)-Phe-Val-Pro-Ile-Phe-Thr-Tyr-Gly-Glu-Leu-Gln-Arg-Leu-Lys-NH₂ (SEQ ID NO:152);

(N-Me)-Phe-Val-Ala-Ile-Phe-Thr-Tyr-Gly-Glu-Leu-Gln-Arg-Leu-Lys-NH₂ (SEQ ID NO:153);

(Me₂N)-Phe-Val-Ala-[Le-Phe-Thr-Tyr-Gly-Glu-Leu-Gln-Arg-Leu-Lys-NH₂ (SEQ ID NO:154);

(Me₃N+)-Phe-Val-Ala-Ile-Phe-Thr-Tyr-Gly-Glu-Leu-Gln-Arg-Leu-Lys-NH₂ (SEQ ID NO:155);

(N-Me)-Phe-Val-Pro-Ile-Phe-Thr-Tyr-Gly-Glu-Leu-Ala-Arg-Leu-Lys-NH₂ (SEQ ID NO:156);

(Me₂N)-Phe-Val-Pro-Ile-Phe-Thr-Tyr-Gly-Glu-Leu-Ala-Arg-Leu-Lys-NH₂ (SEQ ID NO:157);

(Me₃N+)-Phe-Val-Pro-Ile-Phe-Thr-Tyr-Gly-Glu-Leu-Ala-Arg-Leu-Lys-NH₂ (SEQ ID NO:158);

(N-Me)-Phe-Val-Ala-Ile-Phe-Thr-Tyr-Gly-Glu-Leu-Ala-Arg-Leu-Lys-NH₂ (SEQ ID NO:159);

(Me₂N)-Phe-Val-Ala-Ile-Phe-Thr-Tyr-Gly-Glu-Leu-Ala-Arg-Leu-Lys-NH₂ (SEQ ID NO:160);

(Me₃N+)-Phe-Val-Ala-Ile-Phe-Thr-Tyr-Gly-Glu-Leu-Ala-Arg-Leu-Lys-NH₂ (SEQ ID NO:161);

(N-Me)-Phe-Val-Pro-Ile-Phe-Thr-Tyr-Gly-Glu-Leu-Gln-Arg-Leu-D-Gln-NH₂ (SEQ ID NO:162);

(Me₂N)-Phe-Val-Pro-Ile-Phe-Thr-Tyr-Gly-Glu-Leu-Gln-Arg-Leu-D-Gln-NH₂ (SEQ ID NO:163);

(Me₃N+)-Phe-Val-Pro-Ile-Phe-Thr-Tyr-Gly-Glu-Leu-Gln-Arg-Leu-D-Gln-NH₂ (SEQ ID NO:164);

(N-Me)-Phe-Val-Ala-Ile-Phe-Thr-Tyr-Gly-Glu-Leu-Gln-Arg-Leu-D-Gln-NH₂ (SEQ ID NO:165);

(Me₂N)-Phe-Val-Ala-Ile-Phe-Thr-Tyr-Gly-Glu-Leu-Gln-Arg-Leu-D-Gln-NH₂ (SEQ ID NO:166);

(Me₃N+)-Phe-Val-Ala-Ile-Phe-Thr-Tyr-Gly-Glu-Leu-Gln-Arg-Leu-D-Gln-NH₂ (SEQ ID NO:167);

(N-Me)-Phe-Val-Pro-Ile-Phe-Thr-Tyr-Gly-Glu-Leu-Ala-Arg-Leu-D-Gln-NH₂ (SEQ ID NO:168);

(Me₂N)-Phe-Val-Pro-Ile-Phe-Thr-Tyr-Gly-Glu-Leu-Ala-Arg-Leu-D-Gln-NH₂ (SEQ ID NO:169);

(Me₃N+)-Phe-Val-Pro-Ile-Phe-Thr-Tyr-Gly-Glu-Leu-Ala-Arg-Leu-D-Gln-NH₂ (SEQ ID NO:170);

(N-Me)-Phe-Val-Ala-Ile-Phe-Thr-Tyr-Gly-Glu-Leu-Ala-Arg-Leu-D-Gln-NH₂ (SEQ ID NO:171);

(Me₂N)-Phe-Val-Ala-Ile-Phe-Thr-Tyr-Gly-Glu-Leu-Ala-Arg-Leu-D-Gln-NH₂ (SEQ ID NO:172); and (Me₃N+)-Phe-Val-Ala-Ile-Phe-Thr-Tyr-Gly-Glu-Leu-Ala-Arg-Leu-D-Gln-NH₂ (SEQ ID NO:173), and their pharmaceutically acceptable addition salts. In each case, the amino acids have the L-configuration unless otherwise specified. In a more preferred embodiment, the compounds of the present invention are selected from the group consisting of (N-Me)-Phe-Val-Pro-Ile-Phe-Thr-Tyr-Gly-Glu-Leu-Gln-D-Arg-Leu-Gln-OH (SEQ ID NO:15);
(N-Me)-Phe-Val-Pro-Ile-Phe-Thr-Tyr-Gly-Glu-Leu-Gln-D-Arg-Leu-Gln-NH$_2$ (SEQ ID NO:30);
(Me$_2$N)-Phe-Val-Pro-Ile-Phe-Thr-Tyr-Gly-Glu-Leu-Gln-D-Arg-Leu-Gln-NH$_2$ (SEQ ID NO:31);
(Me$_3$N$^+$)-Phe-Val-Pro-Ile-Phe-Thr-Tyr-Gly-Glu-Leu-Gln-D-Arg-Leu-Gln-NH$_2$ (SEQ ID NO:32);
(N-Me)-Phe -Val-Ala-Ile-Phe-Thr-Tyr-Gly-Glu-Leu-Gln-D-Arg-Leu-Gln-OH (SEQ ID NO:56);
(Me$_2$N)-Phe-Val-Ala-Ile-Phe-Thr-Tyr-Gly-Glu-Leu-Gln-D-Arg-Leu-Gln-OH (SEQ ID NO:57);
(Me$_3$N$^+$)-Phe-Val-Ala-Ile-Phe-Thr-Tyr-Gly-Glu-Leu-Gln-D-Arg-Leu-Gln-OH (SEQ ID NO:58);
(N-Me)-Phe-Val-Ala-Ile-Phe-Thr-Tyr-Gly-Glu-Leu-Gln-D-Arg-Leu-Gln-NH$_2$ (SEQ ID NO:66);
(Me$_2$N)-Phe-Val-Ala-Ile-Phe-Thr-Tyr-Gly-Glu-Leu-Gln-D-Arg-Leu-Gln-NH$_2$ (SEQ ID NO:67);
(Me$_3$N$^+$)-Phe-Val-Ala-Ile-Phe-Thr-Tyr-Gly-Glu-Leu-Gln-D-Arg-Leu-Gln-NH$_2$ (SEQ ID NO:68);
(N-Me)-Phe-Val-Ala-Ile-Phe-Thr-Tyr-Gly-Glu-Leu-Gln-D-Arg-Leu-D-Gln-NH$_2$ (SEQ ID NO:83);
(Me$_2$N )-Phe-Val-Ala-Ile-Phe-Thr-Tyr-Gly-Glu-Leu-Gln-D-Arg-Leu-D-Gln-NH$_2$ (SEQ ID NO:84);
(Me$_3$N$^+$)-Phe-Val-Ala-Ile-Phe-Thr-Tyr-Gly-Glu-Leu-Gln-D-Arg-Leu-D-Gln-NH$_2$ (SEQ ID NO:85);
(N-Me)-Phe-Val-Pro-Ile-Phe-Thr-Tyr-Gly-Glu-Leu-Gln-D-Arg-Leu-D-Gln-NH$_2$ (SEQ ID NO:86);
(Me$_2$N)-Phe-Val-Pro-Ile-Phe-Thr-Tyr-Gly-Glu-Leu-Gln-D-Arg-Leu-D-Gln-NH$_2$ (SEQ ID NO:87);
(Me$_3$N$^+$)-Phe-Val-Pro-Ile-Phe-Thr-Tyr-Gly-Glu-Leu-Gln-D-Arg-Leu-D-Gln NH$_2$ (SEQ ID NO:88);
(N-Me)-Phe-Val-Ala-Ile-Phe-Thr-Tyr-Gly-Glu-Leu-Gln-D-Arg-Leu-Lys-NH$_2$ (SEQ ID NO:147);
(Me$_2$N)-Phe-Val-Ala-Ile-Phe-Thr-Tyr-Gly-Glu-Leu-Gln-D-Arg-Leu-Lys-NH$_2$ (SEQ ID NO:89);
(Me$_3$N$^+$)-Phe-Val-Ala-Ile-Phe-Thr-Tyr-Gly-Glu-Leu-Gln-D-Arg-Leu-Lys-NH$_2$ (SEQ ID NO:90);
(N-Me)-Phe-Val-Pro-Ile-Phe-Thr-Tyr-Gly-Glu-Leu-Gln-D-Arg-Leu-Lys-NH$_2$ (SEQ ID NO:91);
(Me$_2$N)-Phe-Val-Pro-Ile-Phe-Thr-Tyr-Gly-Glu-Leu-Gln-D-Arg-Leu-Lys-NH$_2$ (SEQ ID NO:92);
(Me$_3$N$^+$)-Phe-Val-Pro-Ile-Phe-Thr-Tyr-Gly-Glu-Leu-Gln-D-Arg-Leu-Lys-NH$_2$ (SEQ ID NO:93);
(N-Me)-Phe-Val-Ala-Ile-Phe-Thr-Tyr-Gly-Glu-Leu-Gln-D-Arg-Leu-D-Lys-NH$_2$ (SEQ ID NO:94);
(Me$_2$N)-Phe-Val-Ala-Ile-Phe-Thr-Tyr-Gly-Glu-Leu-Gln-D-Arg-Leu-D-Lys-NH$_2$ (SEQ ID NO:95);
(Me$_3$N)-Phe-Val-Ala-Ile-Phe-Thr-Tyr-Gly-Glu-Leu-Gln-D-Arg-Leu-D-Lys-NH$_2$ (SEQ ID NO:96);
(N-Me)-Phe-Val-Pro-Ile-Phe-Thr-Tyr-Gly-Glu-Leu-Gln-D-Arg-Leu-D-Lys-NH$_2$ (SEQ ID NO:97);
(Me$_2$N)-Phe-Val-Pro-Ile-Phe-Thr-Tyr-Gly-Glu-Leu-Gln-D-Arg-Leu-D-Lys-NH$_2$ (SEQ ID NO:98);
(Me$_3$N )-Phe-Val-Pro-Ile-Phe-Thr-Tyr-Gly-Glu-Leu-Gln-D-Arg-Leu-D-Lys-NH$_2$ (SEQ ID NO:99);
(N-Me)-Phe-Val-Ala-Ile-Phe-Thr-Tyr-Gly-Glu-Leu-Ala-D-Arg-Leu-Gln-NH$_2$ (SEQ ID NO:100);
(Me$_2$N)-Phe-Val-Ala-Ile-Phe-Thr-Tyr-Gly-Glu-Leu-Ala-D-Arg-Leu-Gln-NH$_2$ (SEQ ID NO:101);
(Me$_3$N$^+$)-Phe-Val-Ala-Ile-Phe-Thr-Tyr-Gly-Glu-Leu-Ala-D-Arg-Leu-Gln-NH$_2$ (SEQ ID NO:102);
(N-Me)-Phe-Val-Pro-Ile-Phe-Thr-Tyr-Gly-Glu-Leu-Ala-D-Arg-Leu-Gln-NH$_2$ (SEQ ID NO:103);
(Me$_2$N)-Phe-Val-Pro-Ile-Phe-Thr-Tyr-Gly-Glu-Leu-Ala-D-Arg-Leu-Gln-NH$_2$ (SEQ ID NO:104);
(Me$_3$N$^+$)-Phe-Val-Pro-Ile-Phe-Thr-Tyr-Gly-Glu-Leu-Ala-D-Arg-Leu-Gln-NH$_2$ (SEQ ID NO:105);
(N-Me)-Phe-Val-Ala-Ile-Phe-Thr-Tyr-Gly-Glu-Leu-Ala-D-Arg-Leu-D-Gln-NH$_2$ (SEQ ID NO:106);
(Me$_2$N)-Phe-Val-Ala-Ile-Phe-Thr-Tyr-Gly-Glu-Leu-Ala-D-Arg-Leu-D-Gln-NH$_2$ (SEQ ID NO:107);
(Me$_3$N$^+$)-Phe-Val-Ala-Ile-Phe-Thr-Tyr-Gly-Glu-Leu-Ala-D-Arg-Leu-D-Gln-NH$_2$ (SEQ ID NO:108);
(N-Me)-Phe-Val-Pro-Ile-Phe-Thr-Tyr-Gly-Glu-Leu-Ala-D-Arg-Leu-D-Gln-NH$_2$ (SEQ ID NO:109);
(Me$_2$N)-Phe-Val-Pro-Ile-Phe-Thr-Tyr-Gly-Glu-Leu-Ala-D-Arg-Leu-D-Gln-NH$_2$ (SEQ ID NO:110);
(Me$_3$N )-Phe-Val-Pro-Ile-Phe-Thr-Tyr-Gly-Glu-Leu-Ala-D-Arg-Leu-D-Gln-NH$_2$ (SEQ ID NO:111);
(N-Me)-Phe-Val-Ala-Ile-Phe-Thr-Tyr-Gly-Glu-Leu-Ala-D-Arg-Leu-Lys-NH$_2$ (SEQ ID NO:112);
(Me$_2$N )-Phe-Val-Ala-Ile-Phe-Thr-Tyr-Gly-Glu-Leu-Ala-D-Arg-Leu-Lys-NH$_2$ (SEQ ID NO:113);
(Me$_3$N)-Phe-Val-Ala-Ile-Phe-Thr-Tyr-Gly-Glu-Leu-Ala-D-Arg-Leu-Lys-NH$_2$ (SEQ ID NO:114);
(N-Me)-Phe-Val-Pro-Ile-Phe-Thr-Tyr-Gly-Glu-Leu-Ala-D-Arg-Leu-Lys-NH$_2$ (SEQ ID NO:115);
(Me$_2$N)-Phe-Val-Pro-Ile-Phe-Thr-Tyr-Gly-Glu-Leu-Ala-D-Arg-Leu-Lys-NH$_2$ (SEQ ID NO:116);
(Me$_3$N$^+$)-Phe-Val-Pro-Ile-Phe-Thr-Tyr-Gly-Glu-Leu-Ala-D-Arg-Leu-Lys-NH$_2$ (SEQ ID NO:117);
(N-Me)-Phe-Val-Ala-Ile-Phe-Thr-Tyr-Gly-Glu-Leu-Ala-D-Arg-Leu-D-Lys-NH$_2$ (SEQ ID NO:118);
(Me$_2$N)-Phe-Val-Ala-Ile-Phe-Thr-Tyr-Gly-Glu-Leu-Ala-D-Arg-Leu-D-Lys-NH$_2$ (SEQ ID NO:119);
(Me$_3$N$^+$)-Phe-Val-Ala-Ile-Phe-Thr-Tyr-Gly-Glu-Leu-Ala-D-Arg-Leu-D-Lys-NH$_2$ (SEQ ID NO:120);
(N-Me)-Phe-Val-Pro-Ile-Phe-Thr-Tyr-Gly-Glu-Leu-Ala-D-Arg-Leu-D-Lys-NH$_2$ (SEQ ID NO:121);
(Me$_2$N)-Phe-Val-Pro-Ile-Phe-Thr-Tyr-Gly-Glu-Leu-Ala-D-Arg-Leu-D-Lys-NH$_2$ (SEQ ID NO:122);
(Me$_3$N )-Phe-Val-Pro-Ile-Phe-Thr-Tyr-Gly-Glu-Leu-Ala-D-Arg-Leu-D-Lys-NH$_2$ (SEQ ID NO:123);
(N-Me)-Phe-Val-Ala-Ile-Phe-Thr-Tyr-Gly-Glu-Leu-Gln-D-Arg-NH$_2$ (SEQ ID NO:124);
(Me$_2$N )-Phe-Val-Ala-Ile-Phe-Thr-Tyr-Gly-Glu-Leu-Gln-D-Arg-NH$_2$ (SEQ ID NO:125);
(Me$_3$N )-Phe-Val-Ala-Ile-Phe-Thr-Tyr-Gly-Glu-Leu-Gln-D-Arg-NH$_2$ (SEQ ID NO:126);
(N-Me)-Phe-Val-Pro-Ile-Phe-Thr-Tyr-Gly-Glu-Leu-Gln-D-Arg-NH$_2$ (SEQ ID NO:127);
(Me$_2$N)-Phe-Val-Pro-Ile-Phe-Thr-Tyr-Gly-Glu-Leu-Gln-D-Arg-NH$_2$ (SEQ ID NO:128);
(Me$_3$N )-Phe-Val-Pro-Ile-Phe-Thr-Tyr-Gly-Glu-Leu-Gln-D-Arg-NH$_2$ (SEQ ID NO:129);
(N-Me)-Phe-Val-Pro-Ile-Phe-Thr-Tyr-Gly-Glu-Leu-Ala-D-Arg-NH$_2$ (SEQ ID NO:130);
(Me$_2$N)-Phe-Val-Pro-Ile-Phe-Thr-Tyr-Gly-Glu-Leu-Ala-D-Arg-NH$_2$ (SEQ ID NO:131);
(Me$_3$N )-Phe-Val-Pro-Ile-Phe-Thr-Tyr-Gly-Glu-Leu-Ala-D-Arg-NH$_2$ (SEQ ID NO:132);
(N-Me)-Phe-Val-Pro-Ile-Phe-Thr-Tyr-Gly-Glu-Leu-Gln-Arg-NH$_2$ (SEQ ID NO:134);
(Me$_2$N)-Phe-Val-Pro-Ile-Phe-Thr-Tyr-Gly-Glu-Leu-Gln-Arg-NH$_2$ (SEQ ID NO:135);
(Me$_3$N )-Phe-Val-Pro-Ile-Phe-Thr-Tyr-Gly-Glu-Leu-Gln-Arg-NH$_2$ (SEQ ID NO:136);
(N-Me)-Phe-Val-Pro-Ile-Phe-Thr-Tyr-Gly-Glu-Leu-Gln-D-Arg-NH$_2$ (SEQ ID NO:127);

(Me₂N )-Phe-Val-Pro-Ile-Phe-Thr-Tyr-Gly-Glu-Leu-Gln-D-Arg-NH₂ (SEQ ID NO:128);

(Me₃N+)-Phe-Val-Pro-Ile-Phe-Thr-Tyr-Gly-Glu-Leu-Gln-D-Arg-NH₂ (SEQ ID NO:129);

(N-Me)-Phe-Val-Ala-Ile-Phe-Thr-Tyr-Gly-Glu-Leu-Gln-Arg-NH₂ (SEQ ID NO:140);

(Me₂N )-Phe-Val-Ala-Ile-Phe-Thr-Tyr-Gly-Glu-Leu-Gln-Arg-NH₂ (SEQ ID NO:141);

(Me₃N )-Phe-Val-Ala-Ile-Phe-Thr-Tyr-Gly-Glu-Leu-Gln-Arg-NH₂ (SEQ ID NO:142);

(N-Me)-Phe-Val-Ala-Ile-Phe-Thr-Tyr-Gly-Glu-Leu-Gln-D-Arg-NH₂ (SEQ ID NO:124);

(Me₂N)-Phe-Val-Ala-Ile-Phe-Thr-Tyr-Gly-Glu-Leu-Gln-D-Arg-NH₂ (SEQ ID NO:125);

Me₃N )-Phe-Val-Ala-Ile-Phe-Thr-Tyr-Gly-Glu-Leu-Gln-D-Arg-NH₂ (SEQ ID NO:126);

(N-Me)-Phe-Val-Ala-Ile-Phe-Thr-Tyr-Gly-Glu-Leu-Ala-Arg-NH₂ (SEQ ID NO:146);

(Me₂N)-Phe-Val-Ala-Ile-Phe-Thr- Tyr-Gly-Glu-Leu-Ala-Arg-NH₂ (SEQ ID NO: 148);

(Me₃N )-Phe-Val-Ala-Ile-Phe-Thr-Tyr-Gly-Glu-Leu-Ala-Arg-NH₂ (SEQ ID NO:149);

(N-Me)-Phe-Val-Pro-Ile-Phe-Thr-Tyr-Gly-Glu-Leu-Gln-Arg-Leu-Lys-NH₂ (SEQ ID NO:150);

(Me₂N)-Phe-Val-Pro-Ile-Phe-Thr-Tyr-Gly-Glu-Leu-Gln-Arg-Leu-Lys-NH₂ (SEQ ID NO:151);

(Me₃N+)-Phe-Val-Pro-Ile-Phe-Thr-Tyr-Gly-Glu-Leu-Gln-Arg-Leu-Lys-NH₂ (SEQ ID NO:152);

(N-Me)-Phe-Val-Ala-Ile-Phe-Thr-Tyr-Gly-Glu-Leu-Gln-Arg-Leu-Lys-NH₂ (SEQ ID NO:153);

(Me₂N)-Phe-Val-Ala-Ile-Phe-Thr-Tyr-Gly-Glu-Leu-Gln-Arg-Leu-Lys-NH₂ (SEQ ID NO:154);

(Me₃N+)-Phe-Val-Ala-Ile-Phe-Thr-Tyr-Gly-Glu-Leu-Gln-Arg-Leu-Lys-NH₂ (SEQ ID NO:155);

(N-Me)-Phe-Val-Pro-Ile-Phe-Thr-Tyr-Gly-Glu-Leu-Ala-Arg-Leu-Lys-NH₂ (SEQ ID NO:156);

(Me₂N)-Phe-Val-Pro-Ile-Phe-Thr-Tyr-Gly-Glu-Leu-Ala-Arg-Leu-Lys-NH₂ (SEQ ID NO:157);

(Me₃N+)-Phe-Val-Pro-Ile-Phe-Thr-Tyr-Gly-Glu-Leu-Ala-Arg-Leu-Lys-NH₂ (SEQ ID NO:158);

(N-Me)-Phe-Val-Ala-Ile-Phe-Thr-Tyr-Gly-Glu-Leu-Ala-Arg-Leu-Lys-NH₂ (SEQ ID NO:159);

(Me₂N)-Phe-Val-Ala-Ile-Phe-Thr-Tyr-Gly-Glu-Leu-Ala-Arg-Leu-Lys-NH₂ (SEQ ID NO:160);

(Me₃N+)-Phe-Val-Ala-Ile-Phe-Thr-Tyr-Gly-Glu-Leu-Ala-Arg-Leu-Lys-NH₂ (SEQ ID NO:161);

(N-Me)-Phe-Val-Pro-Ile-Phe-Thr-Tyr-Gly-Glu-Leu-Gln-Arg-Leu-D-Gln-NH₂ (SEQ ID NO:162);

(Me₂N)-Phe-Val-Pro-Ile-Phe-Thr-Tyr-Gly-Glu-Leu-Gln-Arg-Leu-D-Gln-NH₂ (SEQ ID NO:163);

(Me₃N)-Phe-Val-Pro-Ile-Phe-Thr-Tyr-Gly-Glu-Leu-Gln-Arg-Leu-D-Gln-NH₂ (SEQ ID NO:164);

(N-Me)-Phe-Val-Ala-Ile-Phe-Thr-Tyr-Gly-Glu-Leu-Gln-Arg-Leu-D-Gln-NH₂ (SEQ ID NO:165);

(Me₂N)-Phe-Val-Ala-Ile-Phe-Thr-Tyr-Gly-Glu-Leu-Gln-Arg-Leu-D-Gln-NH₂ (SEQ ID NO:166);

(Me₃N+)-Phe-Val-Ala-Ile-Phe-Thr-Tyr-Gly-Glu-Leu-Gln-Arg-Leu-D-Gln-NH₂ (SEQ ID NO:167);

(N-Me)-Phe-Val-Pro-Ile-Phe-Thr-Tyr-Gly-Glu-Leu-Ala-Arg-Leu-D-Gln-NH₂ (SEQ ID NO:168);

(Me₂N)-Phe-Val-Pro-Ile-Phe-Thr-Tyr-Gly-Glu-Leu-Ala-Arg-Leu-D-Gln-NH₂ (SEQ ID NO:169);

(Me₃N+)-Phe-Val-Pro-Ile-Phe-Thr-Tyr-Gly-Glu-Leu-Ala-Arg-Leu-D-Gln-NH₂ (SEQ ID NO:170);

(N-Me)-Phe-Val-Ala-Ile-Phe-Thr-Tyr-Gly-Glu-Leu-Ala-Arg-Leu-D-Gln-NH₂ (SEQ ID NO:171);

(Me₂N)-Phe-Val-Ala-Ile-Phe-Thr-Tyr-Gly-Glu-Leu-Ala-Arg-Leu-D-Gln-NH₂ (SEQ ID NO:172);

(Me₃N+)-Phe-Val-Ala-Ile-Phe-Thr-Tyr-Gly-Glu-Leu-Ala-Arg-Leu-D-Gln-NH₂ (SEQ ID NO:173), and their pharmaceutically acceptable addition salts. In a most preferred embodiment, the compounds of the present invention are selected from the group consisting of (N-Me)-Phe-Val-Pro-Ile-Phe-Thr-Tyr-Gly-Glu-Leu-Gln-D-Arg-Leu-Gln-OH (SEQ ID NO:15);

(Me₃N+)-Phe-Val-Pro-Ile-Phe-Thr-Tyr-Gly-Glu-Leu-Gln-D-Arg-Leu-Gln-NH₂ (SEQ ID NO:32);

(N-Me)-Phe-Val-Ala-Ile-Phe-Thr-Tyr-Gly-Glu-Leu-Gln-D-Arg-Leu-Gln-NH₂ (SEQ ID NO:56);

(N-Me)-Phe-Val-Pro-Ile-Phe-Thr-Tyr-Gly-Glu-Leu-Gln-D-Arg-Leu-D-Gln-NH₂ (SEQ ID NO:86);

(N-Me)-Phe-Val-Ala-Ile-Phe-Thr-Tyr-Gly-Glu-Leu-Gln-D-Arg-Leu-Lys-NH₂ (SEQ ID NO:147);

(Me₃N+)-Phe-Val-Ala-Ile-Phe-Thr-Tyr-Gly-Glu-Leu-Gln-D-Arg-Leu-Lys-NH₂ (SEQ ID NO:90);

(N-Me)-Phe-Val-Pro-Ile-Phe-Thr-Tyr-Gly-Glu-Leu-Gln-D-Arg-Leu-Lys-NH₂ (SEQ ID NO:91);

(Me₂N)-Phe-Val-Pro-Ile-Phe-Thr-Tyr-Gly-Glu-Leu-Gln-D-Arg-Leu-Lys-NH₂ (SEQ ID NO:92);

(Me₃N)-Phe-Val-Pro-Ile-Phe-Thr-Tyr-Gly-Glu-Leu-Gln-D-Arg-Leu-Lys-NH₂ (SEQ ID NO:93);

(N-Me)-Phe-Val-Pro-Ile-Phe-Thr-Tyr-Gly-Glu-Leu-Ala-D-Arg-Leu-Gln-NH₂ (SEQ ID NO:103);

(Me₃N+)-Phe-Val-Pro-Ile-Phe-Thr-Tyr-Gly-Glu-Leu-Ala-D-Arg-Leu-Gln-NH₂ (SEQ ID NO:105);

(N-Me)-Phe-Val- Pro-Ile-Phe-Thr-Tyr-Gly-Glu-Leu-Ala-D-Arg-Leu-D-Gln-NH₂ (SEQ ID NO:109);

(N-Me)-Phe-Val-Ala-Ile-Phe-Thr-Tyr-Gly-Glu-Leu-Ala-D-Arg-Leu-Lys-NH₂ (SEQ ID NO:112);

(Me₂N)-Phe-Val-Ala-Ile-Phe-Thr-Tyr-Gly-Glu-Leu-Ala-D-Arg-Leu-Lys-NH₂ (SEQ ID NO:113);

(Me₃N+)-Phe-Val-Ala-Ile-Phe-Thr-Tyr-Gly-Glu-Leu-Ala-D-Arg-Leu-Lys-NH₂ (SEQ ID NO:114);

(N-Me)-Phe-Val-Pro-Ile-Phe-Thr-Tyr-Gly-Glu-Leu-Ala-D-Arg-Leu-Lys-NH₂ (SEQ ID NO:115);

(Me₂N)-Phe-Val-Pro-Ile-Phe-Thr-Tyr-Gly-Glu-Leu-Ala-D-Arg-Leu-Lys-NH₂ (SEQ ID NO:116);

(Me₃ N+)-Phe-Val-Pro-Ile-Phe-Thr-Tyr-Gly-Glu-Leu-Ala-D-Arg-Leu-Lys-NH₂ (SEQ ID NO:117);

(N-Me)-Phe-Val-Ala-Ile-Phe-Thr-Tyr-Gly-Glu-Leu-Ala-D-Arg-Leu-D-Lys-NH₂ (SEQ ID NO:118);

(Me₃N)-Phe-Val-Ala-Ile-Phe-Thr-Tyr-Gly-Glu-Leu-Ala-D-Arg-Leu-D-Lys-NH₂ (SEQ ID NO:120);

(Me₂N)-Phe-Val-Pro-Ile-Phe-Thr-Tyr-Gly-Glu-Leu-Ala-D-Arg-Leu-D-Lys-NH₂ (SEQ ID NO:122);

(N-Me)-Phe-Val-Pro-Ile-Phe-Thr-Tyr-Gly-Glu-Leu-Gln-Arg-Leu-Lys-NH₂ (SEQ ID NO:150), (Me₃N+)-Phe-Val-Pro-Ile-Phe-Thr-Tyr-Gly-Glu-Leu-Gln-D-Arg-Leu-D-Gln-NH₂ (SEQ ID NO:88);

and their pharmaceutically acceptable addition salts.

The compounds of the present invention can be prepared by various methods known in the art such as by solid phase peptide synthesis or by classical solution phase synthesis. In the solid phase method, the peptide chain is sequentially constructed using a resin support, typically a polystyrene based, polyhipe based, or a pelyacrylamide/Kieselguhr composite resin. The growing peptide chain is tethered to the resin support by a suitable, acid-labile molecular linker, such as hydroxymethylphenylacetamidomethyl (PAM), 4-methylbenzhydrylamino (MBHA), or hydroxymethylphenoxyacetoxy (HMPA) moieties. The peptide chain can then be cleaved from the linker, and thus the resin support, through acidolysis employing hydrogen fluoride, trifluoroacetic acid (TFA), trifluoromethanesulfonic acid (TFMSA), and the like.

Whether the gastrointestinal motor stimulating polypeptides of this invention are prepared by solid phase or solution phase methods, the basic synthetic approach involves coupling of amino acid subunits through reaction of the carboxyl moiety of one suitably protected amino acid or peptide fragment with the amino group of another suitably protected amino acid or peptide fragment to form a new amide bond. In order to effect the coupling reaction, the carboxyl moiety must be activated. Activation is accomplished through the use of standard coupling reagents such as DCC, DIC, EDCC, BOP, HBTU, or PyBrOP. Except in the case of PyBrOP, an equimolar amount of HOBt may be added to suppress racemization of the activated amino acid component. Bases such as NMM, DIEA, or TEA may be used in those cases where it is necessary to employ the carboxylate salt of the corresponding amino acid for activation.

Alternatively, the peptides of this invention can be synthesized by coupling the active esters of the component amino acids. Such active esters include, for example, a pentachlorophenyl ester, a pentafluorophenyl ester, p-nitrophenyl ester, and the like.

During the preparation of the peptides of this invention, other reactive functionalities of the amino acid components must be blocked with appropriate protecting groups. In general, the identity of the α-amino protecting group dictates what type of side-chain protecting groups must be employed. For example, in the case where the α-amino group is protected as its Boc derivative, side-chain protection is usually accomplished with ester, ether, or urethane derivatives of benzyl alcohol. Ester and ether derivatives of cyclohexanol have also been used with some success. In contrast, when the α-amino group is protected as its Fmoc derivative, side chain functionality is generally protected as ester, ether, or urethane derivatives of t-butanol. Of course, alternative combinations of protecting groups may be employed especially when the peptides of this invention are synthesized by solution phase methodology.

Removal of the Fmoc a-amino protecting group may be readily accomplished with a base, typically piperidine. The side chain protecting groups can be removed by treatment with TFA in the presence of an appropriate carbonium ion scavenger, which also cleaves the bond between the C-terminus of the peptide and the resin linker. The Boc protecting group is generally removed by treatment with dilute TFA. Following TFA cleavage, however, the α-amino group is present as its TFA salt. In order to make the α-amino group of the growing peptide chain reactive toward the next amino acid derivative, the resin-bound peptide is neutralized with a base such as TEA or DIEA. Strong acid, such as hydrofluoric acid or TFMSA, containing suitable scavengers is then used to deprotect the amino acid side-chains and to cleave the peptide from the resin support.

In accord with the present invention, a process is provided for the preparation of peptides which contain the amino-terminal portion, $(R_1)_m(R_2)(R_3)N—$. When $m=0$; $R_2$ is hydrogen or lower-alkyl; and $R_3$ is lower-alkyl, the method comprises reacting the N-terminal amino group $(NH_2—(AA)_n—)$ of a suitably protected peptide, optionally bound to an insoluble support through an appropriate linker, with an appropriate aldehyde or ketone and an alkali metal hydride reducing agent. The aldehyde or ketone may be, for example, formaldehyde, acetaldehyde, or acetone. The alkali metal hydride may be, for example, an alkali metal borohydride such as sodium cyanoborohydride. The process is conveniently carried out in a suitable solvent, such as DMF or NMP, optionally together with acetic acid or 1-hydroxyethylpiperazine ethanesulfonic acid (HEPES), at ambient temperature. The method is more fully described in U.S. Pat. No. 4,421,744, which disclosure is incorporated herein by reference.

When $m=1$; $R_1$ and $R_3$ are independently lower-alkyl or allyl; and $R_2$ is selected from the group consisting of lower-alkyl, allyl, and propargyl, the method comprises reacting the N-terminal amino group $(NR_2R_3—(AA)_n—)$ of a suitably protected peptide, optionally bound to an insoluble support through an appropriate linker, with a compound represented by the formula $R_1Hal$, wherein $R_1$ is defined above and Hal is a halogen atom. The reaction is carried out in a suitable solvent, such as DMF or NMP, in the presence of a suitable acid-binding agent, such as sodium carbonate or potassium carbonate. The method is more fully described in Benoiton-Chen, *Proced. 14th Europ. Pept. Symp.*, (1976), p. 149., which disclosure is incorporated herein by reference.

The compounds of the present invention while effective in the form of the free base may be formulated and administered in the form of pharmaceutically acceptable acid addition salts for purposes of stability, convenience of crystallization, increased solubility and the like. These acid addition salts are formed by conventional methods from suitable inorganic or organic acids such as hydrochloric, sulfuric, sulfonic, tartaric, fumaric, hydrobromic, glycolic, citric, maleic, phosphoric, succinic, acetic, nitric, benzoic, ascorbic, p-toluenesulfonic, benzenesulfonic, naphthalenesulfonic, propionic acid, and the like. Preferably, the acid addition salts are those prepared from hydrochloric acid, acetic acid, or succinic acid.

The compounds of the present invention can be combined with a pharmaceutically acceptable carrier to provide a pharmaceutical composition. Suitable carders for the subject compounds as the free base include propylene glycol-alcohol-water, isotonic water, sterile water for injection (USP), emulPhor ™-alcohol-water, cremophor-EL ™ or other suitable carriers known to those skilled in the art.

Suitable carriers for the acid addition salts of the subject compounds include isotonic water, sterile water for injection (USP), alone or in combination with other solubilizing agents such as ethanol, propylene glycol, or other conventional solubilizing agents known to those skilled in the art. A preferred carrier is an isotonic aqueous solution of the inventive compound.

The compounds of the present invention can be administered to mammals, e.g., animals or humans, in amounts effective to provide the desired gastrointestinal motor stimulating activity. Since the activity of the compounds and the degree of the desired therapeutic effect vary, the dosage level of the compound employed will also vary. The actual dosage administered will also be determined by such generally recognized factors as the body weight of the patient and the individual hypersensitiveness of the particular patient. Thus, the unit dosage for a particular patient (man) can vary from as low as about 0.1 μg per kg of body weight, which the practitioner may titrate to the desired effect. A preferred minimum dose for titration is 1 μg/kg body weight.

The compounds of the present invention can be administered by recognized parenteral routes, in the form of sterile solutions or suspensions, in the carriers previously described. These preparations should contain at least about 0.1%, by weight, of the inventive compound but this mount may be varied to between about 0.1% and about 50%, by weight, of the inventive compound. The compounds of the present invention are preferably administered intravenously and the dosage used will generally be in the range from about 0.1 μg to about 500 mg, and preferably from about 1 μg to about 50 mg, per 70 kg body weight. This dosage may be administered from 1 to 4 times daily.

The sterile solutions or suspensions may also include the following adjuvants: a sterile diluent, such as water for injection, saline solution, fixed oils, polyethylene glycol, glycerine, propylene glycol, or other synthetic solvent; antibacterial agents, such as benzyl alcohol or methyl paraben; antioxidants, such as ascorbic acid or sodium metabisulfite; chelating agents, such as ethylenediaminetetraacetic acid (EDTA); buffers, such as acetates, titrates or phosphates; and agents for the adjustment of tonicity, such as sodium chloride or dextrose. The parenteral preparations may be enclosed in arepules, disposable syringes, or multiple dosage vials made of glass or plastic.

Throughout this application, various publications have been referenced. The disclosures in these publications are incorporated herein by reference in order to more fully describe the state of the art.

The present invention is further illustrated by the following examples which are presented for purposes of demonstrating, but not limiting, the preparation of the compounds and compositions of this invention.

EXAMPLE 1

[12-D-Arginine, 13-leucine]motilin-(1–14)-peptide (Porcine) Bis-trifluoroacetate Salt H-Phe-Val-Pro-Ile-Phe-Thr-Tyr-Gly-Glu-Leu-Gln-D-Arg-Leu-Gln-OH. (SEQ ID NO:14)

The polypeptide was synthesized on 2.0 g. of Fmoc-L-Gln(Mbh)PepSyn KA resin (0.097 mequiv/g) by solid phase continuous flow techniques employing a MilliGert Model 9050 peptide synthesizer. All residues were coupled as Pfp esters of the Fmoc amino acids in the presence of HOBt, except for Thr which was the ODhbt ester. The side chain protection was as follows: D-Arg(Mtr), Glu(OtBu), Tyr(tBu), and Thr(tBu). Gln was left unprotected. A four-fold molar excess of the Fmoc amino acid OPfp/HOBt in DMF was used for coupling. Coupling efficiency was monitored by the Kaiser test. Coupling times ranged from 1 to 4 hours. After each coupling cycle, removal of the Fmoc-α-amino protecting group was accomplished with 20% piperidine in DMF. Following synthesis, the resin-bound peptide was washed with DCM and dried under vacuum overnight. Deblocking and cleavage of the peptide from the resin was performed at room temperature by shaking with anhydrous TFA containing 5% thioanisole, 3% ethanedithiol, and 2% anisole (20 ml total) for 8 hours. The cleavage solution then was added dropwise to 250 ml cold ether and the precipitated peptide collected by filtration to obtain 320 mg (85 %) of the title peptide as a white powder. Peptide purification was achieved in three runs (typical load = 107 mg per run) by HPLC on a Waters Delta-Prep 3000 using two C-18 columns in series (250×20 mm, 15μ, Vydac). The solvent system was 0.1% TFA with a 30 minute gradient to 60% acetonitrile/40% TFA(0.1%) at 20 ml/min with UV detection at 220 nm. The purity of individual fractions was assessed by analytical HPLC (30 minute gradient, 100% TFA(0.1%) to 100% acetonitrile, 1 ml/min, 214 nm; $R_t$=17.37 minutes) and capillary zone electrophoresis. Pure fractions (>95%) were pooled and lyophilized to provide 107 mg (28%) of the title polypeptide as a flocculent white powder.

AAA: Thr 0.87 (1), Glx 3.02 (3), Gly 1.04 (1), Val 1.02 (1), Ile 0.92 (1), Leu 2.14 (2), Tyr 1.00 (1), Phe 1.93 (2), Arg 0.93 (1). FAB-MS: $(M+H)^+$ calcd 1712, found 1712.

EXAMPLE 2

[1-N-Methylphenylalanine, 3-alaninc, 11-alanine, 12-D-arginine, 13-Leucine, 14-D-lysine]motilin-(1–14)-peptide Amide (Porcine) Tris-trifluoroacetate Salt (N-Me)-Phe-Val-Ala-Ile-Phe-Thr-Tyr-Gly-Glu-Leu-Ala-D-Arg-Leu-D-Lys-NH$_2$. (SEQ ID NO:118)

The polypeptide was synthesized on 0.85 g. of PAL resin (0.27 mequiv/g) by solid phase continuous flow techniques employing a MilliGen Model 9050 peptide synthesizer. The resin was mixed with 3.4 g of glass beads (acid washed, 150–212 microns), dry-packed into a continuous flow column, and swelled with DMF for 1 hour prior to use. Fmoc-MePhe-OH was coupled by preactivation with BOP and HOBt (1:1:1) in the presence of 0.6M NMM in DMF. Fmoc-L-Thr-OH was coupled as its ODhbt ester in the presence of HOBt. All other residues were coupled as Pfp esters of the Fmoc amino acids in the presence of HOBt. The side chain protection was as follows: D-Arg(Mtr), Glu(OtBu), Tyr(tBu), Thr(tBu), D-Lys(Boc), Gln(Trt). A four-fold molar excess of the Fmoc amino acid derivative in DMF was used for coupling. Coupling efficiency was monitored by the Kaiser test. Typical coupling times ranged from 1 to 4 hours. After each cycle, removal of the Fmoc-a-amino protecting group was accomplished with 20% piperidine in DMF. Following synthesis, the resin-bound peptide was washed with DCM and dried under vacuum overnight. Deblocking and cleavage of the peptide from the resin was performed at room temperature by shaking with anhydrous TFA containing 5% thioanisole, 3% ethanedithiol, and 2% anisole (20 ml total) for 8 hours. The cleavage solution then was added dropwise to 250 ml cold ether and the precipitated peptide collected by filtration to obtain 210 mg (91%) of the title polypeptide as a white powder. Peptide purification was achieved in three runs (typical load = 70 mg per run) by HPLC on a Waters Delta-Prep 3000 using two C-18 columns in series (250×20 mm, 15μ, Vydac). The solvent system was 0.1% TFA with a 30 minute gradient to 60% acetonitrile/40% TFA(0.1%) at 20 ml/min with UV detection at 220 nm. The purity of individual fractions was assessed by analytical HPLC (30 minute gradient, 100% TFA(0.1%) to 100% acetonitrile, 1 ml/min, 214 nm; $R_t$=17.06 minutes) and capillary zone electrophoresis. Pure fractions (>95%) were pooled and lyophilized to provide 82 mg (36%) of the title polypeptide as a flocculent white powder.

AAA: Thr 0.95 (1), Glx 1.04 (1), Gly 1.04 (1), Val 0.74 (1), Ile 0.99 (1), Leu 2.11 (2), Tyr 1.01 (1), Phe 1.01

(1), Lys 1.03 (1), Arg 1.05 (1). FAB-MS: (M+H)+ calcd 1641, found 1641.

EXAMPLE 3

[1-N,N-Dimethylphenylalanine, 13-leucine]motilin-(1–14)-peptide Amide (Porcine) Bis-trifluoroacetate Salt (Me$_2$N)-Phe-Val-Pro-Ile-Phe-Thr-Tyr-Gly-Glu-Leu-Gln-Arg-Leu-Gln-NH$_2$. (SEQ ID NO:31)

The polypeptide was synthesized on NovaSynPR 500 resin on a 0.2 mmole scale by solid phase continuous flow techniques employing a MilliGen Model 9050 peptide synthesizer. All residues were coupled as Pfp esters of the Fmoc amino acids in the presence of HOBt, except for Thr which was the ODhbt ester. The side chain protection was as follows: Arg(Mtr), Gln(Trt), Glu(OtBu), Tyr(tBu), and Thr(tBu). A four-fold molar excess of the Fmoc amino acid OPfp/HOBt in DMF was used for coupling. Coupling efficiency was monitored by the Kaiser test. Coupling times ranged from 1 to 4 hours. After each coupling cycle, removal of the Fmoc-a-amino protecting group was accomplished with 20% piperidine in DMF. Following synthesis, the resin-bound peptide was washed with DCM and dried under vacuum overnight. The resin containing the fully assembled peptide was transferred to a flask containing 20 ml NMP. To this suspension, 5 ml of 37 % aqueous formaldehyde (300eq), 126 mg of sodium cyanoborohydride (10 eq), and 200 μl of glacial acetic acid were added sequentially. The mixture was stirred for 7 hours. The resin was filtered and washed with DMF (5×50 ml), DCM (5×50 ml) and dried under vacuum. Deblocking and cleavage of the peptide from the resin was performed at room temperature by shaking with anhydrous TFA containing 5% thioanisole, 3% ethanedithiol, and 2% anisole (20 ml total) for 8 hours. The cleavage solution then was added dropwise to 250 ml cold ether and the precipitated peptide collected by filtration to obtain the title polypeptide as a white powder. Peptide purification was achieved in three runs (typical load =70 mg per run) by HPLC on a Waters Delta-Prep 3000 using two C-18 columns in series (250×20 mm, 15μ, Vydac). The solvent system was 0.1% TFA with a 30 minute gradient to 60% acetonitrile/40% TFA(0.1%) at 20 ml/min with UV detection at 220 nm. Pure fractions (>95%) were pooled and lyophilized to provide 111 mg of the rifle polypeptide as a flocculent white powder.

AAA: Thr 0.84 (1), Glx 2.88 (3), Pro 1.03 (1), Gly 1.04 (1), Val 0.47 (1), Ile 0.87 (1), Leu 1.88 (2), Tyr 0.90 (1), Phe 0.97 (1), Arg 0.86 (1). FAB-MS: (M+H)+ calcd 1738, found 1738.

EXAMPLE 4

[1-N,N,N-Trimethylphenylalanine, 13-leucine]motilin-(1–14)-peptide (Porcine) Bis-trifluoroacetate Salt (Me$_3$N+)-Phe-Val-Pro-Ile-Phe-Thr-Tyr-Gly-Glu-Leu-Gln-Arg-Leu-Gln-OH. (SEQ ID NO:31)

The polypeptide was synthesized on FMOC-L-Gln-(Mbh) PepSynKA resin on a 0.2 mmole scale by solid phase continuous flow techniques employing a Milli-Gen Model 9050 peptide synthesizer. All residues were coupled as Pfp esters of the Fmoc amino acids in the presence of HOBt, except for Thr which was the ODhbt ester. The side chain protection was as follows: Arg(Mtr), Glnffrt), Glu(OtBu), Tyr(tBu), and Thr(tBu). A four-fold molar excess of the Fmoc amino acid OPfp/HOBt in DMF was used for coupling. Coupling efficiency was monitored by the Kaiser test. Coupling times ranged from 1 to 4 hours. After each coupling cycle, removal of the Fmoc-α-amino protecting group was accomplished with 20% piperidine in DMF. Following synthesis, the resin-bound peptide was washed with DCM and dried under vacuum overnight. The resin containing the fully assembled peptide was transferred to a flask containing 20 ml DMF. To this suspension, 5 ml of methyl iodide (400 eq) followed by 500 mg of potassium carbonate (18 eq) were added. The mixture was stirred for 12 hours. The resin was filtered and washed with DMF (5×50 ml), water (2×25 ml) DMF (5×50 ml) and dried under vacuum. Deblocking and cleavage of the peptide from the resin was performed at room temperature by shaking with anhydrous TFA containing 5% thioanisole, 3% ethanedithiol, and 2% anisole (20 ml total) for 8 hours. The cleavage solution then was added dropwise to 250 ml cold ether and the precipitated peptide collected by filtration to obtain the title polypeptide as a white powder. Peptide purification was achieved in three runs (typical load=70 mg per run) by HPLC on a Waters Delta-Prep 3000 using two C-18 columns in series (250×20 mm, 15μ, Vydac). The solvent system was 0.1% TFA with a 30 minute gradient to 60% acetonitrile/40% TFA(0.1%) at 20 ml/min with UV detection at 220 nm. Pure fractions (>95% ) were pooled and lyophilized to provide 71 mg of the title polypeptide as a flocculent white powder.

AAA: Thr 0.88 (1), Glx 3.25 (3), Pro 1.00 (1), Gly 1.00 (1), Val 0.30 (1), Ile 1.01 (1), Leu 2.30 (2), Tyr 1.10 (1), Phe 1.10 (1), Arg 1.10 (1). FAB-MS: (M+H)+ calcd 1753, found 1753.

EXAMPLE 5

In vitro Stability testing in 2% hog kidney homogenate

Like most small linear polypeptides, motilin is believed to be metabolized lo by the brush border cells of the kidney. Therefore, kidney homogenate was chosen as the model system for assessing the relative in vivo biostability of the peptides of this invention. All peptides to be studied were incubated in hog kidney (Pel Freeze, Inc., Rogers, Ark.) (2% w/v; final volume=4 ml; buffer=HEPES pH 7.0) at 25° C. Both initial substrate concentration and internal standard (Fmoc-Gly) concentration were 0.5 mg/ml. In order to determine suitable incubation times and sampling intervals, two experiments were conducted with each polypeptide. The first run served as a rough estimate of peptide stability. All sampling was performed in duplicate. Sample volume was 180 μl.

Sample clean-up was performed by addition of 20 μl of 100% TCA (final volume=200 μl; final TCA concentration=10%). The sample was vortexed for from 5 to 10 seconds to ensure equilibration, then centrifuged to spin out the precipitated proteins. Analysis was carried out on a Waters HPLC system with a WISP autoinjector, a 5μ Vydac C-18 analytical column, and a Waters 481 UV detector set at 214 nm. Injection volume was 80 μl. Initial solvent conditions were 80% acetonitrile/20% (0.1%) TFA in Milli-Q water with a 35 minute gradient running to 63% acetonitrile/37% (0.1%) TFA at 1 ml/min.

Polypeptide substrate and metabolite peaks were ratioed to the internal standard and the duplicate sample ratios were averaged. The avenge ratio for the peptide substrate was expressed as a percentage and plotted versus time. First-order kinetics was assumed for data treatment. The rate of disappearance of the substrate was calculated using the Enzfitter program (Biosoft). Relative half-lives were determined from the relationship:

$$t_{\frac{1}{2}} = 0.693/k$$

EXAMPLE 6

Determination of motilin receptor binding affinity

The motilin receptor binding affinity of the peptides of this invention was determined by using the general procedure of Bormans, Peelers and Vantrappen, Regul. Pept., 15, 143–153 (1986). The ability of the peptides to displace [$^{125}$I-Tyr$^7$, Nle$^{13}$]motilin(porcine) bound to rabbit antral smooth muscle membranes, was determined by testing twice, each time in duplicate, at concentrations ranging from $10^{-11}$ to $10^{-4}$M. The concentration displacing 50% of the label (IC$_{50}$) was determined by fitting the data to the equation describing displacement, assuming a single class of motilin receptors to which labeled and non-labeled motilin bind with equal affinity and non-cooperatively. Fitting was performed using the iterative least-squares procedure of the SAS-software package (SAS Institute, Inc., Cary, N.C., USA). From a large series of control experiments the dissociation constant of motilin itself was calculated as 0.75 nM (pK$_d$=9.12), and this value was used for all calculations. The concentration displacing 50% of the label is expressed using its negative logarithm (pIC$_{50}$).

EXAMPLE 7

Rabbit duodenal smooth muscle strip tissue bath assay

The contractile response of segments of rabbit duodenum was determined isotonically in the tissue bath according to the procedure of Depoortere et at., J. Gastrointestinal Motility, 1, 150–159 (1989). The experimental protocol consisted of an equilibration period of 1 hour; a challenge with $10^{-4}$M acetylcholine followed by a wash-out period; a cumulative dose-response curve of a compound with, at the end, the addition of $10^{-7}$M motilin; and finally $10^{-4}$M acetylcholine. If the final response to $10^{-4}$M acetylcholine differed by more than 5% from the initial response, the results were discarded. The compounds were tested in the concentration range $10^{-11}$ to $10^{-4}$M. The point corresponding to 50% of the maximal response to motilin (E$_{max}$) was determined by fitting the equation E=E$_{max}$(1+EC$_{50}$/[L]) through the data points. For weakly active compounds 90% of the response to $10^{-7}$M motilin was used as E$_{max}$. The dose giving 50% of the response is expressed using its negative logarithm (pEC$_{50}$).

EXAMPLE 8

Contractile activity in the canine gastrointestinal tract.

Mongrel dogs of either sex were anesthetized with sodium pentobarbital 65 mg/kg intravenously. A mid-line incision was made in the abdomen. A duodenal segment was located, the terminal arteries to that segment were identified, and the closest possible artery of the appropriate size was rubbed clean of fat and fascia. A needle of suitable diameter was bent at an angle and the tip inserted in the cleaned artery. The needle was held in position in the artery for approximately 30 seconds until vascular spasm has relaxed and then a catheter assembly was inserted into the artery and tied into position with 000 silk sutures. The fine polyethylene catheter (10–15 cm) was cut to a point at one end with a needle inserted at the other end. The hub of the needle was fitted with a 3-way stopcock and the catheter assembly was filled with heparinized Krebs Ringer bicarbonate containing 10 mM glucose. A bolus of Krebs (free of air) was injected into the arterial catheter and the distribution of blanching in the segment noted. If the area was too large, collateral arteries may be tied off as long as circulation to the area was maintained. A Bass type strain gauge was then sutured to the serosa, and oriented so that circular muscle contractions can be recorded on a Beckman R611 dynograph. Silver wire electrodes were inserted subserosally on either side of the strain gauge and were connected through stimulus isolation units to a Grass S88 electrical stimulator. Electrical field stimulation was applied at 40 V 0.5 ms and 5 pps and the amplitude of the pen recorder was set to contain the contractile response.

All peptides to be injected were dissolved in Krebs and serial dilutions were prepared so that for any concentration the maximum volume to be injected was 1 ml. All solutions except stock Krebs were held on ice for the day of the experiment and discarded at the end of the day. For determination of a dose-response curve, the site was first injected with a bolus of approximately 1 ml of heparinized Krebs to provide a flush control. Peptide agonists (in volumes of 1 ml flushed with 1 ml of Krebs) were injected in logarithmic increments until a response which was maximal in amplitude was obtained. The injection site was then flushed with Krebs containing 0.1% BSA to displace any peptide remaining in the arterial line. For peptides acting at the motilin receptor, care was taken not to inject supramaximal doses as these will induce tachyphylaxis. Therefore, as responses become apparent, 0.3 or 0.5 log unit increments were used. A site was used for a dose-response determination only every $\frac{1}{2}$ to 1 hour.

The amplitude of the calibration response to field stimulation in each site was measured and used as 100% for that site. The amplitude of the response to the agonist at each dose was determined, calculated as a % of the calibration response and plotted against the concentration. The ED$_{50}$ of the response represents the amount of agonist required to produce a response which was 50% of the calibration response. It reflects both the efficacy of the response and the potency and does not really distinguish clearly between them.

TABLE 1

| Potency Of Motilin Receptor Agonists In Binding And In Contractility Experiments | | |
|---|---|---|
| Compound | pEC$_{50}$ | pIC$_{50}$ |
| [Leu$^{13}$]pMOT(1–22) | 8.13 | 9.18 |
| [Leu$^{13}$]pMOT(1–14) | 7.55 | 8.36 |
| [D-Arg$^{13}$, Leu$^{13}$]pMOT(1–14) | 7.74 | 9.01 |
| [D-Arg$^{13}$, Leu$^{13}$]pMOT(1–14) amide | 7.50 | 8.61 |

TABLE 1-continued

Potency Of Motilin Receptor Agonists
In Binding And In Contractility Experiments

| Compound | pEC$_{50}$ | pIC$_{50}$ |
|---|---|---|
| [Ala$^3$, D-Arg$^{12}$, Leu$^{13}$]pMOT(1-14) amide | 7.76 | 8.71 |
| [D-Arg$^{12}$, Leu$^{13}$, Lys$^{14}$]pMOT(1-14) amide | 7.13 | 8.89 |
| [D-Orn$^{12}$, Leu$^{13}$]pMOT(1-14) | 6.83 | 8.37 |
| [D-Gln$^{12}$, Leu$^{13}$]pMOT(1-14) | 7.06 | 8.25 |
| [D-Ala$^{12}$, Leu$^{13}$]pMOT(1-14) | 7.29 | 8.05 |
| [D-Arg$^{12}$, Leu$^{13}$]pMOT(1-22) | 7.67 | 8.78 |
| [D-Asn$^{12}$, Leu$^{13}$]pMOT(1-14) | 6.82 | 8.12 |
| [Phe$^7$, D-Arg$^{12}$, Leu$^{13}$]pMOT(1-14) | 6.92 | 8.07 |
| [D-Ala$^8$, D-Arg$^{12}$, Leu$^{13}$]pMOT(1-14) | 7.09 | 8.22 |
| [Cha$^1$, D-Arg$^{12}$, Leu$^{13}$]pMOT(1-14) | 7.60 | 8.75 |
| [Ala$^3$, D-Arg$^{12}$, Leu$^{13}$]pMOT(1-14) | 7.71 | 8.67 |
| [Ala$^{11}$, D-Arg$^{12}$, Leu$^{13}$]pMOT(1-14) | 7.63 | 8.78 |
| [N-MePhe$^1$, Ala$^3$, Ala$^{11}$, D-Arg$^{12}$, Leu$^{13}$, D-Lys$^{14}$]pMOT(1-14) amide | 7.80 | 9.35 |
| [D-Cha$^1$, Ala$^3$, Ala$^{11}$, D-Arg$^{12}$, Leu$^{13}$, D-Lys$^{14}$]pMOT(1-14) amide | 7.25 | 9.03 |
| [N-MePhe$^1$, D-Arg$^{12}$, Leu$^{13}$, Lys$^{14}$]pMOT(1-14) amide | 7.74 | 9.10 |
| [N-MePhe$^1$, Leu$^{13}$, Lys$^{14}$]pMOT(1-14) amide | 7.74 | 9.32 |
| [N-MePhe$^1$, Ala$^{11}$, D-Arg$^{12}$, Leu$^{13}$, Lys$^{14}$]pMOT(1-14) amide | 8.01 | 9.33 |
| [N-MePhe$^1$, Leu$^{13}$, D-Gln$^{14}$]pMOT(1-14) amide | 7.% | 9.21 |
| [N-MePhe$^1$, D-Arg$^{12}$, Leu$^{13}$, D-Gln$^{14}$]pMOT(1-14) amide | 7.77 | 9.07 |
| [N-MePhe$^1$, Ala$^{11}$, D-Arg$^{12}$, Leu$^{13}$, D-Gln$^{14}$]pMOT(1-14) amide | 7.97 | 9.07 |
| [Me$_3$N$^+$Phe$^1$, Leu$^{13}$, D-Gln$^{14}$]pMOT(1-14) amide | 7.64 | 8.71 |
| [Me$_3$N$^+$Phe$^1$, D-Arg$^{12}$, Leu$^{13}$, D-Gln$^{14}$]pMOT(1-14) amide | 7.39 | 8.71 |
| [Me$_3$N$^+$Phe$^1$, Ala$^{11}$, D-Arg$^{12}$, Leu$^{13}$,D-Gln$^{14}$]pMOT(1-14) amide | 7.25 | 8.61 |
| [N-MePhe$^1$, Ala$^3$, Leu$^{13}$, Lys$^{14}$]pMOT(1-14) amide | 7.72 | 9.21 |
| [N-MePhe$^1$, D-Arg$^{12}$, Leu$^{13}$]pMOT(1-14) | 7.71 | 8.72 |
| [Me$_3$N$^+$Phe$^1$, Ala$^3$, Leu$^{13}$, Lys$^{14}$]pMOT(1-14) amide | 7.58 | 8.82 |
| [Me$_3$N$^+$Phe$^1$, D-Arg$^{12}$, Leu$^{13}$]pMOT(1-14) | 7.52 | 8.45 |
| [N-MePhe$^1$, Ala$^3$, D-Arg$^{12}$, Leu$^{13}$, Lys$^{14}$]pMOT(1-14) amide | 7.72 | 9.20 |
| [Me$_3$N$^+$Phe$^1$, Ala$^3$, D-Arg$^{12}$, Leu$^{13}$, Lys$^{14}$]pMOT(1-14) amide | 7.32 | 8.72 |
| [N-MePhe$^1$, Ala$^3$, D-Arg$^{12}$, Leu$^{13}$, D-Gln$^{14}$]pMOT(1-14) amide | 8.07 | 9.11 |
| [Me$_3$N$^+$Phe$^1$, Ala$^3$, D-Arg$^{12}$, Leu$^{13}$, D-Gln$^{14}$]pMOT(1-14) amide | 7.20 | 8.85 |
| [N-MePhe$^1$, Ala$^3$, D-Arg$^{12}$, Leu$^{13}$]pMOT(1-14) amide | 7.79 | 9.23 |
| [Me$_3$N$^+$Phe$^1$, Ala$^3$, D-Arg$^{13}$, Leu$^{13}$]pMOT(1-14) amide | 7.32 | 8.79 |
| [Me$_3$N$^+$Phe$^1$, Ala$^3$, D-Arg$^{12}$, Leu$^{13}$]pMOT(1-14) amide | 7.57 | 8.58 |
| [N-MePhe$^1$, D-Arg$^{12}$, Leu$^{13}$]pMOT(1-14) amide | 7.95 | 8.99 |
| [Me$_3$N$^+$Phe$^1$, D-Arg$^{12}$, Leu$^{13}$]pMOT(1-14) amide | 7.73 | 8.67 |
| [N-MePhe$^1$, Ala$^3$, Ala$^{11}$, D-Arg$^{12}$, Leu$^{13}$, Lys$^{14}$]pMOT(1-14) amide | 7.77 | 9.14 |
| [Me$_3$N$^+$Phe$^1$, Ala$^3$, Ala$^{11}$, D-Arg$^{12}$, Leu$^{13}$,Lv,14]pMOT(1-14) amide | 7.59 | 8.72 |
| [Cha$^5$, D-Arg$^{12}$, Leu$^{13}$]pMOT(1-14) amide | 7.30 | 8.17 |
| [N-MePhe$^1$, Leu$^{13}$]pMOT(1-14) | 7.64 | 8.58 |
| [Me$_3$N$^+$Phe$^1$, Leu$^{13}$]pMOT(1-14) amide | 7.48 | 8.57 |
| [Me$_3$N$^+$Phe$^1$, Leu$^{13}$]pMOT(1-14) | 7.69 | 8.45 |
| [Et$_2$Phe$^1$, Leu$^{13}$]pMOT(1-14) amide | 7.54 | 8.41 |
| [N,N-DiMe-N-PropargylPhe$^1$, Leu$^{13}$]pMOT(1-14) amide | 7.65 | 8.67 |
| [N-Me-N-PropargylPhe$^1$, Leu$^{13}$]pMOT(1-14) amide | 7.57 | 8.70 |
| [N-Allyl-N,N-DiMePhe$^1$, Leu$^{13}$]pMOT(1-14) amide | 7.47 | 8.76 |
| [N-MePhe$^1$, Ala$^{11}$, D-Arg$^{12}$, Leu$^{13}$]pMOT(1-14) amide | 7.60 | 9.03 |
| [N-MePhe$^1$, Ala$^3$, Ala$^{11}$, D-Arg$^{12}$, Leu$^{13}$, D-Gln$^{14}$]pMOT(1-14) amide | 7.32 | 9.14 |
| [Me$_3$N$^+$Phe$^1$, Ala$^3$, Ala$^{11}$, D-Arg$^{12}$, Leu$^{13}$,D-Gln$^{14}$]pMOT(1-14) amide | 7.22 | 8.84 |
| [N-MePhe$^1$, Ala$^3$, Ala$^{11}$, D-Arg$^{13}$, Leu$^{13}$]pMOT(1-14) amide | | |
| [Me$_3$N$^+$Phe$^1$, Leu$^{13}$, Lys$^{14}$]pMOT(1-14) amide | 7.64 | 8.90 |
| [Me$_3$N$^+$Phe$^1$, Ala$^3$, Ala$^{11}$, D-Arg$^{12}$, Leu$^{13}$,D-Lys$^{14}$]pMOT(1-14) amide | 7.55 | 8.94 |
| [Me$_2$NPhe$^1$, Ala$^{11}$, D-Arg$^{12}$, Leu$^{13}$, Lys$^{14}$]pMOT(1-14) amide | 7.64 | 8.91 |
| [Me$_2$NPhe$^1$, Ala$^3$, Ala$^{11}$, D-Arg$^{12}$, Leu$^{13}$,Lys$^{14}$]pMOT(1-14) amide | 7.74 | 9.15 |
| [Me$_3$N$^+$Phe$^1$, Ala$^3$, Ala$^{11}$, D-Arg$^{13}$, Leu$^{13}$]pMOT(1-14) amide | 7.31 | 8.71 |
| [Me$_3$N$^+$Phe$^1$, D-Arg$^{13}$, Leu$^{13}$, Lys$^{14}$]pMOT(1-14) amide | 7.60 | 8.93 |
| [Me$_3$N$^+$Phe$^1$, Ala$^{11}$, D-Arg$^{12}$, Leu$^{13}$, Lys$^{14}$]pMOT(1-14) amide | 7.64 | 8.89 |
| [Me$_2$NPhe$^1$, Ala$^{11}$, D-Arg$^{12}$, Leu$^{13}$, D-Lys$^{14}$]pMOT(1-14) amide | 7.69 | 8.84 |
| [Me$_2$NPhe$^1$, Ala$^3$, Ala$^{11}$, D-Arg$^{12}$, Leu$^{13}$,D-Lys$^{14}$]pMOT(1-14) amide | 7.73 | 8.39 |
| [Me$_2$NPhe$^1$, D-Arg$^{12}$, Leu$^{13}$]pMOT(1-14) amide | 7.71 | 8.75 |
| [Me$_2$NPhe$^1$, D-Arg$^{12}$, Leu$^{13}$, Lys$^{14}$]pMOT(1-14) amide | 7.73 | 8.93 |
| [Me$_2$NPhe$^1$, Ala$^{11}$, D-Arg$^{12}$, Leu$^{13}$]pMOT(1-14) amide | 7.76 | 8.71 |

*pMOT = porcine motilin

TABLE 2

Half-Lives Of Motilin Receptor Agonists
In 2% Hog Kidney Homogenate

| Compound | T$_{\frac{1}{2}}$ |
|---|---|
| [Leu$^{13}$]pMOT(1-22) | 30.2 |
| [Leu$^{13}$]pMOT(1-14) | 7.5 |

TABLE 2-continued
Half-Lives Of Motilin Receptor Agonists In 2% Hog Kidney Homogenate

| Compound | T½ |
|---|---|
| [N-MePhe¹, Leu¹³]pMOT(1-14) | 12.8 |
| [N-MePhe¹, Leu¹³, Lys¹⁴]pMOT(1-14) amide | 20 |
| [N-MePhe¹, D-Arg¹³, Leu¹³]pMOT(1-14) | 30 |
| [N-MePhe¹, D-Arg¹², Leu¹³, Lys¹⁴]pMOT(1-14) amide | 41 |
| [N-Me₃⁺Phe¹, *D-Arg*¹², Leu¹³,D-Gln¹⁴]pMOT(1-14) amide | 104 |
| [N-Me₃⁺Phe¹, *D-Arg*¹², Leu¹³]pMOT(1-14) amide | 95 |
| [N-MePhe¹, Ala¹¹, D-Arg¹², Leu¹³, Lys¹⁴]pMOT(1-14) amide | 34.3 |
| [N-MePhe¹, Ala¹¹, D-Arg¹², Leu¹³, D-Gln¹⁴]pMOT(1-14) amide | 32.6 |
| [Me₂NPhe¹, Ala¹¹, D-Arg¹², Leu¹³, D-Lys¹⁴]pMOT(1-14) amide | 47 |
| [N-Me₃⁺Phe¹, *Ala*¹¹, D-Arg¹², Leu¹³]pMOT(1-14) amide | 131.9 |
| [N-Me₃⁺Phe¹, *D-Arg*¹², Leu¹³, Lys¹⁴]pMOT(1-14) amide | 162 |
| [N-Me₃⁺Phe¹, *Ala*¹¹, D-Arg¹², Leu¹³, Lys¹⁴]pMOT(1-14) amide | 125 |

TABLE 3
Potency Of Motilin Receptor Agonists In The Canine Gastrointestinal Tract

| Compound | ED₅₀* |
|---|---|
| [Leu¹³]pMOT(1-22) | 0.17 |
| [Leu¹³]pMOT(1-14) | 20.4 |
| [N-MePhe¹, Lys¹⁴]pMOT(1-14) amide | 0.025 |
| [N-MePhe¹, D-Arg¹², Leu¹³, Lys¹⁴]pMOT(1-14) amide | 0.025 |
| [N-MePhe¹, Ala¹¹, D-Arg¹³, Leu¹³, Lys¹⁴]pMOT(1-14) amide | 0.30 |
| [N-MePhe¹, Ala³, D-Arg¹³, Leu¹³, Lys¹⁴]pMOT(1-14) amide | 0.06 |
| [Me₃N⁺Phe¹, Ala³, D-Arg¹², Leu¹³, Lys¹⁴]pMOT(1-14) amide | 0.89 |
| [N-MePhe¹, Ala³, D-Arg¹², Leu¹³]pMOT(1-14) amide | 0.024 |
| [N-MePhe¹, Ala¹¹, D-Arg¹², Leu¹³]pMOT(1-14) amide | 0.0018 |
| [Me₃N⁺Phe¹, Ala¹¹, D-Arg¹², Leu¹³]pMOT(1-14) amide | 0.026 |
| [Me₃N⁺Phe¹, D-Arg¹², Leu¹³]pMOT(1-14) amide | 0.017 |
| [Me₃N⁺Phe¹, D-Arg¹², Leu¹³, Lys¹⁴]pMOT(1-14) amide | 0.15 |
| [Me₃N⁺Phe¹, Ala¹¹, D-Arg¹², Leu¹³, Lys¹⁴]pMOT(1-14) amide | 0.12 |
| [N-MePhe¹, Ala³, Ala¹¹, D-Arg¹², Leu¹³,Lys¹⁴]pMOT(1-14) amide | 0.001 |
| [Me₃N⁺Phe¹, Ala³, Ala¹¹, D-Arg¹², Leu¹³, Lys¹⁴]pMOT(1-14) amide | 0.001 |
| [Me₂NPhe¹, Ala¹¹, D-Arg¹², Leu¹³, Lys¹⁴]pMOT(1-14) amide | 0.003 |
| [Me₂NPhe¹, Ala³, Ala³, D-Arg¹², Leu¹³,Lys¹⁴]pMOT(1-14) amide | 0.003 |
| [Me₂NPhe¹, Ala¹¹, D-Arg¹², Leu¹³, D-Lys¹⁴]pMOT(1-14) amide | 0.35 |
| [N-MePhe¹, D-Arg¹³, Leu¹³, D-Gln¹⁴]pMOT(1-14) amide | 0.0004 |
| [N-MePhe¹, Ala¹¹, D-Arg¹², Leu¹³, D-Gln¹⁴]pMOT(1-14) amide | 0.40 |
| [N-MePhe¹, D-Arg¹², Leu¹³]pMOT(1-14) | 0.40 |
| [N-MePhe¹, Ala³, Ala¹¹, D-Arg¹², Leu¹³,D-Lys¹⁴]pMOT(1-14) amide | 0.024 |
| [Me₃N⁺Phe¹, Ala³, Ala¹¹, D-Arg¹², Leu¹³,D-Lys¹⁴]pMOT(1-14) amide | 0.007 |
| [Me₂NPhe¹, D-Arg¹³, Leu¹³, Lys¹⁴]pMOT(1-14) amide | 0.002 |

*ED₅₀ is expressed in nanomoles

While a number of embodiments of this invention have been represented, it is apparent that the basic construction can be altered to provide other embodiments which utilize the invention without departing from the spirit and scope of the invention. All such modifications and variations are intended to be included within the scope of the invention as defined in the appended claims rather than the specific embodiments which have been presented by way of example.

We claim:

1. Polypeptides having gastrointestinal motor stimulating activity represented by the formula:

$$(R_1)N-\overset{R_2}{\underset{R_3}{|}}\overset{*}{C}HCO-A-B-D-E-Thr-F- \qquad (1)$$
$$\underset{CH_2R_4}{|}$$

$$-G-H-Leu-I-J-NH-\overset{*}{C}HR_6$$
$$\underset{CH_2R_5}{|}$$

including optically active isomeric forms and the pharmaceutically acceptable acid addition salts thereof wherein:

A is the L-stereoisomer of a lipophilic aliphatic amino acid;
B is L-proline or L-alanine;
D is the L-stereoisomer of a lipophilic aliphatic amino acid;
E is the L-stereoisomer of an aromatic, lipophilic aliphatic, or alicyclic amino acid;
F is the L-stereoisomer of an aromatic or heteroaromatic amino acid;
G is glycine or D-alanine;
H is L-glutamic acid or L-glutamine;
I is L-glutamine, L-glutamic acid, or L-alanine;
J is a direct bond between I and group —NH— or is selected from the group consisting of Z, Z-Leu, Z-Leu-Gln, Z-Leu-Gln-Glu, Z-Leu-Gln-Glu-Lys, Z-Leu-Gln-Glu-Lys-Glu, Z-Leu-Gln-Glu-Lys-Glu-Arg, Z-Leu-Gln-Glu-Lys-Glu-Arg-Asn, Z-Leu-Gln-Glu-Lys-Glu-Arg-Asn-Lys, and Z-Leu-Gln-Glu-Lys-Glu-Arg-Asn-Lys-Gly, wherein Z is selected from the group consisting of arginine, D-arginine, D-homoarginine, D-lysine, D-ornithine, D-2,4-diaminobutyric acid, D-glutamine, D-asparagine, and D-alanine;

$R_1$ is lower-alkyl or allyl;

$R_2$ is selected from the group consisting of hydrogen, lower-alkyl, propargyl, and allyl;

$R_3$ is selected from the group consisting of hydrogen, lower-alkyl, and allyl;

$R_4$ is cycloalkyl or aryl which may be unsubstituted or substituted with one or more substituents selected from the group consisting of halogen, hydroxy, and lower-alkoxy;

$R_5$ is selected from the group consisting of $-CH_2CONH_2$, aminoalkyl groups containing from 1 to 3 carbon atoms, and guanidinoalkyl groups containing 2 or 3 carbon atoms;

$R_6$ is $-COOH$ or $-CONH_2$; and m is 0 or 1, the symbol * represents an asymmetric carbon atom which may be in the D or L configuration, and each lower-alkyl group contains from 1 to 4 carbon atoms, with the proviso that:

(a) when m is 0, $R_2$ and $R_3$ are hydrogen, and J is a direct bond, the $-NH-*CH(CH_2R_5)R_6$ group has the D-configuration;

(b) $R_5$ is $-CH_2CONH_2$ only when J is Z-Leu or Z-Leu-Gln-Glu-Lys-Glu-Arg-Asn-Lys-Gly;

(c) when m=0, $R_2$ and $R_3$ are hydrogen, and J is Z, Z-Leu, Z-Leu-Gln, Z-Leu-Gln-Glu, Z-Leu-Gln-Glu-Lys, Z-Leu-Gln-Glu-Lys-Glu, Z-Leu-Gln-Glu-Lys-Glu-Arg, Z-Leu-Gln-Glu-Lys-Glu-Arg-Asn, Z-Leu-Gln-Glu-Lys-Glu-Arg-Asn-Lys, and Z-Leu-Gln-Glu-Lys-Glu-Arg-Asn-Lys-Gly, Z has the D configuration; and (d) the polypeptide is other than motilin.

2. The polypeptide according to claim 1, wherein $(R_1)_m(R_2)(R_3)N-*CH(CH_2R_4)CO-$ is selected from the group consisting of L-phenylalanine, D-phenylalanine, L-cyclohexylalanine, and D-cyclohexylalanine.

3. The polypeptide according to claim 1, wherein A is selected from the group consisting of L-valine, L-isoleucine, L-leucine, L-norvaline, and L-norleucine.

4. The polypeptide according to claim 1, wherein B is L-proline.

5. The polypeptide according to claim 1, wherein D is selected from the group consisting of L-isoleucine, L-valine, L-leucine, L-norvaline, and L-norleucine.

6. The polypeptide according to claim 1, wherein E is selected from the group consisting of phenylalanine, p-fluorophenylalanine, p-chlorophenylalanine, p-bromophenylalanine, p-iodophenylalanine, tyrosine, p-methoxyphenylalanine, 1-naphthylalanine, 2-naphthylalanine, leucine, and cyclohexylalanine.

7. The polypeptide according to claim 1, wherein F is selected from the group consisting of tyrosine, phenylalanine, p-methoxyphenylalanine, histidine, tryptophan, β-2-thienylalanine, and β-3-pyridylalanine.

8. The polypeptide according to claim 1, wherein I is L-glutamine or L-alanine.

9. The polypeptide according to claim 1, wherein J is a direct bond between I and group $-NH-$.

10. The polypeptide according to claim 1, wherein J is selected from the group consisting of Z-Leu, Z-Leu-Gln-Glu (SEQ ID NO:2), Z-Leu-Gln-Glu-Lys-Glu (SEQ ID NO:4), Z-Leu-Gln-Glu-Lys-Glu-Arg-Asn (SEQ ID NO:6), and Z-Leu-Gln-Glu-Lys-Glu-Arg-Asn-Lys-Gly (SEQ ID NO:8) and Z is selected from the group consisting of arginine, D-arginine, and D-glutamine.

11. The polypeptide according to claim 1, wherein m is 0.

12. The polypeptide according to claim 1, wherein $R_2$ is selected from the group consisting of hydrogen, lower-alkyl, and propargyl.

13. The polypeptide according to claim 1, wherein $R_3$ is hydrogen or lower-alkyl.

14. The polypeptide according to claim 1, wherein $R_4$ is selected from the group consisting of cyclohexyl, phenyl, p-fluorophenyl, p-chlorophenyl, p-bromophenyl, p-iodophenyl, p-hydroxyphenyl, p-methoxyphenyl, 1-naphthyl, and 2-naphthyl.

15. The polypeptide according to claim 1, wherein $R_5$ is selected from the group consisting of $-CH_2CONH_2$, and aminoalkyl groups containing from 1 to 3 carbon atoms.

16. The polypeptide according to claim 1, wherein the group $-NH*CH(CH_2R_5)-R_6$ is selected from the group consisting of arginine, D-arginine, lysine, D-lysine, glutamine, D-glutamine, D-ornithine, D-2,4-diaminobutyric acid, and D-homoarginine.

17. The polypeptide according to claim 1, wherein the polypeptide is
(N-Me)-Phe-Val-Pro-Ile-Phe-Thr-Tyr-Gly-Glu-Leu-Ala-D-Arg-Leu-Lys-NH$_2$; (SEQ ID NO: 115)
and its pharmaceutically acceptable addition salts.

18. The polypeptide according to claim 1, wherein the polypeptide is
(Me$_2$N)-Phe-Val-Pro-Ile-Phe-Thr-Tyr-Gly-Glu-Leu-Gln-D-Arg-Leu-Lys-NH$_2$; (SEQ ID NO:92)
and its pharmaceutically acceptable addition salts.

19. The polypeptide according to claim 1, wherein the polypeptide is
(Me$_3$N+)-Phe-Val-Pro-Ile-Phe-Thr-Tyr-Gly-Glu-Leu-Ala-D-Arg-Leu-Lys-NH$_2$; (SEQ ID NO: 117)
and its pharmaceutically acceptable addition salts.

20. The polypeptide according to claim 1, wherein the polypeptide is
(Me$_3$N+)-Phe-Val-Pro-Ile-Phe-Thr-Tyr-Gly-Glu-Leu-Gln-D-Arg-Leu-Gln-NH$_2$; (SEQ ID NO:32)
and its pharmaceutically acceptable addition salts.

21. The polypeptide according to claim 1, wherein the polypeptide is
(N-Me)-Phe-Val-Pro-Ile-Phe-Thr-Tyr-Gly-Glu-Leu-Gln-D-Arg-Leu-D-Gln-NH$_2$; (SEQ ID NO:86)
and its pharmaceutically acceptable addition salts.

22. The polypeptide according to claim 1, wherein the polypeptide is
(N-Me)-Phe-Val-Pro-Ile-Phe-Thr-Tyr-Gly-Glu-Leu-Gln-D-Arg-Leu-Lys-NH$_2$; (SEQ ID NO:91)
and its pharmaceutically acceptable addition salts.

23. The polypeptide according to claim 1, wherein the polypeptide is
(Me$_2$N)-Phe-Val-Pro-Ile-Phe-Thr-Tyr-Gly-Glu-Leu-Gln-D-Arg-Leu-Gln-NH$_2$; (SEQ ID NO:31)
and its pharmaceutically acceptable addition salts.

24. The polypeptide according to claim 1, wherein the polypeptide is
(Me$_3$N+)-Phe-Val-Pro-Ile-Phe-Thr-Tyr-Gly-Glu-Leu-Gln-D-Arg-Leu-Lys-NH$_2$; (SEQ ID NO:93)
and its pharmaceutically acceptable addition salts.

25. The polypeptide according to claim 1, wherein the polypeptide is
(N-Me)-Phe-Val-Pro-Ile-Phe-Thr-Tyr-Gly-Glu-Leu-Ala-D-Arg-Leu-Gln-NH$_2$; (SEQ ID NO: 103)
and its pharmaceutically acceptable addition salts.

26. The polypeptide according to claim 1, wherein the polypeptide is
(N-Me)-Phe-Val-Pro-Ile-Phe-Thr-Tyr-Gly-Glu-Leu-Gln-D-Arg-Leu-Gln-NH$_2$; (SEQ ID NO: 30)

and its pharmaceutically acceptable addition salts.

27. The polypeptide according to claim 1, wherein the polypeptide is
(Me₂N)-Phe-Val-Pro-Ile-Phe-Thr-Tyr-Gly-Glu-Leu-Ala-D-Arg-Leu-Lys-NH₂; (SEQ ID NO: 116)
and its pharmaceutically acceptable addition salts.

28. The polypeptide according to claim 1, wherein the polypeptide is
(Me₃N⁺)-Phe-Val-Pro-Ile-Phe-Thr-Tyr-Gly-Glu-Leu-Gln-D-Arg-Leu-D-Gln-NH₂; (SEQ ID NO: 88)
and its pharmaceutically acceptable addition salts.

29. The polypeptide according to claim 1, wherein the polypeptide is
(Me₃N⁺)-Phe-Val-Ala-Ile-Phe-Thr-Tyr-Gly-Glu-Leu-Ala-D-Arg-Leu-D-Lys-NH₂; (SEQ ID NO: 108)
and its pharmaceutically acceptable addition salts.

30. The polypeptide according to claim 1, wherein the polypeptide is
(Me₂N)-Phe-Val-Pro-Ile-Phe-Thr-Tyr-Gly-Glu-Leu-Ala-D-Arg-Leu-D-Lys-NH₂; (SEQ ID NO: 122)
and its pharmaceutically acceptable addition salts.

31. A method for treating a condition of decreased basal level of gastrointestinal motor activity in a mammal which comprises administering to the mammal an amount, therapeutically effective to relieve the condition, of a polypeptide represented by the formula:

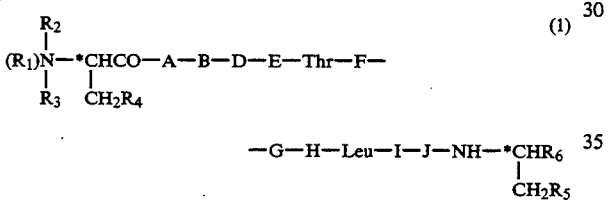

including optically active isomeric forms and the pharmaceutically acceptable acid addition salts thereof wherein:
A is the L-stereoisomer of a lipophilic aliphatic amino acid;
B is L-proline or L-alanine;
D is the L-stereoisomer of a lipophilic aliphatic amino acid;
E is the L-stereoisomer of an aromatic, lipophilic aliphatic, or alicyclic amino acid;
F is the L-stereoisomer of an aromatic or heteroaromatic amino acid;
G is glycine or D-alanine;
H is L-glutamic acid or L-glutamine;
I is L-glutamine, L-glutamic acid, or L-alanine;
J is a direct bond between I and group —NH— or is selected from the group consisting of Z, Z-Leu, Z-Leu-Gln, Z-Leu-Gln-Glu, Z-Leu-Gln-Glu-Lys, Z-Leu-Gln-Glu-Lys-Glu, Z-Leu-Gln-Glu-Lys-Glu-Arg, Z-Leu-Gln-Glu-Lys-Glu-Arg-Asn, Z-Leu-Gln-Glu-Lys-Glu-Arg-Asn-Lys, and Z-Leu-Gln-Glu-Lys-Glu-Arg-Asn-Lys-Gly, wherein Z is selected from the group consisting of arginine, D-arginine, D-homoarginine, D-lysine, D-ornithine, D-2,4-diaminobutyric acid, D-glutamine, D-asparagine, and D-alanine;
$R_1$ is lower-alkyl or allyl;
$R_2$ is selected from the group consisting of hydrogen, lower-alkyl, propargyl, and allyl;
$R_3$ is selected from the group consisting of hydrogen, lower-alkyl, and allyl;
$R_4$ is cycloalkyl or aryl which may be unsubstituted or substituted with one or more substituents selected from the group consisting of halogen, hydroxy, and lower-alkoxy;
$R_5$ is selected from the group consisting of —CH₂CONH₂, aminoalkyl groups containing from 1 to 3 carbon atoms, and guanidinoalkyl groups containing 2 or 3 carbon atoms;
$R_6$ is —COOH or —CONH₂; and
m is 0 or 1, the symbol * represents an asymmetric carbon atom which may be in the D or L configuration, and each lower-alkyl group contains from 1 to 4 carbon atoms, with the proviso that:
(a) when m is 0, $R_2$ and $R_3$ are hydrogen, and J is a direct bond, the —NH—* CH(CH₂R₅)R₆ group has the D-configuration;
b) $R_5$ is —CH₂CONH₂ only when J is Z-Leu or Z-Leu-Gln-Glu-Lys-Glu-Arg-Asn-Lys-Gly;
(c) when m=0, $R_2$ and $R_3$ are hydrogen, and J is Z, Z-Leu, Z-Leu-Gln, Z-Leu-Gln-Glu, Z-Leu-Gln-Glu-Lys, Z-Leu-Gln-Glu-Lys-Glu, Z-Leu-Gln-Glu-Lys-Glu-Arg, Z-Leu-Gln-Glu-Lys-Glu-Arg-Asn, Z-Leu-Gln-Glu-Lys-Glu-Arg-Asn-Lys, and Z-Leu-Gln-Glu-Lys-Glu-Arg-Asn-Lys-Gly, Z has the D configuration; and
(d) the polypeptide is other than motilin.

* * * * *

SEQUENCE LISTING ( 1 ) GENERAL INFORMATION:

( i i i ) NUMBER OF SEQUENCES: 173

( 2 ) INFORMATION FOR SEQ ID NO:1:

( i ) SEQUENCE CHARACTERISTICS:
    ( A ) LENGTH: 22 amino acids
    ( B ) TYPE: amino acid
    ( C ) STRANDEDNESS: unknown
    ( D ) TOPOLOGY: unknown ( i i ) MOLECULE TYPE: peptide ( x i ) SEQUENCE DESCRIPTION: SEQ ID NO:1:

Phe  Val  Pro  Ile  Phe  Thr  Tyr  Gly  Glu  Leu  Gln  Arg  Met  Gln  Glu  Lys
  1              5                        10                            15

Glu  Arg  Asn  Lys  Gly  Gln
                 20

( 2 ) INFORMATION FOR SEQ ID NO:2:

( i ) SEQUENCE CHARACTERISTICS:
    ( A ) LENGTH: 4 amino acids
    ( B ) TYPE: amino acid
    ( C ) STRANDEDNESS: unknown
    ( D ) TOPOLOGY: unknown ( i i ) MOLECULE TYPE: peptide ( x i ) SEQUENCE DESCRIPTION: SEQ ID NO:2:

```
Xaa Leu Gln Glu
 1
```

( 2 ) INFORMATION FOR SEQ ID NO:3:

( i ) SEQUENCE CHARACTERISTICS:
        ( A ) LENGTH: 5 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:3:

```
Xaa Leu Gln Glu Lys
 1               5
```

( 2 ) INFORMATION FOR SEQ ID NO:4:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:4:

```
Xaa Leu Gln Glu Lys Glu
 1               5
```

( 2 ) INFORMATION FOR SEQ ID NO:5:

( i ) SEQUENCE CHARACTERISTICS:
        ( A ) LENGTH: 7 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:5:

```
Xaa Leu Gln Glu Lys Glu Arg
 1               5
```

( 2 ) INFORMATION FOR SEQ ID NO:6:

( i ) SEQUENCE CHARACTERISTICS:
        ( A ) LENGTH: 8 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:6:

```
Xaa Leu Gln Glu Lys Glu Arg Asn
 1               5
```

( 2 ) INFORMATION FOR SEQ ID NO:7:

( i ) SEQUENCE CHARACTERISTICS:

( A ) LENGTH: 9 amino acids
          ( B ) TYPE: amino acid
          ( C ) STRANDEDNESS: unknown
          ( D ) TOPOLOGY: unknown ( i i ) MOLECULE TYPE: peptide ( x i ) SEQUENCE DESCRIPTION: SEQ ID NO:7:

Xaa  Leu  Gln  Glu  Lys  Glu  Arg  Asn  Lys
     1                  5

( 2 ) INFORMATION FOR SEQ ID NO:8:

( i ) SEQUENCE CHARACTERISTICS:
          ( A ) LENGTH: 10 amino acids
          ( B ) TYPE: amino acid
          ( C ) STRANDEDNESS: unknown
          ( D ) TOPOLOGY: unknown ( i i ) MOLECULE TYPE: peptide ( x i ) SEQUENCE DESCRIPTION: SEQ ID NO:8:

Xaa  Leu  Gln  Glu  Lys  Glu  Arg  Asn  Lys  Gly
     1                  5                      10

( 2 ) INFORMATION FOR SEQ ID NO:9:

( i ) SEQUENCE CHARACTERISTICS:
          ( A ) LENGTH: 21 amino acids
          ( B ) TYPE: amino acid
          ( C ) STRANDEDNESS: unknown
          ( D ) TOPOLOGY: unknown ( i i ) MOLECULE TYPE: peptide ( x i ) SEQUENCE DESCRIPTION: SEQ ID NO:9:

Phe  Val  Pro  Ile  Phe  Thr  Tyr  Gly  Glu  Leu  Gln  Xaa  Leu  Gln  Lys  Glu
     1                  5                      10                      15

Arg  Asn  Lys  Gly  Gln
                    20

( 2 ) INFORMATION FOR SEQ ID NO:10:

( i ) SEQUENCE CHARACTERISTICS:
          ( A ) LENGTH: 21 amino acids
          ( B ) TYPE: amino acid
          ( C ) STRANDEDNESS: unknown
          ( D ) TOPOLOGY: unknown ( i i ) MOLECULE TYPE: peptide ( x i ) SEQUENCE DESCRIPTION: SEQ ID NO:10:

Phe  Val  Pro  Ile  Phe  Thr  Tyr  Gly  Glu  Leu  Gln  Xaa  Leu  Gln  Lys  Glu
     1                  5                      10                      15

Arg  Asn  Lys  Gly  Gln
                    20

( 2 ) INFORMATION FOR SEQ ID NO:11:

( i ) SEQUENCE CHARACTERISTICS:
          ( A ) LENGTH: 21 amino acids
          ( B ) TYPE: amino acid
          ( C ) STRANDEDNESS: unknown
          ( D ) TOPOLOGY: unknown ( i i ) MOLECULE TYPE: peptide ( x i ) SEQUENCE DESCRIPTION: SEQ ID NO:11:

Phe  Val  Ala  Ile  Phe  Thr  Tyr  Gly  Glu  Leu  Gln  Xaa  Leu  Gln  Lys  Glu
     1                  5                      10                      15

Arg Asn Lys Gly Gln
       20

( 2 ) INFORMATION FOR SEQ ID NO:12:

( i ) SEQUENCE CHARACTERISTICS:
        ( A ) LENGTH: 21 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:12:

Phe Val Ala Ile Phe Thr Tyr Gly Glu Leu Gln Xaa Leu Gln Lys Glu
1               5                   10                  15

Arg Asn Lys Gly Gln
       20

( 2 ) INFORMATION FOR SEQ ID NO:13:

( i ) SEQUENCE CHARACTERISTICS:
        ( A ) LENGTH: 12 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:13:

Phe Val Pro Ile Phe Thr Tyr Gly Glu Leu Gln Xaa
1               5                   10

( 2 ) INFORMATION FOR SEQ ID NO:14:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:14:

Phe Val Pro Ile Phe Thr Tyr Gly Glu Leu Gln Xaa Leu Gln
1               5                   10

( 2 ) INFORMATION FOR SEQ ID NO:15:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:15:

Phe Val Pro Ile Phe Thr Tyr Gly Glu Leu Gln Xaa Leu Gln
1               5                   10

( 2 ) INFORMATION FOR SEQ ID NO:16:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:16:

```
        Phe  Val  Pro  Ile  Phe  Thr  Tyr  Gly  Glu  Leu  Gln  Xaa  Leu  Gln
        1                   5                        10
```

( 2 ) INFORMATION FOR SEQ ID NO:17:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:17:

```
        Phe  Val  Pro  Ile  Phe  Thr  Tyr  Gly  Glu  Leu  Gln  Xaa  Leu  Gln
        1                   5                        10
```

( 2 ) INFORMATION FOR SEQ ID NO:18:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:18:

```
        Phe  Val  Pro  Ile  Phe  Thr  Tyr  Gly  Glu  Leu  Gln  Xaa  Leu  Gln
        1                   5                        10
```

( 2 ) INFORMATION FOR SEQ ID NO:19:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:19:

```
        Phe  Val  Pro  Ile  Phe  Thr  Tyr  Gly  Glu  Leu  Gln  Xaa  Leu  Gln
        1                   5                        10
```

( 2 ) INFORMATION FOR SEQ ID NO:20:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:20:

```
        Phe  Val  Pro  Ile  Phe  Thr  Tyr  Gly  Glu  Leu  Gln  Xaa  Leu  Gln
        1                   5                        10
```

( 2 ) INFORMATION FOR SEQ ID NO:21:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:21:

```
        Phe  Val  Pro  Ile  Phe  Thr  Tyr  Gly  Glu  Leu  Gln  Xaa  Leu  Gln
```

(2) INFORMATION FOR SEQ ID NO:22:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:22:

```
Phe Val Ala Ile Phe Thr Tyr Gly Glu Leu Gln Xaa Leu Gln
 1               5                  10
```

(2) INFORMATION FOR SEQ ID NO:23:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:23:

```
Phe Val Pro Leu Phe Thr Tyr Gly Glu Leu Gln Xaa Leu Gln
 1               5                  10
```

(2) INFORMATION FOR SEQ ID NO:24:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:24:

```
Phe Val Pro Ile Xaa Thr Tyr Gly Glu Leu Gln Xaa Leu Gln
 1               5                  10
```

(2) INFORMATION FOR SEQ ID NO:25:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:25:

```
Phe Val Pro Ile Phe Thr Phe Gly Glu Leu Gln Xaa Leu Gln
 1               5                  10
```

(2) INFORMATION FOR SEQ ID NO:26:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:26:

```
Phe Val Pro Ile Phe Thr Tyr Xaa Glu Leu Gln Xaa Leu Gln
 1               5                  10
```

( 2 ) INFORMATION FOR SEQ ID NO:27:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:27:

Phe Val Pro Ile Phe Thr Tyr Gly Glu Leu Ala Xaa Leu Gln
    1                5                      10

( 2 ) INFORMATION FOR SEQ ID NO:28:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:28:

Phe Leu Pro Ile Phe Thr Tyr Gly Glu Leu Gln Xaa Leu Gln
    1                5                      10

( 2 ) INFORMATION FOR SEQ ID NO:29:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:29:

Phe Val Pro Ile Phe Thr Tyr Gly Glu Leu Gln Xaa Leu Gln
    1                5                      10

( 2 ) INFORMATION FOR SEQ ID NO:30:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:30:

Phe Val Pro Ile Phe Thr Tyr Gly Glu Leu Gln Xaa Leu Gln
    1                5                      10

( 2 ) INFORMATION FOR SEQ ID NO:31:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:31:

Phe Val Pro Ile Phe Thr Tyr Gly Glu Leu Gln Xaa Leu Gln
    1                5                      10

( 2 ) INFORMATION FOR SEQ ID NO:32:

(i) SEQUENCE CHARACTERISTICS:
    (A) LENGTH: 14 amino acids
    (B) TYPE: amino acid
    (C) STRANDEDNESS: unknown
    (D) TOPOLOGY: unknown (ii) MOLECULE TYPE: peptide (xi) SEQUENCE DESCRIPTION: SEQ ID NO:32:

Phe Val Pro Ile Phe Thr Tyr Gly Glu Leu Gln Xaa Leu Gln
1               5                   10

(2) INFORMATION FOR SEQ ID NO:33:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:33:

Phe Val Pro Ile Phe Thr Tyr Gly Glu Leu Gln Xaa Leu Gln
1               5                   10

(2) INFORMATION FOR SEQ ID NO:34:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:34:

Phe Val Pro Ile Phe Thr Tyr Gly Glu Leu Gln Xaa Leu Gln
1               5                   10

(2) INFORMATION FOR SEQ ID NO:35:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:35:

Phe Val Pro Ile Phe Thr Tyr Gly Glu Leu Gln Xaa Leu Gln
1               5                   10

(2) INFORMATION FOR SEQ ID NO:36:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:36:

Phe Val Pro Ile Phe Thr Tyr Gly Glu Leu Gln Xaa Leu Gln
1               5                   10

(2) INFORMATION FOR SEQ ID NO:37:

(i) SEQUENCE CHARACTERISTICS:

( A ) LENGTH: 14 amino acids
            ( B ) TYPE: amino acid
            ( C ) STRANDEDNESS: unknown
            ( D ) TOPOLOGY: unknown ( i i ) MOLECULE TYPE: peptide ( x i ) SEQUENCE DESCRIPTION: SEQ ID NO:37:

Phe  Val  Pro  Ile  Phe  Thr  Tyr  Gly  Glu  Leu  Gln  Xaa  Leu  Gln
    1                   5                        10

( 2 ) INFORMATION FOR SEQ ID NO:38:

( i ) SEQUENCE CHARACTERISTICS:
            ( A ) LENGTH: 14 amino acids
            ( B ) TYPE: amino acid
            ( C ) STRANDEDNESS: unknown
            ( D ) TOPOLOGY: unknown ( i i ) MOLECULE TYPE: peptide ( x i ) SEQUENCE DESCRIPTION: SEQ ID NO:38:

Phe  Val  Pro  Ile  Phe  Thr  Tyr  Gly  Glu  Leu  Gln  Xaa  Leu  Gln
    1                   5                        10

( 2 ) INFORMATION FOR SEQ ID NO:39:

( i ) SEQUENCE CHARACTERISTICS:
            ( A ) LENGTH: 14 amino acids
            ( B ) TYPE: amino acid
            ( C ) STRANDEDNESS: unknown
            ( D ) TOPOLOGY: unknown ( i i ) MOLECULE TYPE: peptide ( x i ) SEQUENCE DESCRIPTION: SEQ ID NO:39:

Phe  Val  Ala  Ile  Phe  Thr  Tyr  Gly  Glu  Leu  Gln  Xaa  Leu  Gln
    1                   5                        10

( 2 ) INFORMATION FOR SEQ ID NO:40:

( i ) SEQUENCE CHARACTERISTICS:
            ( A ) LENGTH: 14 amino acids
            ( B ) TYPE: amino acid
            ( C ) STRANDEDNESS: unknown
            ( D ) TOPOLOGY: unknown ( i i ) MOLECULE TYPE: peptide ( x i ) SEQUENCE DESCRIPTION: SEQ ID NO:40:

Phe  Val  Pro  Leu  Phe  Thr  Tyr  Gly  Glu  Leu  Gln  Xaa  Leu  Gln
    1                   5                        10

( 2 ) INFORMATION FOR SEQ ID NO:41:

( i ) SEQUENCE CHARACTERISTICS:
            ( A ) LENGTH: 14 amino acids
            ( B ) TYPE: amino acid
            ( C ) STRANDEDNESS: unknown
            ( D ) TOPOLOGY: unknown ( i i ) MOLECULE TYPE: peptide ( x i ) SEQUENCE DESCRIPTION: SEQ ID NO:41:

Phe  Val  Pro  Ile  Xaa  Thr  Tyr  Gly  Glu  Leu  Gln  Xaa  Leu  Gln
    1                   5                        10

( 2 ) INFORMATION FOR SEQ ID NO:42:

( i ) SEQUENCE CHARACTERISTICS:
            ( A ) LENGTH: 14 amino acids
            ( B ) TYPE: amino acid (C) STRANDEDNESS: unknown
(D) TOPOLOGY: unknown (ii) MOLECULE TYPE: peptide (xi) SEQUENCE DESCRIPTION: SEQ ID NO:42:

Phe Val Pro Ile Phe Thr Phe Gly Glu Leu Gln Xaa Leu Gln
1               5                   10

(2) INFORMATION FOR SEQ ID NO:43:

(i) SEQUENCE CHARACTERISTICS:
    (A) LENGTH: 14 amino acids
    (B) TYPE: amino acid
    (C) STRANDEDNESS: unknown
    (D) TOPOLOGY: unknown (ii) MOLECULE TYPE: peptide (xi) SEQUENCE DESCRIPTION: SEQ ID NO:43:

Phe Val Pro Ile Phe Thr Tyr Xaa Glu Leu Gln Xaa Leu Gln
1               5                   10

(2) INFORMATION FOR SEQ ID NO:44:

(i) SEQUENCE CHARACTERISTICS:
    (A) LENGTH: 14 amino acids
    (B) TYPE: amino acid
    (C) STRANDEDNESS: unknown
    (D) TOPOLOGY: unknown (ii) MOLECULE TYPE: peptide (xi) SEQUENCE DESCRIPTION: SEQ ID NO:44:

Phe Val Pro Ile Phe Thr Tyr Gly Glu Leu Ala Xaa Leu Gln
1               5                   10

(2) INFORMATION FOR SEQ ID NO:45:

(i) SEQUENCE CHARACTERISTICS:
    (A) LENGTH: 14 amino acids
    (B) TYPE: amino acid
    (C) STRANDEDNESS: unknown
    (D) TOPOLOGY: unknown (ii) MOLECULE TYPE: peptide (xi) SEQUENCE DESCRIPTION: SEQ ID NO:45:

Phe Leu Pro Ile Phe Thr Tyr Gly Glu Leu Gln Xaa Leu Gln
1               5                   10

(2) INFORMATION FOR SEQ ID NO:46:

(i) SEQUENCE CHARACTERISTICS:
    (A) LENGTH: 14 amino acids
    (B) TYPE: amino acid
    (C) STRANDEDNESS: unknown
    (D) TOPOLOGY: unknown (ii) MOLECULE TYPE: peptide (xi) SEQUENCE DESCRIPTION: SEQ ID NO:46:

Phe Val Pro Ile Phe Thr Tyr Gly Glu Leu Gln Xaa Leu Lys
1               5                   10

(2) INFORMATION FOR SEQ ID NO:47:

(i) SEQUENCE CHARACTERISTICS:
    (A) LENGTH: 14 amino acids
    (B) TYPE: amino acid
    (C) STRANDEDNESS: unknown
    (D) TOPOLOGY: unknown (i i) MOLECULE TYPE: peptide (x i) SEQUENCE DESCRIPTION: SEQ ID NO:47:

```
Xaa Val Pro Ile Phe Thr Tyr Gly Glu Leu Gln Xaa Leu Gln
 1               5                   10
```

(2) INFORMATION FOR SEQ ID NO:48:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (i i) MOLECULE TYPE: peptide (x i) SEQUENCE DESCRIPTION: SEQ ID NO:48:

```
Xaa Val Pro Ile Phe Thr Tyr Gly Glu Leu Gln Xaa Leu Gln
 1               5                   10
```

(2) INFORMATION FOR SEQ ID NO:49:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (i i) MOLECULE TYPE: peptide (x i) SEQUENCE DESCRIPTION: SEQ ID NO:49:

```
Phe Val Pro Ile Phe Thr Tyr Gly Glu Leu Gln Xaa Leu Gln
 1               5                   10
```

(2) INFORMATION FOR SEQ ID NO:50:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (i i) MOLECULE TYPE: peptide (x i) SEQUENCE DESCRIPTION: SEQ ID NO:50:

```
Xaa Val Pro Ile Phe Thr Tyr Gly Glu Leu Gln Xaa Leu Gln
 1               5                   10
```

(2) INFORMATION FOR SEQ ID NO:51:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (i i) MOLECULE TYPE: peptide (x i) SEQUENCE DESCRIPTION: SEQ ID NO:51:

```
Xaa Val Pro Ile Phe Thr Tyr Gly Glu Leu Gln Xaa Leu Gln
 1               5                   10
```

(2) INFORMATION FOR SEQ ID NO:52:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (i i) MOLECULE TYPE: peptide (x i) SEQUENCE DESCRIPTION: SEQ ID NO:52:

Phe Val Pro Ile Phe Thr Tyr Gly Glu Leu Gln Xaa Leu Gln
1               5                   10

(2) INFORMATION FOR SEQ ID NO:53:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (i i) MOLECULE TYPE: peptide (x i) SEQUENCE DESCRIPTION: SEQ ID NO:53:

Phe Val Pro Ile Phe Thr Tyr Gly Glu Leu Gln Xaa Leu Xaa
1               5                   10

(2) INFORMATION FOR SEQ ID NO:54:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (i i) MOLECULE TYPE: peptide (x i) SEQUENCE DESCRIPTION: SEQ ID NO:54:

Phe Val Ala Ile Phe Thr Tyr Gly Glu Leu Gln Xaa
1               5                   10

(2) INFORMATION FOR SEQ ID NO:55:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (i i) MOLECULE TYPE: peptide (x i) SEQUENCE DESCRIPTION: SEQ ID NO:55:

Phe Val Ala Ile Phe Thr Tyr Gly Glu Leu Gln Xaa Leu Gln
1               5                   10

(2) INFORMATION FOR SEQ ID NO:56:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (i i) MOLECULE TYPE: peptide (x i) SEQUENCE DESCRIPTION: SEQ ID NO:56:

Phe Val Ala Ile Phe Thr Tyr Gly Glu Leu Gln Xaa Leu Gln
1               5                   10

(2) INFORMATION FOR SEQ ID NO:57:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (i i) MOLECULE TYPE: peptide (x i) SEQUENCE DESCRIPTION: SEQ ID NO:57:

```
    Phe  Val  Ala  Ile  Phe  Thr  Tyr  Gly  Glu  Leu  Gln  Xaa  Leu  Gln
    1              5                        10
```

( 2 ) INFORMATION FOR SEQ ID NO:58:

( i ) SEQUENCE CHARACTERISTICS:
    ( A ) LENGTH: 14 amino acids
    ( B ) TYPE: amino acid
    ( C ) STRANDEDNESS: unknown
    ( D ) TOPOLOGY: unknown ( i i ) MOLECULE TYPE: peptide ( x i ) SEQUENCE DESCRIPTION: SEQ ID NO:58:

```
    Phe  Val  Ala  Ile  Phe  Thr  Tyr  Gly  Glu  Leu  Gln  Xaa  Leu  Gln
    1              5                        10
```

( 2 ) INFORMATION FOR SEQ ID NO:59:

( i ) SEQUENCE CHARACTERISTICS:
    ( A ) LENGTH: 14 amino acids
    ( B ) TYPE: amino acid
    ( C ) STRANDEDNESS: unknown
    ( D ) TOPOLOGY: unknown ( i i ) MOLECULE TYPE: peptide ( x i ) SEQUENCE DESCRIPTION: SEQ ID NO:59:

```
    Phe  Val  Ala  Leu  Phe  Thr  Tyr  Gly  Glu  Leu  Gln  Xaa  Leu  Gln
    1              5                        10
```

( 2 ) INFORMATION FOR SEQ ID NO:60:

( i ) SEQUENCE CHARACTERISTICS:
    ( A ) LENGTH: 14 amino acids
    ( B ) TYPE: amino acid
    ( C ) STRANDEDNESS: unknown
    ( D ) TOPOLOGY: unknown ( i i ) MOLECULE TYPE: peptide ( x i ) SEQUENCE DESCRIPTION: SEQ ID NO:60:

```
    Phe  Val  Ala  Ile  Xaa  Thr  Tyr  Gly  Glu  Leu  Gln  Xaa  Leu  Gln
    1              5                        10
```

( 2 ) INFORMATION FOR SEQ ID NO:61:

( i ) SEQUENCE CHARACTERISTICS:
    ( A ) LENGTH: 14 amino acids
    ( B ) TYPE: amino acid
    ( C ) STRANDEDNESS: unknown
    ( D ) TOPOLOGY: unknown ( i i ) MOLECULE TYPE: peptide ( x i ) SEQUENCE DESCRIPTION: SEQ ID NO:61:

```
    Phe  Val  Ala  Ile  Phe  Thr  Phe  Gly  Glu  Leu  Gln  Xaa  Leu  Gln
    1              5                        10
```

( 2 ) INFORMATION FOR SEQ ID NO:62:

( i ) SEQUENCE CHARACTERISTICS:
    ( A ) LENGTH: 14 amino acids
    ( B ) TYPE: amino acid
    ( C ) STRANDEDNESS: unknown
    ( D ) TOPOLOGY: unknown ( i i ) MOLECULE TYPE: peptide ( x i ) SEQUENCE DESCRIPTION: SEQ ID NO:62:

```
    Phe  Val  Ala  Ile  Phe  Thr  Tyr  Xaa  Glu  Leu  Gln  Xaa  Leu  Gln
```

(2) INFORMATION FOR SEQ ID NO:63:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:63:

```
Phe Val Ala Ile Phe Thr Tyr Gly Glu Leu Ala Xaa Leu Gln
 1               5                  10
```

(2) INFORMATION FOR SEQ ID NO:64:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:64:

```
Phe Leu Ala Ile Phe Thr Tyr Gly Glu Leu Gln Xaa Leu Gln
 1               5                  10
```

(2) INFORMATION FOR SEQ ID NO:65:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:65:

```
Phe Val Ala Ile Phe Thr Tyr Gly Glu Leu Gln Xaa Leu Gln
 1               5                  10
```

(2) INFORMATION FOR SEQ ID NO:66:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:66:

```
Phe Val Ala Ile Phe Thr Tyr Gly Glu Leu Gln Xaa Leu Gln
 1               5                  10
```

(2) INFORMATION FOR SEQ ID NO:67:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:67:

```
Phe Val Ala Ile Phe Thr Tyr Gly Glu Leu Gln Xaa Leu Gln
 1               5                  10
```

( 2 ) INFORMATION FOR SEQ ID NO:68:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:68:

```
Phe Val Ala Ile Phe Thr Tyr Gly Glu Leu Gln Xaa Leu Gln
1               5                   10
```

( 2 ) INFORMATION FOR SEQ ID NO:69:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:69:

```
Phe Val Ala Leu Phe Thr Tyr Gly Glu Leu Gln Xaa Leu Gln
1               5                   10
```

( 2 ) INFORMATION FOR SEQ ID NO:70:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:70:

```
Phe Val Ala Ile Xaa Thr Tyr Gly Glu Leu Gln Xaa Leu Gln
1               5                   10
```

( 2 ) INFORMATION FOR SEQ ID NO:71:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:71:

```
Phe Val Ala Ile Phe Thr Phe Gly Glu Leu Gln Xaa Leu Gln
1               5                   10
```

( 2 ) INFORMATION FOR SEQ ID NO:72:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:72:

```
Phe Val Ala Ile Phe Thr Tyr Xaa Glu Leu Gln Xaa Leu Gln
1               5                   10
```

( 2 ) INFORMATION FOR SEQ ID NO:73:

( i ) SEQUENCE CHARACTERISTICS:
 ( A ) LENGTH: 14 amino acids
 ( B ) TYPE: amino acid
 ( C ) STRANDEDNESS: unknown
 ( D ) TOPOLOGY: unknown ( i i ) MOLECULE TYPE: peptide ( x i ) SEQUENCE DESCRIPTION: SEQ ID NO:73:

Phe Val Ala Ile Phe Thr Tyr Gly Glu Leu Ala Xaa Leu Gln
1               5                   10

( 2 ) INFORMATION FOR SEQ ID NO:74:

( i ) SEQUENCE CHARACTERISTICS:
  ( A ) LENGTH: 14 amino acids
  ( B ) TYPE: amino acid
  ( C ) STRANDEDNESS: unknown
  ( D ) TOPOLOGY: unknown ( i i ) MOLECULE TYPE: peptide ( x i ) SEQUENCE DESCRIPTION: SEQ ID NO:74:

Phe Leu Ala Ile Phe Thr Tyr Gly Glu Leu Gln Xaa Leu Gln
1               5                   10

( 2 ) INFORMATION FOR SEQ ID NO:75:

( i ) SEQUENCE CHARACTERISTICS:
  ( A ) LENGTH: 14 amino acids
  ( B ) TYPE: amino acid
  ( C ) STRANDEDNESS: unknown
  ( D ) TOPOLOGY: unknown ( i i ) MOLECULE TYPE: peptide ( x i ) SEQUENCE DESCRIPTION: SEQ ID NO:75:

Phe Val Ala Ile Phe Thr Tyr Gly Glu Leu Gln Xaa Leu Lys
1               5                   10

( 2 ) INFORMATION FOR SEQ ID NO:76:

( i ) SEQUENCE CHARACTERISTICS:
  ( A ) LENGTH: 14 amino acids
  ( B ) TYPE: amino acid
  ( C ) STRANDEDNESS: unknown
  ( D ) TOPOLOGY: unknown ( i i ) MOLECULE TYPE: peptide ( x i ) SEQUENCE DESCRIPTION: SEQ ID NO:76:

Xaa Val Ala Ile Phe Thr Tyr Gly Glu Leu Gln Xaa Leu Gln
1               5                   10

( 2 ) INFORMATION FOR SEQ ID NO:77:

( i ) SEQUENCE CHARACTERISTICS:
  ( A ) LENGTH: 14 amino acids
  ( B ) TYPE: amino acid
  ( C ) STRANDEDNESS: unknown
  ( D ) TOPOLOGY: unknown ( i i ) MOLECULE TYPE: peptide ( x i ) SEQUENCE DESCRIPTION: SEQ ID NO:77:

Xaa Val Ala Ile Phe Thr Tyr Gly Glu Leu Gln Xaa Leu Gln
1               5                   10

( 2 ) INFORMATION FOR SEQ ID NO:78:

( i ) SEQUENCE CHARACTERISTICS:

(A) LENGTH: 14 amino acids
(B) TYPE: amino acid
(C) STRANDEDNESS: unknown
(D) TOPOLOGY: unknown (ii) MOLECULE TYPE: peptide (xi) SEQUENCE DESCRIPTION: SEQ ID NO:78:

```
Phe Val Xaa Ile Phe Thr Tyr Gly Glu Leu Gln Arg Leu Gln
1               5                   10
```

(2) INFORMATION FOR SEQ ID NO:79:

(i) SEQUENCE CHARACTERISTICS:
(A) LENGTH: 14 amino acids
(B) TYPE: amino acid
(C) STRANDEDNESS: unknown
(D) TOPOLOGY: unknown (ii) MOLECULE TYPE: peptide (xi) SEQUENCE DESCRIPTION: SEQ ID NO:79:

```
Xaa Val Ala Ile Phe Thr Tyr Gly Glu Leu Gln Xaa Leu Gln
1               5                   10
```

(2) INFORMATION FOR SEQ ID NO:80:

(i) SEQUENCE CHARACTERISTICS:
(A) LENGTH: 14 amino acids
(B) TYPE: amino acid
(C) STRANDEDNESS: unknown
(D) TOPOLOGY: unknown (ii) MOLECULE TYPE: peptide (xi) SEQUENCE DESCRIPTION: SEQ ID NO:80:

```
Xaa Val Ala Ile Phe Thr Tyr Gly Glu Leu Gln Xaa Leu Gln
1               5                   10
```

(2) INFORMATION FOR SEQ ID NO:81:

(i) SEQUENCE CHARACTERISTICS:
(A) LENGTH: 14 amino acids
(B) TYPE: amino acid
(C) STRANDEDNESS: unknown
(D) TOPOLOGY: unknown (ii) MOLECULE TYPE: peptide (xi) SEQUENCE DESCRIPTION: SEQ ID NO:81:

```
Phe Val Xaa Ile Phe Thr Tyr Gly Glu Leu Gln Arg Leu Gln
1               5                   10
```

(2) INFORMATION FOR SEQ ID NO:82:

(i) SEQUENCE CHARACTERISTICS:
(A) LENGTH: 14 amino acids
(B) TYPE: amino acid
(C) STRANDEDNESS: unknown
(D) TOPOLOGY: unknown (ii) MOLECULE TYPE: peptide (xi) SEQUENCE DESCRIPTION: SEQ ID NO:82:

```
Phe Val Ala Ile Phe Thr Tyr Gly Glu Leu Gln Xaa Leu Xaa
1               5                   10
```

(2) INFORMATION FOR SEQ ID NO:83:

(i) SEQUENCE CHARACTERISTICS:
(A) LENGTH: 14 amino acids
(B) TYPE: amino acid ( C ) STRANDEDNESS: unknown
( D ) TOPOLOGY: unknown ( i i ) MOLECULE TYPE: peptide ( x i ) SEQUENCE DESCRIPTION: SEQ ID NO:83:

```
Phe Val Ala Ile Phe Thr Tyr Gly Glu Leu Gln Xaa Leu Xaa
1               5                   10
```

( 2 ) INFORMATION FOR SEQ ID NO:84:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:84:

```
Phe Val Ala Ile Phe Thr Tyr Gly Glu Leu Gln Xaa Leu Xaa
1               5                   10
```

( 2 ) INFORMATION FOR SEQ ID NO:85:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:85:

```
Phe Val Ala Ile Phe Thr Tyr Gly Glu Leu Gln Xaa Leu Xaa
1               5                   10
```

( 2 ) INFORMATION FOR SEQ ID NO:86:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:86:

```
Phe Val Pro Ile Phe Thr Tyr Gly Glu Leu Gln Xaa Leu Xaa
1               5                   10
```

( 2 ) INFORMATION FOR SEQ ID NO:87:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:87:

```
Phe Val Pro Ile Phe Thr Tyr Gly Glu Leu Gln Xaa Leu Xaa
1               5                   10
```

( 2 ) INFORMATION FOR SEQ ID NO:88:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown (ii) MOLECULE TYPE: peptide (xi) SEQUENCE DESCRIPTION: SEQ ID NO:88:

Phe Val Pro Ile Phe Thr Tyr Gly Glu Leu Gln Xaa Leu Xaa
1               5                   10

(2) INFORMATION FOR SEQ ID NO:89:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:89:

Phe Val Ala Ile Phe Thr Tyr Gly Glu Leu Gln Xaa Leu Lys
1               5                   10

(2) INFORMATION FOR SEQ ID NO:90:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:90:

Phe Val Ala Ile Phe Thr Tyr Gly Glu Leu Gln Xaa Leu Lys
1               5                   10

(2) INFORMATION FOR SEQ ID NO:91:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:91:

Phe Val Pro Ile Phe Thr Tyr Gly Glu Leu Gln Xaa Leu Lys
1               5                   10

(2) INFORMATION FOR SEQ ID NO:92:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:92:

Phe Val Pro Ile Phe Thr Tyr Gly Glu Leu Gln Xaa Leu Lys
1               5                   10

(2) INFORMATION FOR SEQ ID NO:93:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (ii) MOLECULE TYPE: peptide ( x i ) SEQUENCE DESCRIPTION: SEQ ID NO:93:

Phe Val Pro Ile Phe Thr Tyr Gly Glu Leu Gln Xaa Leu Lys
1               5                   10

( 2 ) INFORMATION FOR SEQ ID NO:94:

( i ) SEQUENCE CHARACTERISTICS:
      ( A ) LENGTH: 14 amino acids
      ( B ) TYPE: amino acid
      ( C ) STRANDEDNESS: unknown
      ( D ) TOPOLOGY: unknown ( i i ) MOLECULE TYPE: peptide ( x i ) SEQUENCE DESCRIPTION: SEQ ID NO:94:

Phe Val Ala Ile Phe Thr Tyr Gly Glu Leu Gln Xaa Leu Xaa
1               5                   10

( 2 ) INFORMATION FOR SEQ ID NO:95:

( i ) SEQUENCE CHARACTERISTICS:
      ( A ) LENGTH: 14 amino acids
      ( B ) TYPE: amino acid
      ( C ) STRANDEDNESS: unknown
      ( D ) TOPOLOGY: unknown ( i i ) MOLECULE TYPE: peptide ( x i ) SEQUENCE DESCRIPTION: SEQ ID NO:95:

Phe Val Ala Ile Phe Thr Tyr Gly Glu Leu Gln Xaa Leu Xaa
1               5                   10

( 2 ) INFORMATION FOR SEQ ID NO:96:

( i ) SEQUENCE CHARACTERISTICS:
      ( A ) LENGTH: 14 amino acids
      ( B ) TYPE: amino acid
      ( C ) STRANDEDNESS: unknown
      ( D ) TOPOLOGY: unknown ( i i ) MOLECULE TYPE: peptide ( x i ) SEQUENCE DESCRIPTION: SEQ ID NO:96:

Phe Val Ala Ile Phe Thr Tyr Gly Glu Leu Gln Xaa Leu Xaa
1               5                   10

( 2 ) INFORMATION FOR SEQ ID NO:97:

( i ) SEQUENCE CHARACTERISTICS:
      ( A ) LENGTH: 14 amino acids
      ( B ) TYPE: amino acid
      ( C ) STRANDEDNESS: unknown
      ( D ) TOPOLOGY: unknown ( i i ) MOLECULE TYPE: peptide ( x i ) SEQUENCE DESCRIPTION: SEQ ID NO:97:

Phe Val Pro Ile Phe Thr Tyr Gly Glu Leu Gln Xaa Leu Xaa
1               5                   10

( 2 ) INFORMATION FOR SEQ ID NO:98:

( i ) SEQUENCE CHARACTERISTICS:
      ( A ) LENGTH: 14 amino acids
      ( B ) TYPE: amino acid
      ( C ) STRANDEDNESS: unknown
      ( D ) TOPOLOGY: unknown ( i i ) MOLECULE TYPE: peptide ( x i ) SEQUENCE DESCRIPTION: SEQ ID NO:98:

```
        Phe Val Pro Ile Phe Thr Tyr Gly Glu Leu Gln Xaa Leu Xaa
        1               5                   10
```

( 2 ) INFORMATION FOR SEQ ID NO:99:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:99:

```
        Phe Val Pro Ile Phe Thr Tyr Gly Glu Leu Gln Xaa Leu Xaa
        1               5                   10
```

( 2 ) INFORMATION FOR SEQ ID NO:100:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:100:

```
        Phe Val Ala Ile Phe Thr Tyr Gly Glu Leu Ala Xaa Leu Gln
        1               5                   10
```

( 2 ) INFORMATION FOR SEQ ID NO:101:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:101:

```
        Phe Val Ala Ile Phe Thr Tyr Gly Glu Leu Ala Xaa Leu Gln
        1               5                   10
```

( 2 ) INFORMATION FOR SEQ ID NO:102:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:102:

```
        Phe Val Ala Ile Phe Thr Tyr Gly Glu Leu Ala Xaa Leu Gln
        1               5                   10
```

( 2 ) INFORMATION FOR SEQ ID NO:103:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:103:

```
        Phe Val Pro Ile Phe Thr Tyr Gly Glu Leu Ala Xaa Leu Gln
```

( 2 ) INFORMATION FOR SEQ ID NO:104:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:104:

```
Phe Val Pro Ile Phe Thr Tyr Gly Glu Leu Ala Xaa Leu Gln
1               5                   10
```

( 2 ) INFORMATION FOR SEQ ID NO:105:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:105:

```
Phe Val Pro Ile Phe Thr Tyr Gly Glu Leu Ala Xaa Leu Gln
1               5                   10
```

( 2 ) INFORMATION FOR SEQ ID NO:106:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:106:

```
Phe Val Ala Ile Phe Thr Tyr Gly Glu Leu Ala Xaa Leu Xaa
1               5                   10
```

( 2 ) INFORMATION FOR SEQ ID NO:107:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:107:

```
Phe Val Ala Ile Phe Thr Tyr Gly Glu Leu Ala Xaa Leu Xaa
1               5                   10
```

( 2 ) INFORMATION FOR SEQ ID NO:108:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:108:

```
Phe Val Ala Ile Phe Thr Tyr Gly Glu Leu Ala Xaa Leu Xaa
1               5                   10
```

( 2 ) INFORMATION FOR SEQ ID NO:109:

( i ) SEQUENCE CHARACTERISTICS:
       ( A ) LENGTH: 14 amino acids
       ( B ) TYPE: amino acid
       ( C ) STRANDEDNESS: unknown
       ( D ) TOPOLOGY: unknown ( i i ) MOLECULE TYPE: peptide ( x i ) SEQUENCE DESCRIPTION: SEQ ID NO:109:

Phe Val Pro Ile Phe Thr Tyr Gly Glu Leu Ala Xaa Leu Xaa
   1               5                   10

( 2 ) INFORMATION FOR SEQ ID NO:110:

( i ) SEQUENCE CHARACTERISTICS:
       ( A ) LENGTH: 14 amino acids
       ( B ) TYPE: amino acid
       ( C ) STRANDEDNESS: unknown
       ( D ) TOPOLOGY: unknown ( i i ) MOLECULE TYPE: peptide ( x i ) SEQUENCE DESCRIPTION: SEQ ID NO:110:

Phe Val Pro Ile Phe Thr Tyr Gly Glu Leu Ala Xaa Leu Xaa
   1               5                   10

( 2 ) INFORMATION FOR SEQ ID NO:111:

( i ) SEQUENCE CHARACTERISTICS:
       ( A ) LENGTH: 14 amino acids
       ( B ) TYPE: amino acid
       ( C ) STRANDEDNESS: unknown
       ( D ) TOPOLOGY: unknown ( i i ) MOLECULE TYPE: peptide ( x i ) SEQUENCE DESCRIPTION: SEQ ID NO:111:

Phe Val Pro Ile Phe Thr Tyr Gly Glu Leu Ala Xaa Leu Xaa
   1               5                   10

( 2 ) INFORMATION FOR SEQ ID NO:112:

( i ) SEQUENCE CHARACTERISTICS:
       ( A ) LENGTH: 14 amino acids
       ( B ) TYPE: amino acid
       ( C ) STRANDEDNESS: unknown
       ( D ) TOPOLOGY: unknown ( i i ) MOLECULE TYPE: peptide ( x i ) SEQUENCE DESCRIPTION: SEQ ID NO:112:

Phe Val Ala Ile Phe Thr Tyr Gly Glu Leu Ala Xaa Leu Lys
   1               5                   10

( 2 ) INFORMATION FOR SEQ ID NO:113:

( i ) SEQUENCE CHARACTERISTICS:
       ( A ) LENGTH: 14 amino acids
       ( B ) TYPE: amino acid
       ( C ) STRANDEDNESS: unknown
       ( D ) TOPOLOGY: unknown ( i i ) MOLECULE TYPE: peptide ( x i ) SEQUENCE DESCRIPTION: SEQ ID NO:113:

Phe Val Ala Ile Phe Thr Tyr Gly Glu Leu Ala Xaa Leu Lys
   1               5                   10

( 2 ) INFORMATION FOR SEQ ID NO:114:

( i ) SEQUENCE CHARACTERISTICS:
    ( A ) LENGTH: 14 amino acids
    ( B ) TYPE: amino acid
    ( C ) STRANDEDNESS: unknown
    ( D ) TOPOLOGY: unknown ( i i ) MOLECULE TYPE: peptide ( x i ) SEQUENCE DESCRIPTION: SEQ ID NO:114:

Phe Val Ala Ile Phe Thr Tyr Gly Glu Leu Ala Xaa Leu Lys
1               5                   10

( 2 ) INFORMATION FOR SEQ ID NO:115:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:115:

Phe Val Pro Ile Phe Thr Tyr Gly Glu Leu Ala Xaa Leu Lys
1               5                   10

( 2 ) INFORMATION FOR SEQ ID NO:116:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:116:

Phe Val Pro Ile Phe Thr Tyr Gly Glu Leu Ala Xaa Leu Lys
1               5                   10

( 2 ) INFORMATION FOR SEQ ID NO:117:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:117:

Phe Val Pro Ile Phe Thr Tyr Gly Glu Leu Ala Xaa Leu Lys
1               5                   10

( 2 ) INFORMATION FOR SEQ ID NO:118:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:118:

Phe Val Ala Ile Phe Thr Tyr Gly Glu Leu Ala Xaa Leu Xaa
1               5                   10

( 2 ) INFORMATION FOR SEQ ID NO:119:

( i ) SEQUENCE CHARACTERISTICS:

(A) LENGTH: 14 amino acids
(B) TYPE: amino acid
(C) STRANDEDNESS: unknown
(D) TOPOLOGY: unknown (ii) MOLECULE TYPE: peptide (xi) SEQUENCE DESCRIPTION: SEQ ID NO:119:

Phe Val Ala Ile Phe Thr Tyr Gly Glu Leu Ala Xaa Leu Xaa
1               5                   10

(2) INFORMATION FOR SEQ ID NO:120:

(i) SEQUENCE CHARACTERISTICS:
(A) LENGTH: 14 amino acids
(B) TYPE: amino acid
(C) STRANDEDNESS: unknown
(D) TOPOLOGY: unknown (ii) MOLECULE TYPE: peptide (xi) SEQUENCE DESCRIPTION: SEQ ID NO:120:

Phe Val Ala Ile Phe Thr Tyr Gly Glu Leu Ala Xaa Leu Xaa
1               5                   10

(2) INFORMATION FOR SEQ ID NO:121:

(i) SEQUENCE CHARACTERISTICS:
(A) LENGTH: 14 amino acids
(B) TYPE: amino acid
(C) STRANDEDNESS: unknown
(D) TOPOLOGY: unknown (ii) MOLECULE TYPE: peptide (xi) SEQUENCE DESCRIPTION: SEQ ID NO:121:

Phe Val Pro Ile Phe Thr Tyr Gly Glu Leu Ala Xaa Leu Xaa
1               5                   10

(2) INFORMATION FOR SEQ ID NO:122:

(i) SEQUENCE CHARACTERISTICS:
(A) LENGTH: 14 amino acids
(B) TYPE: amino acid
(C) STRANDEDNESS: unknown
(D) TOPOLOGY: unknown (ii) MOLECULE TYPE: peptide (xi) SEQUENCE DESCRIPTION: SEQ ID NO:122:

Phe Val Pro Ile Phe Thr Tyr Gly Glu Leu Ala Xaa Leu Xaa
1               5                   10

(2) INFORMATION FOR SEQ ID NO:123:

(i) SEQUENCE CHARACTERISTICS:
(A) LENGTH: 14 amino acids
(B) TYPE: amino acid
(C) STRANDEDNESS: unknown
(D) TOPOLOGY: unknown (ii) MOLECULE TYPE: peptide (xi) SEQUENCE DESCRIPTION: SEQ ID NO:123:

Phe Val Pro Ile Phe Thr Tyr Gly Glu Leu Ala Xaa Leu Xaa
1               5                   10

(2) INFORMATION FOR SEQ ID NO:124:

(i) SEQUENCE CHARACTERISTICS:
(A) LENGTH: 12 amino acids
(B) TYPE: amino acid (C) STRANDEDNESS: unknown
(D) TOPOLOGY: unknown (i i) MOLECULE TYPE: peptide (x i) SEQUENCE DESCRIPTION: SEQ ID NO:124:

Phe Val Ala Ile Phe Thr Tyr Gly Glu Leu Gln Xaa
1               5                   10

(2) INFORMATION FOR SEQ ID NO:125:

(i) SEQUENCE CHARACTERISTICS:
    (A) LENGTH: 12 amino acids
    (B) TYPE: amino acid
    (C) STRANDEDNESS: unknown
    (D) TOPOLOGY: unknown (i i) MOLECULE TYPE: peptide (x i) SEQUENCE DESCRIPTION: SEQ ID NO:125:

Phe Val Ala Ile Phe Thr Tyr Gly Glu Leu Gln Xaa
1               5                   10

(2) INFORMATION FOR SEQ ID NO:126:

(i) SEQUENCE CHARACTERISTICS:
    (A) LENGTH: 12 amino acids
    (B) TYPE: amino acid
    (C) STRANDEDNESS: unknown
    (D) TOPOLOGY: unknown (i i) MOLECULE TYPE: peptide (x i) SEQUENCE DESCRIPTION: SEQ ID NO:126:

Phe Val Ala Ile Phe Thr Tyr Gly Glu Leu Gln Xaa
1               5                   10

(2) INFORMATION FOR SEQ ID NO:127:

(i) SEQUENCE CHARACTERISTICS:
    (A) LENGTH: 12 amino acids
    (B) TYPE: amino acid
    (C) STRANDEDNESS: unknown
    (D) TOPOLOGY: unknown (i i) MOLECULE TYPE: peptide (x i) SEQUENCE DESCRIPTION: SEQ ID NO:127:

Phe Val Pro Ile Phe Thr Tyr Gly Glu Leu Gln Xaa
1               5                   10

(2) INFORMATION FOR SEQ ID NO:128:

(i) SEQUENCE CHARACTERISTICS:
    (A) LENGTH: 12 amino acids
    (B) TYPE: amino acid
    (C) STRANDEDNESS: unknown
    (D) TOPOLOGY: unknown (i i) MOLECULE TYPE: peptide (x i) SEQUENCE DESCRIPTION: SEQ ID NO:128:

Phe Val Pro Ile Phe Thr Tyr Gly Glu Leu Gln Xaa
1               5                   10

(2) INFORMATION FOR SEQ ID NO:129:

(i) SEQUENCE CHARACTERISTICS:
    (A) LENGTH: 12 amino acids
    (B) TYPE: amino acid
    (C) STRANDEDNESS: unknown
    (D) TOPOLOGY: unknown (i i) MOLECULE TYPE: peptide (x i) SEQUENCE DESCRIPTION: SEQ ID NO:129:

```
Phe Val Pro Ile Phe Thr Tyr Gly Glu Leu Gln Xaa
1               5                   10
```

(2) INFORMATION FOR SEQ ID NO:130:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (i i) MOLECULE TYPE: peptide (x i) SEQUENCE DESCRIPTION: SEQ ID NO:130:

```
Phe Val Pro Ile Phe Thr Tyr Gly Glu Leu Ala Xaa
1               5                   10
```

(2) INFORMATION FOR SEQ ID NO:131:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (i i) MOLECULE TYPE: peptide (x i) SEQUENCE DESCRIPTION: SEQ ID NO:131:

```
Phe Val Pro Ile Phe Thr Tyr Gly Glu Leu Ala Xaa
1               5                   10
```

(2) INFORMATION FOR SEQ ID NO:132:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (i i) MOLECULE TYPE: peptide (x i) SEQUENCE DESCRIPTION: SEQ ID NO:132:

```
Phe Val Pro Ile Phe Thr Tyr Gly Glu Leu Ala Xaa
1               5                   10
```

(2) INFORMATION FOR SEQ ID NO:133:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (i i) MOLECULE TYPE: peptide (x i) SEQUENCE DESCRIPTION: SEQ ID NO:133:

```
Xaa Val Ala Ile Phe Thr Tyr Gly Glu Leu Ala Xaa Leu Xaa
1               5                   10
```

(2) INFORMATION FOR SEQ ID NO:134:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (i i) MOLECULE TYPE: peptide ( x i ) SEQUENCE DESCRIPTION: SEQ ID NO:134:

Phe Val Pro Ile Phe Thr Tyr Gly Glu Leu Gln Arg
1               5                   10

( 2 ) INFORMATION FOR SEQ ID NO:135:

( i ) SEQUENCE CHARACTERISTICS:
        ( A ) LENGTH: 12 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:135:

Phe Val Pro Ile Phe Thr Tyr Gly Glu Leu Gln Arg
1               5                   10

( 2 ) INFORMATION FOR SEQ ID NO:136:

( i ) SEQUENCE CHARACTERISTICS:
        ( A ) LENGTH: 12 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:136:

Phe Val Pro Ile Phe Thr Tyr Gly Glu Leu Gln Arg
1               5                   10

( 2 ) INFORMATION FOR SEQ ID NO:137:

( i ) SEQUENCE CHARACTERISTICS:
        ( A ) LENGTH: 12 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:137:

Phe Val Pro Ile Phe Thr Tyr Gly Glu Leu Gln Xaa
1               5                   10

( 2 ) INFORMATION FOR SEQ ID NO:138:

( i ) SEQUENCE CHARACTERISTICS:
        ( A ) LENGTH: 12 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:138:

Phe Val Pro Ile Phe Thr Tyr Gly Glu Leu Gln Xaa
1               5                   10

( 2 ) INFORMATION FOR SEQ ID NO:139:

( i ) SEQUENCE CHARACTERISTICS:
        ( A ) LENGTH: 12 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:139:

```
    Phe  Val  Pro  Ile  Phe  Thr  Tyr  Gly  Glu  Leu  Gln  Xaa
    1              5                        10
```

(2) INFORMATION FOR SEQ ID NO:140:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:140:

```
    Phe  Val  Ala  Ile  Phe  Thr  Tyr  Gly  Glu  Leu  Gln  Arg
    1              5                        10
```

(2) INFORMATION FOR SEQ ID NO:141:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:141:

```
    Phe  Val  Ala  Ile  Phe  Thr  Tyr  Gly  Glu  Leu  Gln  Arg
    1              5                        10
```

(2) INFORMATION FOR SEQ ID NO:142:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:142:

```
    Phe  Val  Ala  Ile  Phe  Thr  Tyr  Gly  Glu  Leu  Gln  Arg
    1              5                        10
```

(2) INFORMATION FOR SEQ ID NO:143:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:143:

```
    Phe  Val  Ala  Ile  Phe  Thr  Tyr  Gly  Glu  Leu  Gln  Xaa
    1              5                        10
```

(2) INFORMATION FOR SEQ ID NO:144:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:144:

```
    Phe  Val  Ala  Ile  Phe  Thr  Tyr  Gly  Glu  Leu  Gln  Xaa
```

( 2 ) INFORMATION FOR SEQ ID NO:145:

( i ) SEQUENCE CHARACTERISTICS:
        ( A ) LENGTH: 12 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:145:

```
Phe Val Ala Ile Phe Thr Tyr Gly Glu Leu Gln Xaa
1               5                   10
```

( 2 ) INFORMATION FOR SEQ ID NO:146:

( i ) SEQUENCE CHARACTERISTICS:
        ( A ) LENGTH: 12 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:146:

```
Phe Val Ala Ile Phe Thr Tyr Gly Glu Leu Ala Arg
1               5                   10
```

( 2 ) INFORMATION FOR SEQ ID NO:147:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:147:

```
Phe Val Ala Ile Phe Thr Tyr Gly Glu Leu Gln Xaa Leu Lys
1               5                   10
```

( 2 ) INFORMATION FOR SEQ ID NO:148:

( i ) SEQUENCE CHARACTERISTICS:
        ( A ) LENGTH: 12 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:148:

```
Phe Val Ala Ile Phe Thr Tyr Gly Glu Leu Ala Arg
1               5                   10
```

( 2 ) INFORMATION FOR SEQ ID NO:149:

( i ) SEQUENCE CHARACTERISTICS:
        ( A ) LENGTH: 12 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:149:

```
Phe Val Ala Ile Phe Thr Tyr Gly Glu Leu Ala Arg
1               5                   10
```

( 2 ) INFORMATION FOR SEQ ID NO:150:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:150:

```
Phe Val Pro Ile Phe Thr Tyr Gly Glu Leu Gln Arg Leu Lys
 1               5                  10
```

( 2 ) INFORMATION FOR SEQ ID NO:151:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:151:

```
Phe Val Pro Ile Phe Thr Tyr Gly Glu Leu Gln Arg Leu Lys
 1               5                  10
```

( 2 ) INFORMATION FOR SEQ ID NO:152:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:152:

```
Phe Val Pro Ile Phe Thr Tyr Gly Glu Leu Gln Arg Leu Lys
 1               5                  10
```

( 2 ) INFORMATION FOR SEQ ID NO:153:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:153:

```
Phe Val Ala Ile Phe Thr Tyr Gly Glu Leu Gln Arg Leu Lys
 1               5                  10
```

( 2 ) INFORMATION FOR SEQ ID NO:154:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:154:

```
Phe Val Ala Ile Phe Thr Tyr Gly Glu Leu Gln Arg Leu Lys
 1               5                  10
```

( 2 ) INFORMATION FOR SEQ ID NO:155:

(i) SEQUENCE CHARACTERISTICS:
    (A) LENGTH: 14 amino acids
    (B) TYPE: amino acid
    (C) STRANDEDNESS: unknown
    (D) TOPOLOGY: unknown (ii) MOLECULE TYPE: peptide (xi) SEQUENCE DESCRIPTION: SEQ ID NO:155:

Phe Val Ala Ile Phe Thr Tyr Gly Glu Leu Gln Arg Leu Lys
1               5                   10

(2) INFORMATION FOR SEQ ID NO:156:

(i) SEQUENCE CHARACTERISTICS:
    (A) LENGTH: 14 amino acids
    (B) TYPE: amino acid
    (C) STRANDEDNESS: unknown
    (D) TOPOLOGY: unknown (ii) MOLECULE TYPE: peptide (xi) SEQUENCE DESCRIPTION: SEQ ID NO:156:

Phe Val Pro Ile Phe Thr Tyr Gly Glu Leu Ala Arg Leu Lys
1               5                   10

(2) INFORMATION FOR SEQ ID NO:157:

(i) SEQUENCE CHARACTERISTICS:
    (A) LENGTH: 14 amino acids
    (B) TYPE: amino acid
    (C) STRANDEDNESS: unknown
    (D) TOPOLOGY: unknown (ii) MOLECULE TYPE: peptide (xi) SEQUENCE DESCRIPTION: SEQ ID NO:157:

Phe Val Pro Ile Phe Thr Tyr Gly Glu Leu Ala Arg Leu Lys
1               5                   10

(2) INFORMATION FOR SEQ ID NO:158:

(i) SEQUENCE CHARACTERISTICS:
    (A) LENGTH: 14 amino acids
    (B) TYPE: amino acid
    (C) STRANDEDNESS: unknown
    (D) TOPOLOGY: unknown (ii) MOLECULE TYPE: peptide (xi) SEQUENCE DESCRIPTION: SEQ ID NO:158:

Phe Val Pro Ile Phe Thr Tyr Gly Glu Leu Ala Arg Leu Lys
1               5                   10

(2) INFORMATION FOR SEQ ID NO:159:

(i) SEQUENCE CHARACTERISTICS:
    (A) LENGTH: 14 amino acids
    (B) TYPE: amino acid
    (C) STRANDEDNESS: unknown
    (D) TOPOLOGY: unknown (ii) MOLECULE TYPE: peptide (xi) SEQUENCE DESCRIPTION: SEQ ID NO:159:

Phe Val Ala Ile Phe Thr Tyr Gly Glu Leu Ala Arg Leu Lys
1               5                   10

(2) INFORMATION FOR SEQ ID NO:160:

(i) SEQUENCE CHARACTERISTICS:

(A) LENGTH: 14 amino acids
(B) TYPE: amino acid
(C) STRANDEDNESS: unknown
(D) TOPOLOGY: unknown (ii) MOLECULE TYPE: peptide (xi) SEQUENCE DESCRIPTION: SEQ ID NO:160:

Phe Val Ala Ile Phe Thr Tyr Gly Glu Leu Ala Arg Leu Lys
1               5                   10

(2) INFORMATION FOR SEQ ID NO:161:

(i) SEQUENCE CHARACTERISTICS:
    (A) LENGTH: 14 amino acids
    (B) TYPE: amino acid
    (C) STRANDEDNESS: unknown
    (D) TOPOLOGY: unknown (ii) MOLECULE TYPE: peptide (xi) SEQUENCE DESCRIPTION: SEQ ID NO:161:

Phe Val Ala Ile Phe Thr Tyr Gly Glu Leu Ala Arg Leu Lys
1               5                   10

(2) INFORMATION FOR SEQ ID NO:162:

(i) SEQUENCE CHARACTERISTICS:
    (A) LENGTH: 14 amino acids
    (B) TYPE: amino acid
    (C) STRANDEDNESS: unknown
    (D) TOPOLOGY: unknown (ii) MOLECULE TYPE: peptide (xi) SEQUENCE DESCRIPTION: SEQ ID NO:162:

Phe Val Pro Ile Phe Thr Tyr Gly Glu Leu Gln Arg Leu Xaa
1               5                   10

(2) INFORMATION FOR SEQ ID NO:163:

(i) SEQUENCE CHARACTERISTICS:
    (A) LENGTH: 14 amino acids
    (B) TYPE: amino acid
    (C) STRANDEDNESS: unknown
    (D) TOPOLOGY: unknown (ii) MOLECULE TYPE: peptide (xi) SEQUENCE DESCRIPTION: SEQ ID NO:163:

Phe Val Pro Ile Phe Thr Tyr Gly Glu Leu Gln Arg Leu Xaa
1               5                   10

(2) INFORMATION FOR SEQ ID NO:164:

(i) SEQUENCE CHARACTERISTICS:
    (A) LENGTH: 14 amino acids
    (B) TYPE: amino acid
    (C) STRANDEDNESS: unknown
    (D) TOPOLOGY: unknown (ii) MOLECULE TYPE: peptide (xi) SEQUENCE DESCRIPTION: SEQ ID NO:164:

Phe Val Pro Ile Phe Thr Tyr Gly Glu Leu Gln Arg Leu Xaa
1               5                   10

(2) INFORMATION FOR SEQ ID NO:165:

(i) SEQUENCE CHARACTERISTICS:
    (A) LENGTH: 14 amino acids
    (B) TYPE: amino acid (C) STRANDEDNESS: unknown
(D) TOPOLOGY: unknown (ii) MOLECULE TYPE: peptide (xi) SEQUENCE DESCRIPTION: SEQ ID NO:165:

Phe Val Ala Ile Phe Thr Tyr Gly Glu Leu Gln Arg Leu Xaa
1               5                   10

(2) INFORMATION FOR SEQ ID NO:166:

(i) SEQUENCE CHARACTERISTICS:
(A) LENGTH: 14 amino acids
(B) TYPE: amino acid
(C) STRANDEDNESS: unknown
(D) TOPOLOGY: unknown (ii) MOLECULE TYPE: peptide (xi) SEQUENCE DESCRIPTION: SEQ ID NO:166:

Phe Val Ala Ile Phe Thr Tyr Gly Glu Leu Gln Arg Leu Xaa
1               5                   10

(2) INFORMATION FOR SEQ ID NO:167:

(i) SEQUENCE CHARACTERISTICS:
(A) LENGTH: 14 amino acids
(B) TYPE: amino acid
(C) STRANDEDNESS: unknown
(D) TOPOLOGY: unknown (ii) MOLECULE TYPE: peptide (xi) SEQUENCE DESCRIPTION: SEQ ID NO:167:

Phe Val Ala Ile Phe Thr Tyr Gly Glu Leu Gln Arg Leu Xaa
1               5                   10

(2) INFORMATION FOR SEQ ID NO:168:

(i) SEQUENCE CHARACTERISTICS:
(A) LENGTH: 14 amino acids
(B) TYPE: amino acid
(C) STRANDEDNESS: unknown
(D) TOPOLOGY: unknown (ii) MOLECULE TYPE: peptide (xi) SEQUENCE DESCRIPTION: SEQ ID NO:168:

Phe Val Pro Ile Phe Thr Tyr Gly Glu Leu Ala Arg Leu Xaa
1               5                   10

(2) INFORMATION FOR SEQ ID NO:169:

(i) SEQUENCE CHARACTERISTICS:
(A) LENGTH: 14 amino acids
(B) TYPE: amino acid
(C) STRANDEDNESS: unknown
(D) TOPOLOGY: unknown (ii) MOLECULE TYPE: peptide (xi) SEQUENCE DESCRIPTION: SEQ ID NO:169:

Phe Val Pro Ile Phe Thr Tyr Gly Glu Leu Ala Arg Leu Xaa
1               5                   10

(2) INFORMATION FOR SEQ ID NO:170:

(i) SEQUENCE CHARACTERISTICS:
(A) LENGTH: 14 amino acids
(B) TYPE: amino acid
(C) STRANDEDNESS: unknown
(D) TOPOLOGY: unknown (i i) MOLECULE TYPE: peptide (x i) SEQUENCE DESCRIPTION: SEQ ID NO:170:

Phe Val Pro Ile Phe Thr Tyr Gly Glu Leu Ala Arg Leu Xaa
1               5                   10

(2) INFORMATION FOR SEQ ID NO:171:

(i) SEQUENCE CHARACTERISTICS:
      (A) LENGTH: 14 amino acids
      (B) TYPE: amino acid
      (C) STRANDEDNESS: unknown
      (D) TOPOLOGY: unknown (i i) MOLECULE TYPE: peptide (x i) SEQUENCE DESCRIPTION: SEQ ID NO:171:

Phe Val Ala Ile Phe Thr Tyr Gly Glu Leu Ala Arg Leu Xaa
1               5                   10

(2) INFORMATION FOR SEQ ID NO:172:

(i) SEQUENCE CHARACTERISTICS:
      (A) LENGTH: 14 amino acids
      (B) TYPE: amino acid
      (C) STRANDEDNESS: unknown
      (D) TOPOLOGY: unknown (i i) MOLECULE TYPE: peptide (x i) SEQUENCE DESCRIPTION: SEQ ID NO:172:

Phe Val Ala Ile Phe Thr Tyr Gly Glu Leu Ala Arg Leu Xaa
1               5                   10

(2) INFORMATION FOR SEQ ID NO:173:

(i) SEQUENCE CHARACTERISTICS:
      (A) LENGTH: 14 amino acids
      (B) TYPE: amino acid
      (C) STRANDEDNESS: unknown
      (D) TOPOLOGY: unknown (i i) MOLECULE TYPE: peptide (x i) SEQUENCE DESCRIPTION: SEQ ID NO:173:

Phe Val Ala Ile Phe Thr Tyr Gly Glu Leu Ala Arg Leu Xaa
1               5                   10